US012753427B2

(12) United States Patent
Shin et al.

(10) Patent No.: US 12,753,427 B2
(45) Date of Patent: Oct. 6, 2026

(54) # ELECTROCHEMICAL BIOSENSOR, OR SENSING MEMBRANE FOR ELECTROCHEMICAL BIOSENSOR CONTAINING TRANSITION METAL COMPLEX OR OXIDATION-REDUCTION POLYMER

(71) Applicant: I-sens, Inc., Seoul (KR)

(72) Inventors: Hyunseo Shin, Seoul (KR); Bona Yang, Seoul (KR); Geunhee Kang, Seoul (KR); Su-jin Kim, Seoul (KR); Areum Yu, Seoul (KR)

(73) Assignee: I-SENS, INC., Seoul (KR)

( * ) Notice: Subject to any disclaimer, the term of this patent is extended or adjusted under 35 U.S.C. 154(b) by 334 days.

(21) Appl. No.: 18/287,225

(22) PCT Filed: Apr. 19, 2022

(86) PCT No.: PCT/KR2022/005626

§ 371 (c)(1),
(2) Date: Oct. 17, 2023

(87) PCT Pub. No.: WO2022/225313

PCT Pub. Date: Oct. 27, 2022

(65) Prior Publication Data

US 2024/0376513 A1 Nov. 14, 2024

(30) Foreign Application Priority Data

Apr. 19, 2021 (KR) ........................ 10-2021-0050610

(51) Int. Cl.

| | |
|---|---|
| ***C12Q 1/00*** | (2006.01) |
| ***A61B 5/145*** | (2006.01) |
| ***A61B 5/1473*** | (2006.01) |
| ***C07F 15/00*** | (2006.01) |
| ***C07F 15/02*** | (2006.01) |
| ***C08F 230/04*** | (2006.01) |
| ***C12Q 1/26*** | (2006.01) |
| ***C12Q 1/54*** | (2006.01) |

(52) U.S. Cl.

CPC .......... *C12Q 1/006* (2013.01); *A61B 5/14532* (2013.01); *A61B 5/1473* (2013.01); *C07F 15/0026* (2013.01); *C07F 15/0053* (2013.01); *C07F 15/025* (2013.01); *C08F 230/04* (2013.01); *C12Q 1/26* (2013.01); *C12Q 1/54* (2013.01)

(58) Field of Classification Search

CPC .. G01N 27/00; G01N 27/327; G01N 27/3271; G01N 27/3272; G01N 27/3273; G01N 27/3274; C12Q 1/004; C12Q 1/006; C12Q 1/26; C12Q 1/54; C12Q 1/32; A61B 5/14532; A61B 5/1473; C07F 15/0026; C07F 15/0053; C07F 15/025

See application file for complete search history.

(56) References Cited

U.S. PATENT DOCUMENTS

| | | | | |
|---|---|---|---|---|
| 2005/0137400 | A1 | 6/2005 | Tao | |
| 2009/0058281 | A1 | 3/2009 | Tao et al. | |
| 2009/0255811 | A1* | 10/2009 | Forrow | C12Q 1/001 427/595 |
| 2012/0138484 | A1* | 6/2012 | Bommakanti | C12Q 1/006 204/403.14 |
| 2019/0004005 | A1* | 1/2019 | Oja | G01N 27/3272 |

FOREIGN PATENT DOCUMENTS

| | | |
|---|---|---|
| KR | 10-2016-0082160 | 7/2016 |
| KR | 10-2020-0133678 | 11/2020 |
| WO | 2004-009604 | 1/2004 |
| WO | 2009-129108 | 10/2009 |

OTHER PUBLICATIONS

Peter J. Steel, "Synthesis, Spectroscopy, and Electrochemistry of Homo- and Hetero-leptic Ruthenium(II) Complexes of New Pyrazole-containing Bidentate Ligands", J. Chem. Soc. Dalto Trans., Jan. 1, 1990, pp. 1389-1396.
R. Hage et al., "Synthesis, separation, and NMR characterisation of the fac- and mer-isomers of tris(1-methyl-3-(pyridin-2-yl)-1,2,4-triazole)ruthenium(II) hexafluorophosphate", Inorganica Chimica Acta, Dec. 31, 1986, pp. 73-76.
Nicola Monti et al., "Antibacterial activity of a new class of tris homoleptic Ru (II)-complexes with alkyl-tetrazoles as diimine-type ligands", Appl Organomet Chem., e5806, Dec. 31, 2020, pp. 1-14.
SIPO, Office Action of CN 202280029276.5 dated Jul. 5, 2025, total 9 pages.
JPO, Office Action of JP 2023-564256 dated Sep. 5, 2024, total 10 pages.
Nityananda Saha et al., "Magnetic and Spectroscopic Studies on some New Bis-and Tris-complexes of Iron(II) with 3,5-Dimethyl-1-(2-pyridyl)pyrazole : Indication of 5T2-1A1 Equilibrium", Journal of the Indian Chemical Society, Aug.-Oct. 1989, 66 (8), pp. 521-524.
Bobby Happ et al., "2-(1 H-1,2,3-Triazol-4-yl)-Pyridine Ligands as Alternatives to 2,2'-Bipyridines in Ruthenium(II) Complexes", Chem. Asian J., 2009, pp. 154-163, Dec. 23, 2008.
R. Hage et al., "Synthesis, separation, and NMR characterisation of the fac- and mer-isomers of tris(1-methyl-3-(pyridin-2-yl)-1,2,4-triazole)ruthenium(II) hexafluorophosphate", Inorganica Chimica Acta, vol. 118, Issue 1, Aug. 1, 1986, pp. 73-76.

(Continued)

*Primary Examiner* — Gurpreet Kaur
(74) *Attorney, Agent, or Firm* — LEX IP MEISTER, PLLC

(57) ABSTRACT

The present invention relates to: a transition metal complex having a bidentate ligand which includes pyrazole, triazole, tetrazole, oxadiazole, thiadiazole, or the like, wherein the transition metal complex can be used as an electron transfer mediator in a continuous blood glucose monitor and the like for measuring blood glucose concentration; and an oxidation-reduction polymer comprising same. The transition metal complex and the oxidation-reduction polymer can quickly and smoothly exchange electrons between an enzyme and an electrode, and thus can be effectively used in a continuous blood glucose biosensor.

15 Claims, 13 Drawing Sheets

(56) References Cited

OTHER PUBLICATIONS

P. J. Steel et al., "New ruthenium(II) complexes with pyridylpyrazole ligands. Photosubstitution and proton, carbon-13, and ruthenium-99 NMR structural studies", Inorg. Chem., 1983, 22, 1488 to 1493, May 1, 1983.
P. J. Steel et al., "Synthesis, Spectroscopy, and Electrochemistry of Homo- and Hetero-leptic Ruthenium(II) Complexes of New Pyrazole-containing Bidentate Ligands", Journal of the Chemical Society, Dalton Transactions: Inorganic Chemistry, 1990, 4,1389 to 1396.
Guillermo Orellana et al., "New binuclear heterocyclic ligands sharing an α-diimine moiety and their ruthenium(II) tris-chelates", Bull. Soc. Chim. Belg., vol. 97, Issue 10, 1988, pp. 731-742, Mar. 1, 1988.
Nicola Monti et al., "Antibacterial activity of a new class of tris homoleptic Ru (II)-complexes with alkyl-tetrazoles as diimine-type ligands", Applied Organometallic Chemistry, vol. 34, Issue 9, May 28, 2020, e5806, 1-14.
Registry (STN) [online], Oct. 8, 2004, [Search Date Aug. 21, 2024 ] CAS Registration No. 759423 to 84-2.
EPO, Search Report of EP 22792013.9 dated Oct. 8, 2024.
KIPO, PCT Search Report & Written Opinion of PCT/KR2022/005626 dated Aug. 8, 2022.
Nityananda Saha et al., "Magnetic and Spectroscopic Studies on some New Bis- and Tris-complexes of Iron(II) with 3, 5-Dimethyi-1- (2-pyridyi)pyrazole : indication of 5T2-1A1 Equilibrium", Journal of the indian chemicai society, Aug.-Oct. 1989, 521-524.
P. J. Steel et al., "New Ruthenium(II) Complexes with Pyridytpyrazote Ligands. Photosubstitution and 1H, 13C, and 99Ru NMR Structural Studies". Inorganic chemistry. 1983, 22, 1488-1493.
Hyun Yong Cho et al., "High-Throughput Synthesis of New Ni(II), Pd(II), and Co(II) Catalysts and Polymerization of Norbornene Utilizing the Self-Made Parallel Polymerization Reactor System," Macromolecular Rapid Communications, vol. 25, pp. 302-306, Jan. 2004, doi: https://doi.org/10.1002/marc.200300158.
Yun Chi et al., "Transition-metal phosphors with cyclometalating ligands: fundamentals and applications", Chem. Soc. Rev., 2010, vol. 39, pp. 638-655.

* cited by examiner

【Figure 1a】
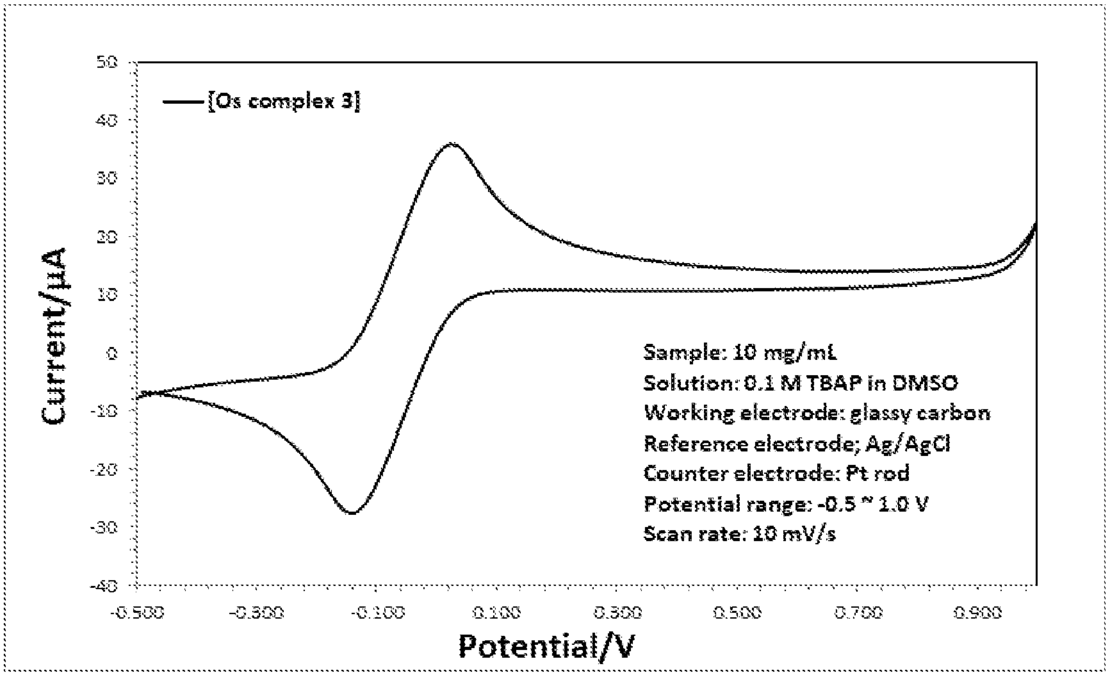
【Figure 1b】
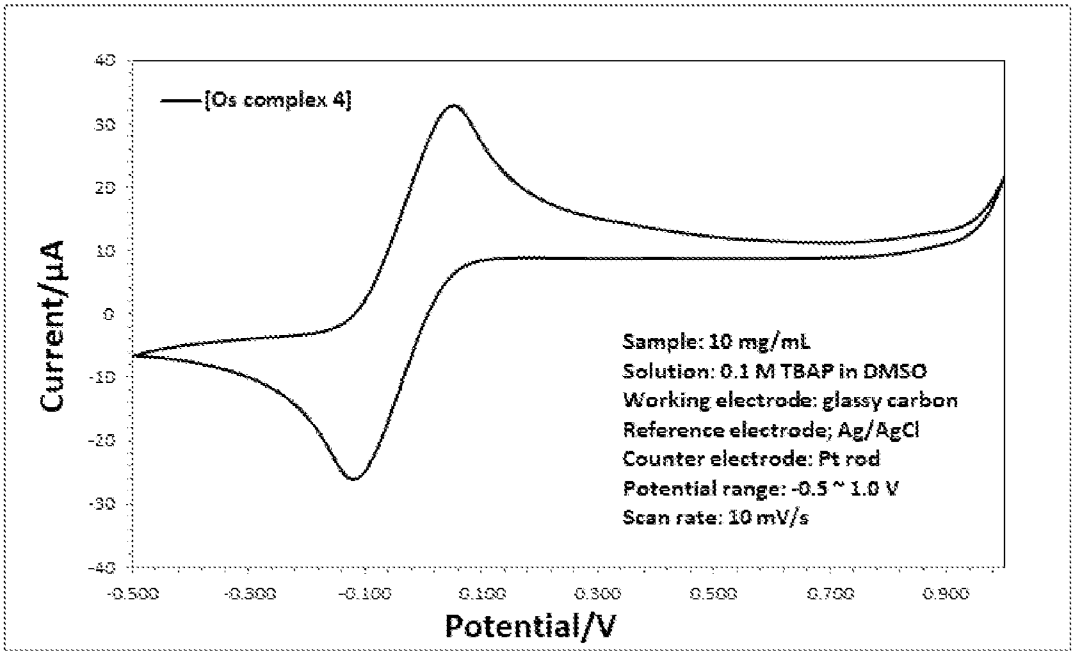

【Figure 1c】
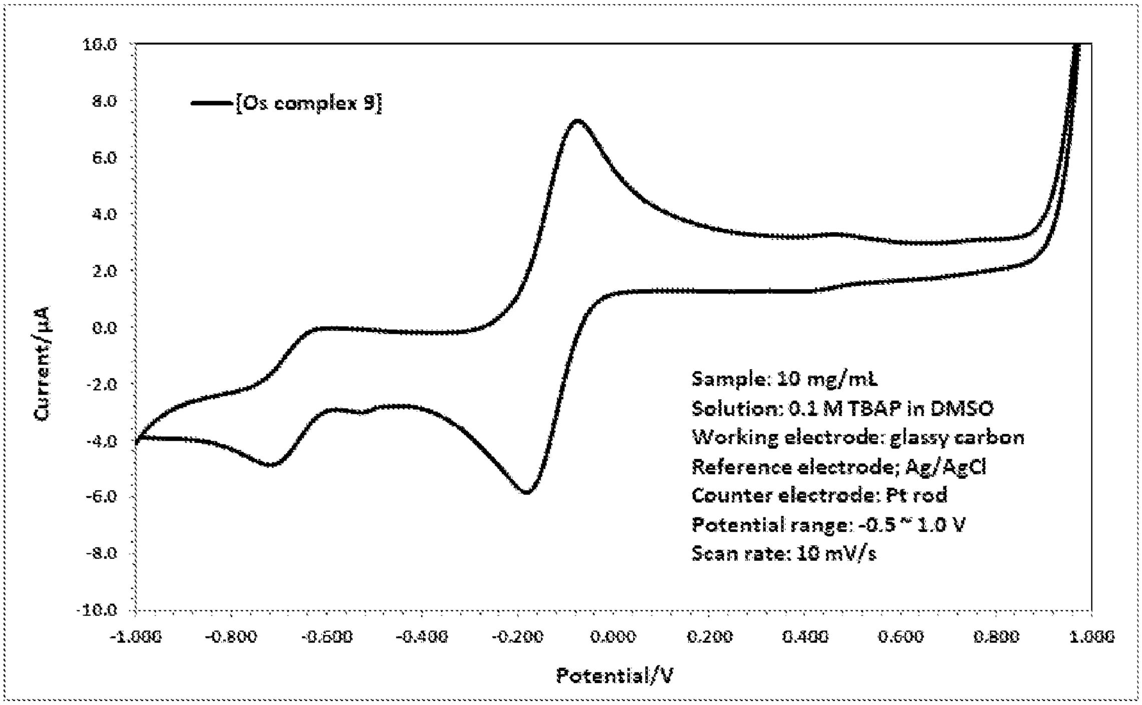
【Figure 1d】
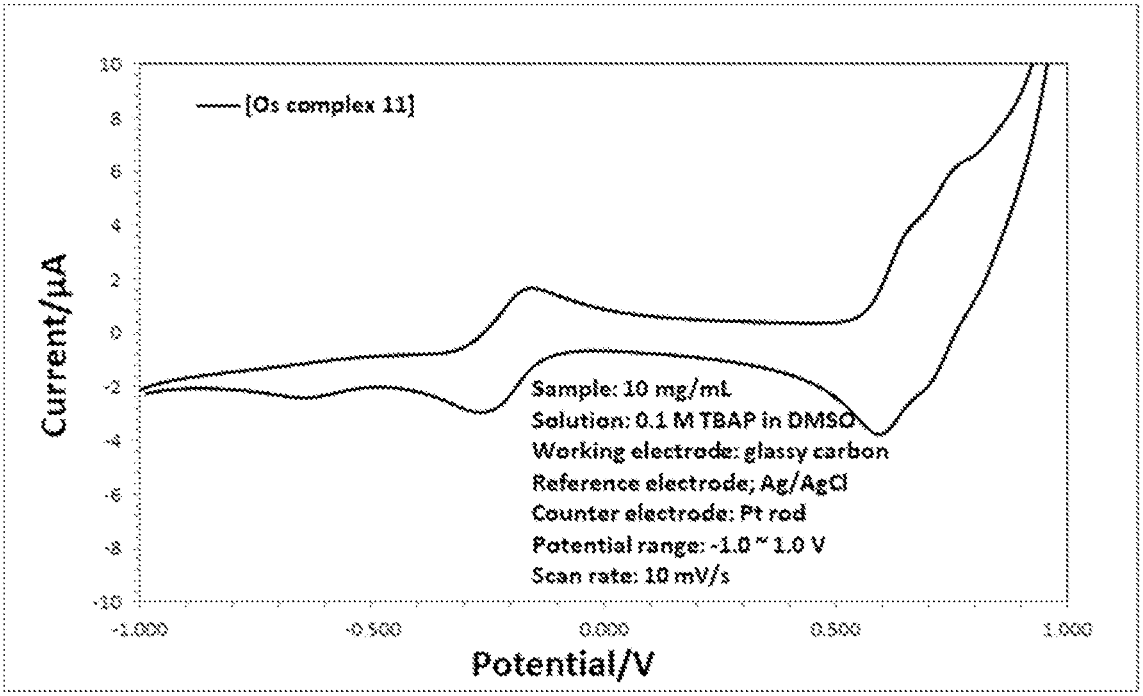

【Figure 1e】
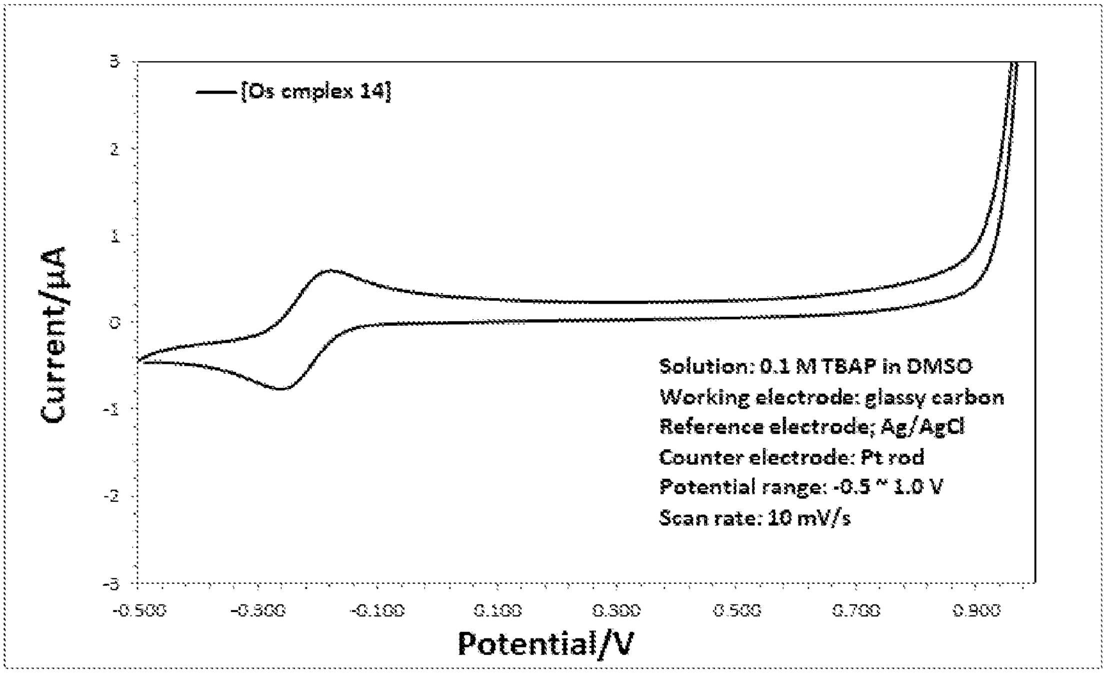
【Figure 1f】
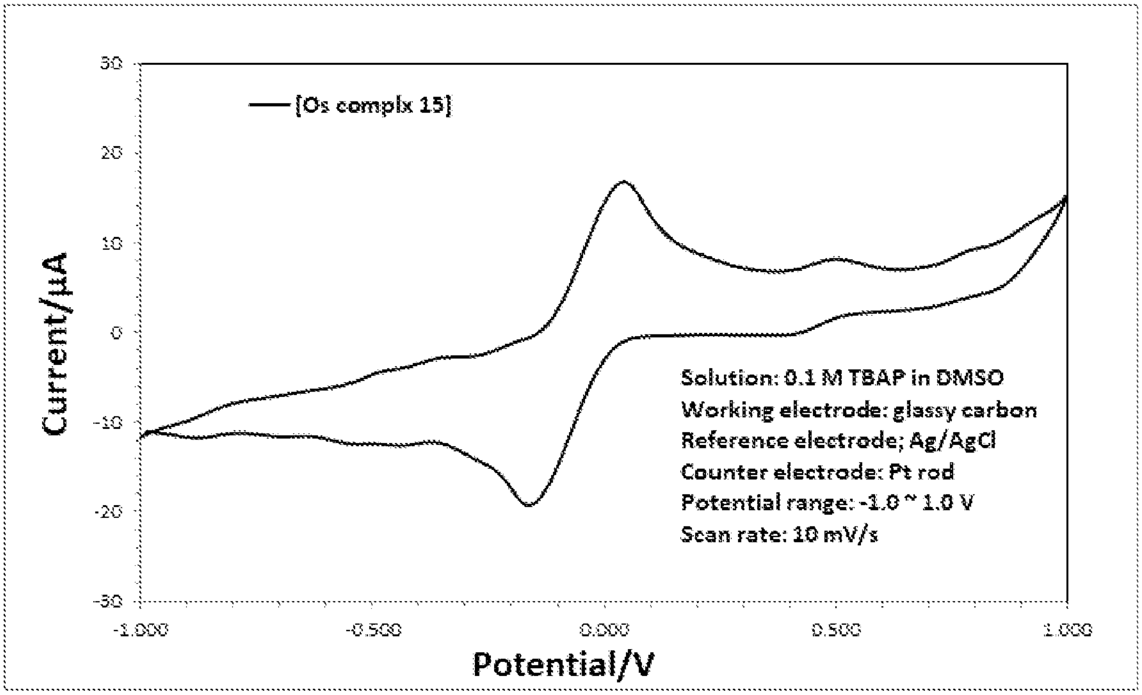

【Figure 1g】
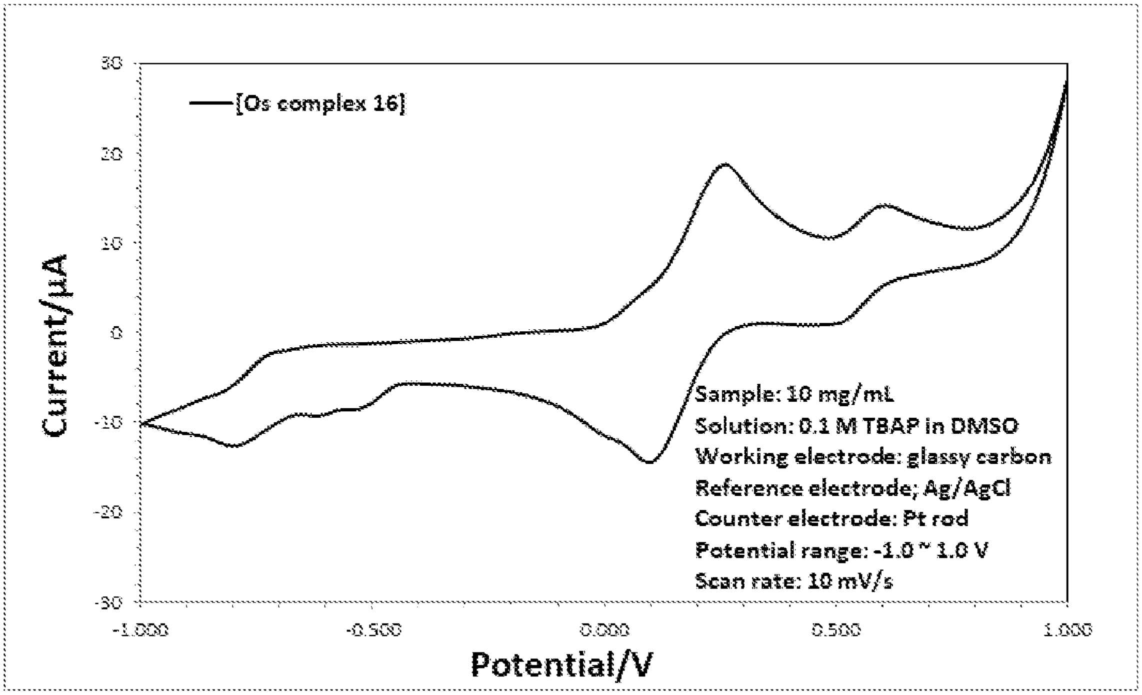
【Figure 1h】
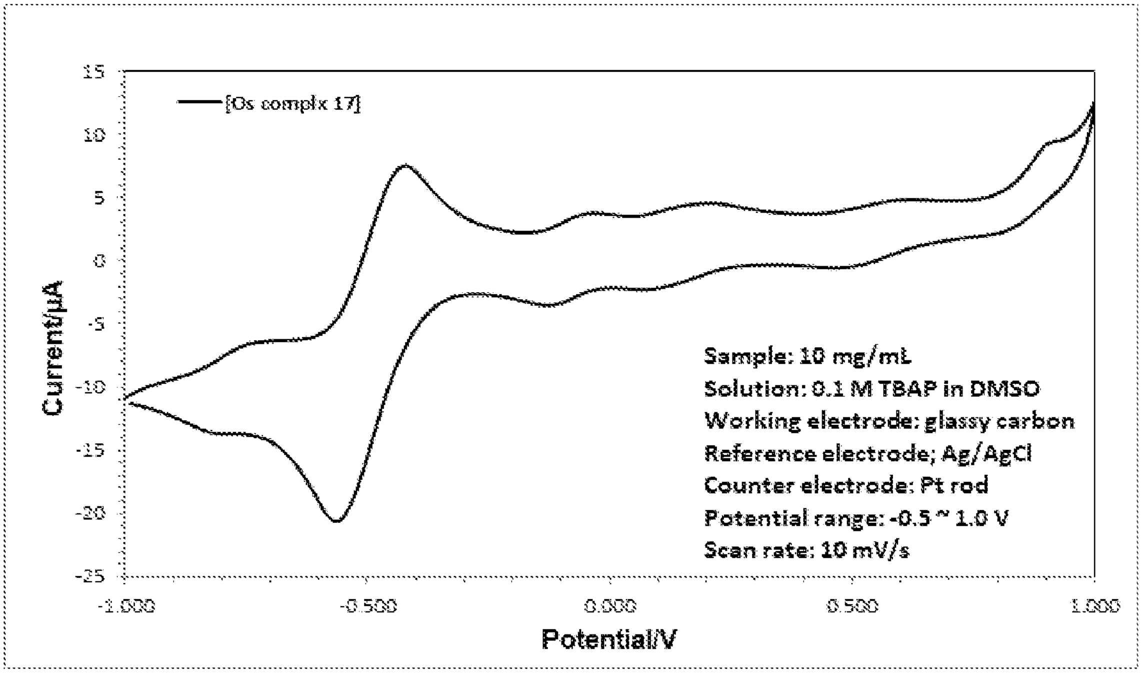

【Figure 1i】
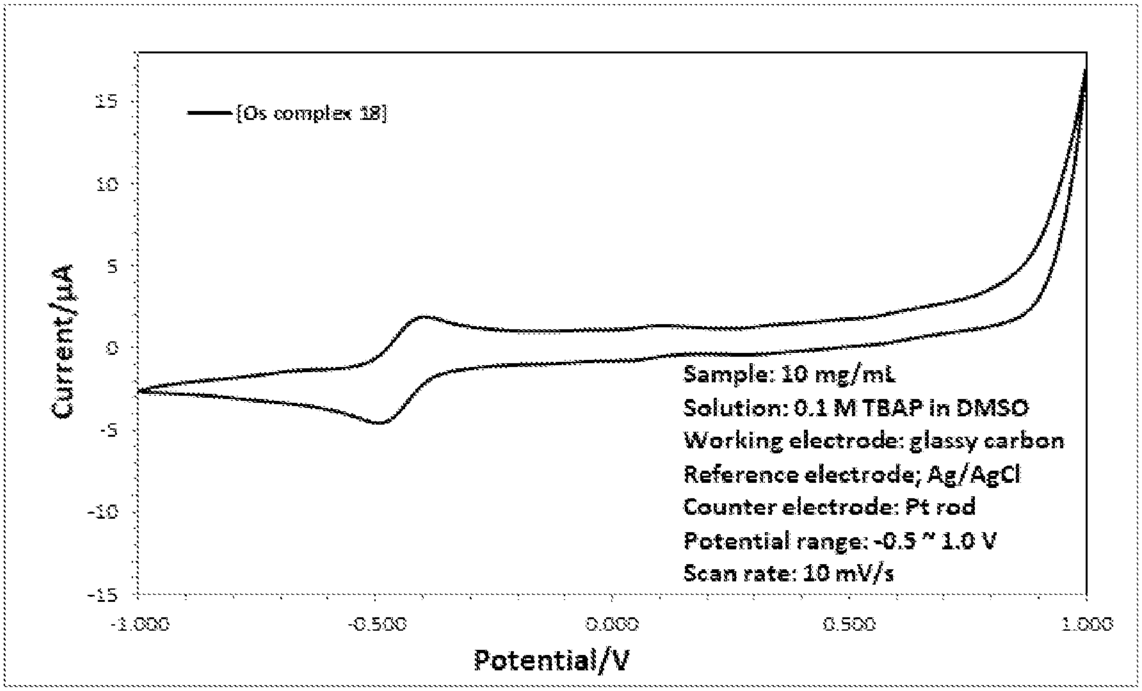
【Figure 1j】
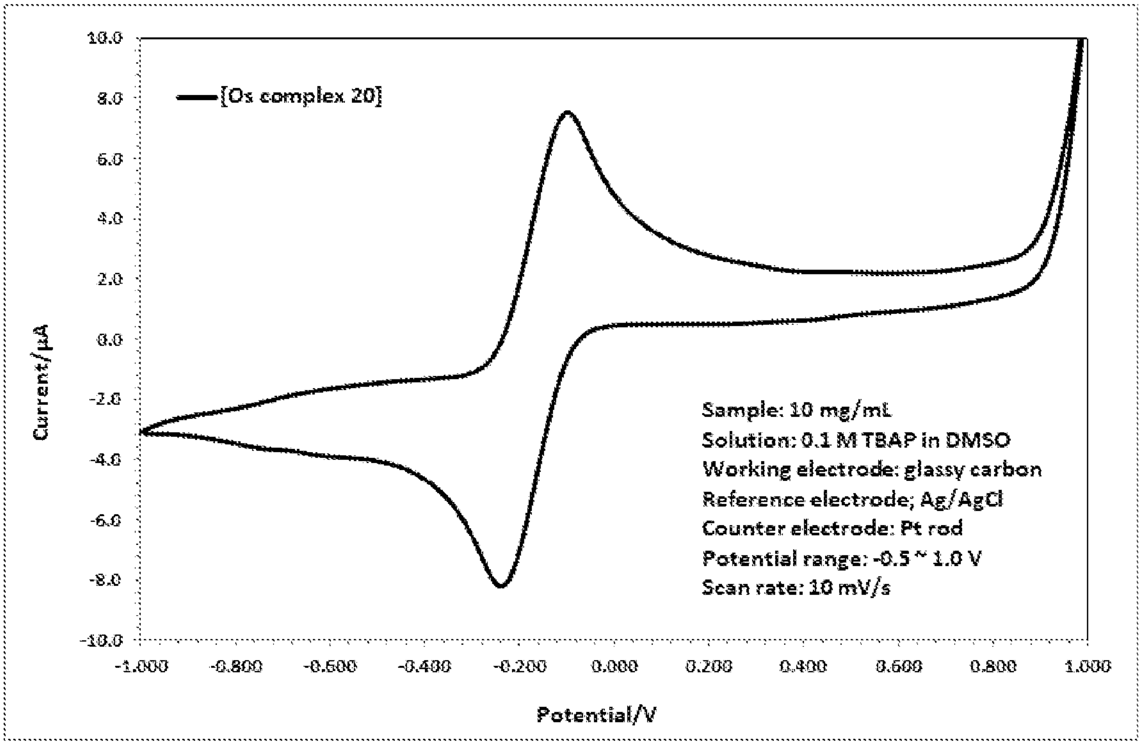

【Figure 1k】
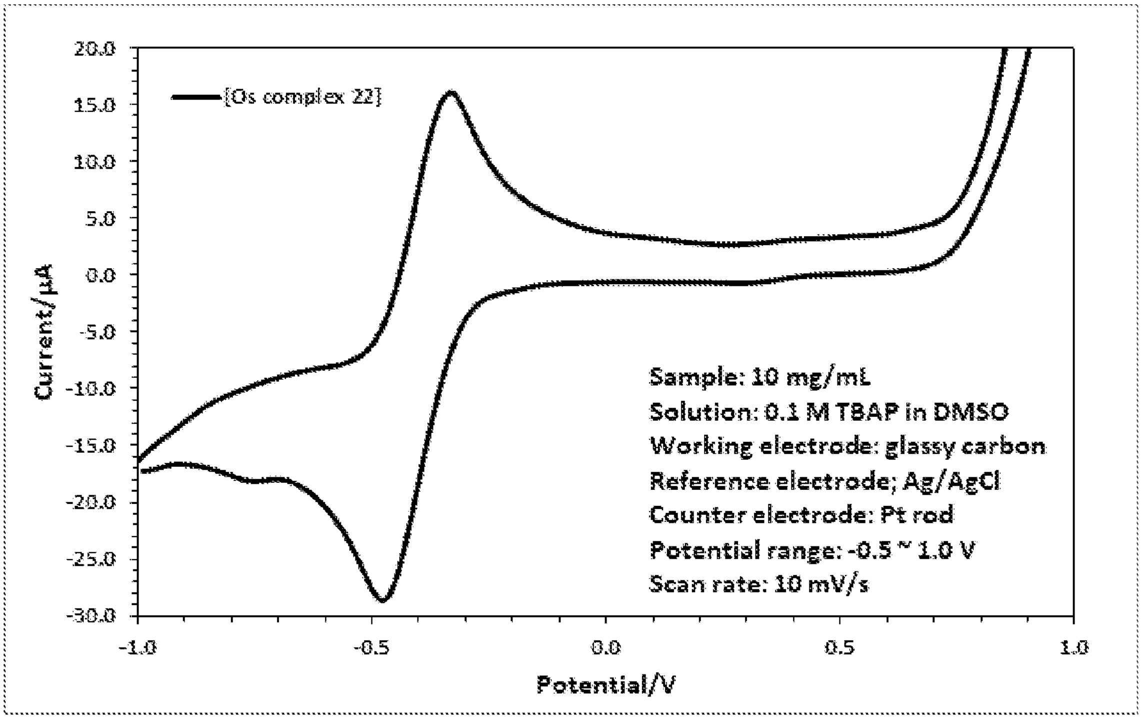
【Figure 1l】
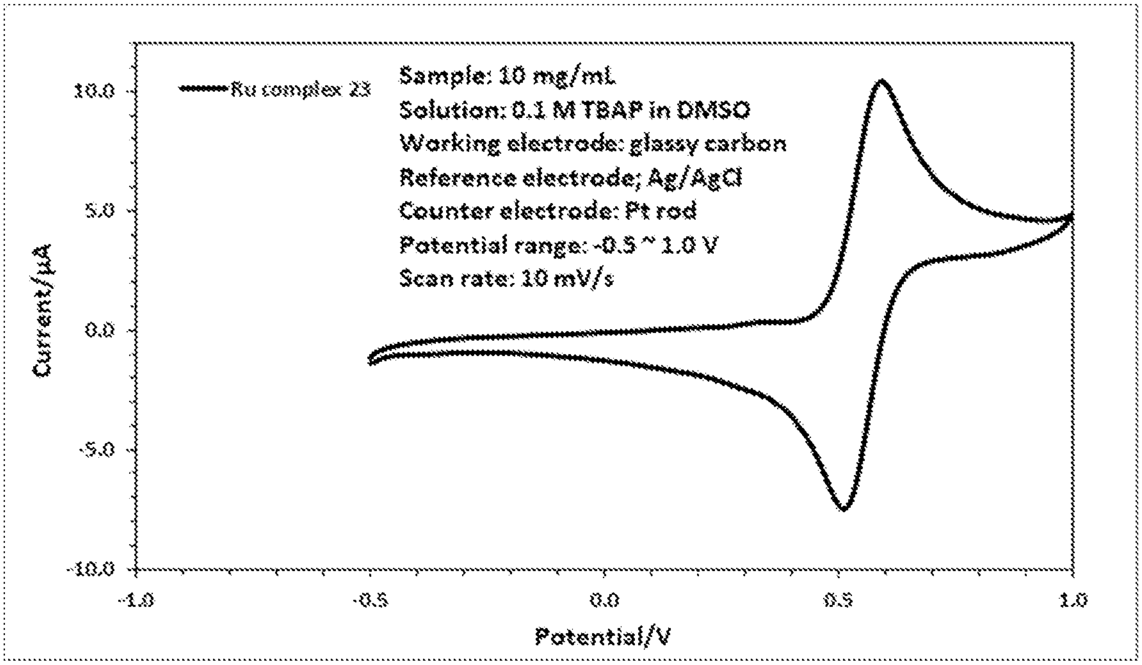

【Figure 1m】
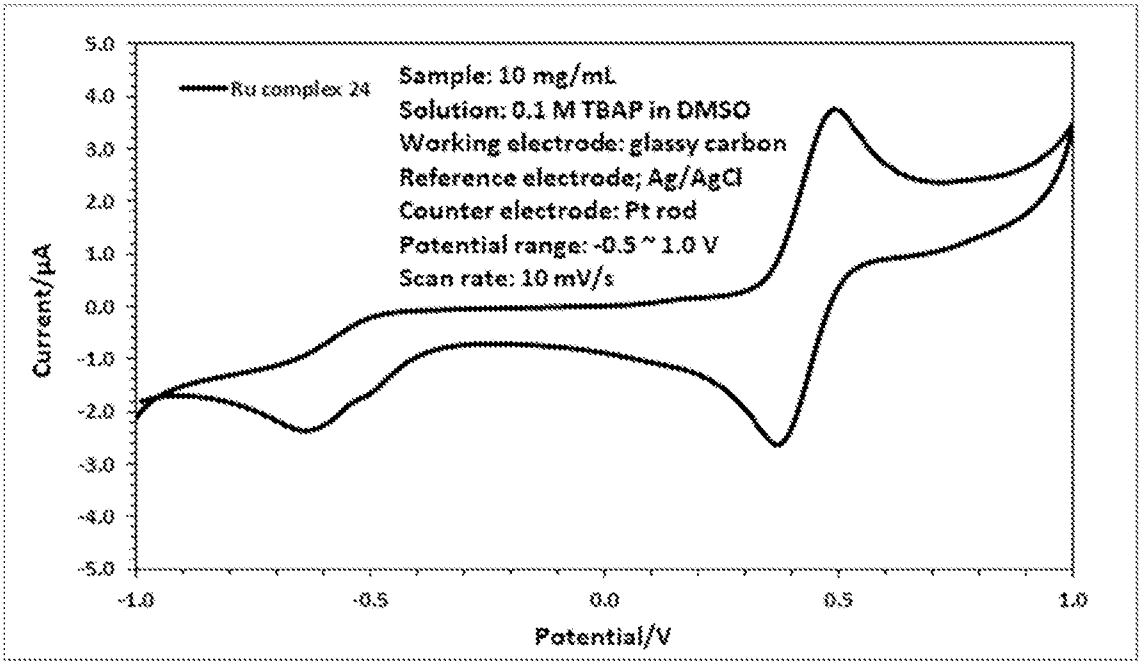
【Figure 1n】
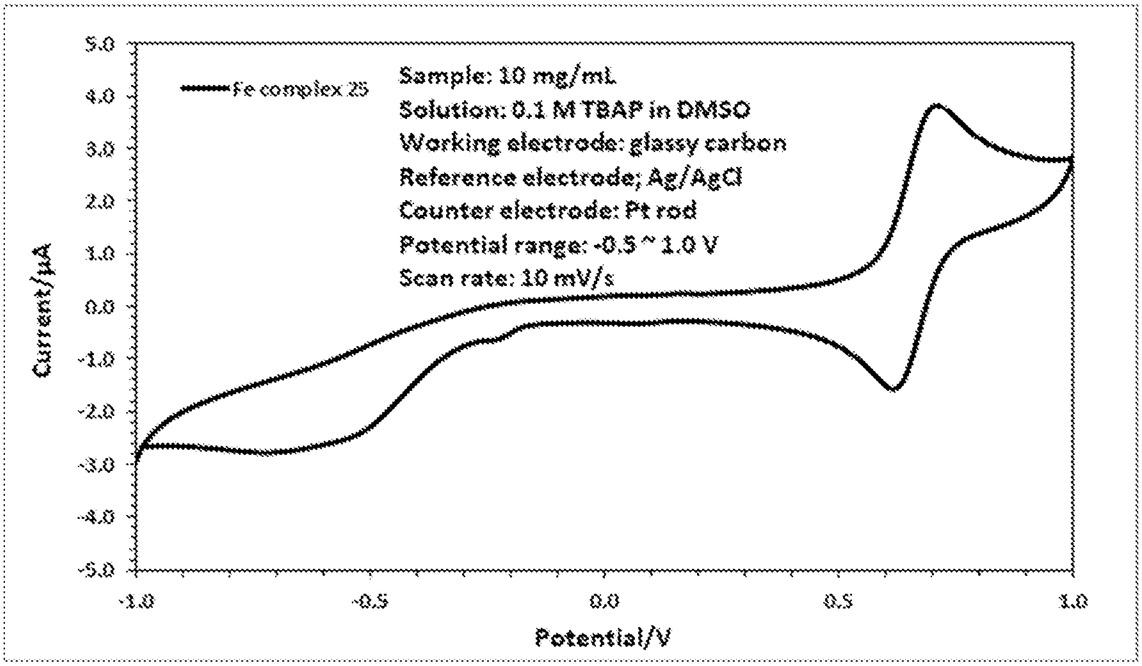

【Figure 1o】
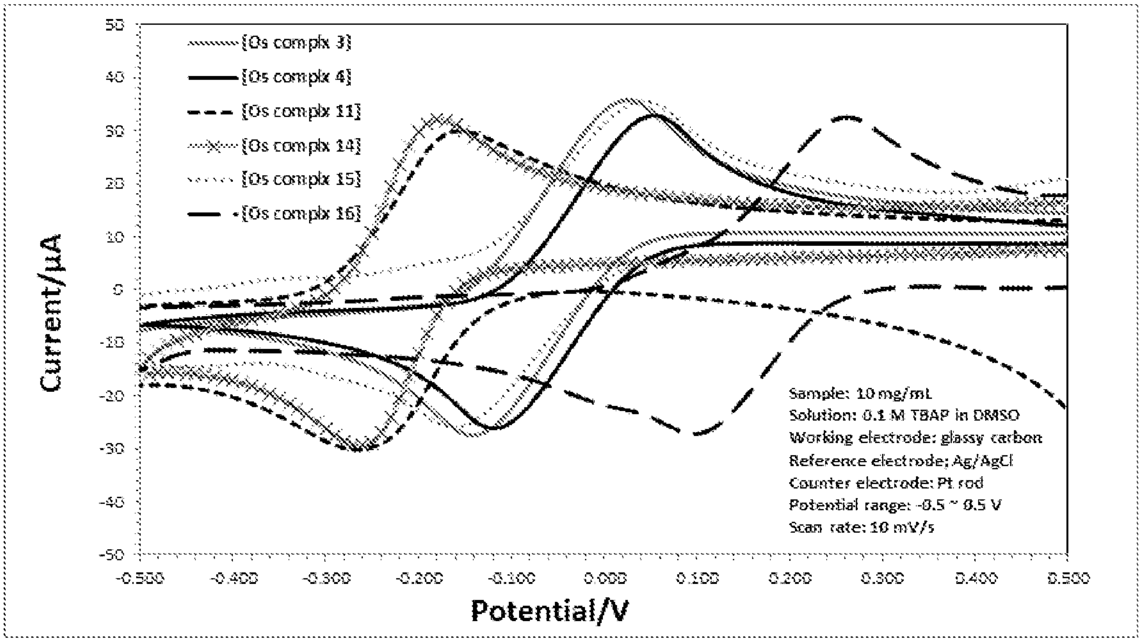

【Figure 2】
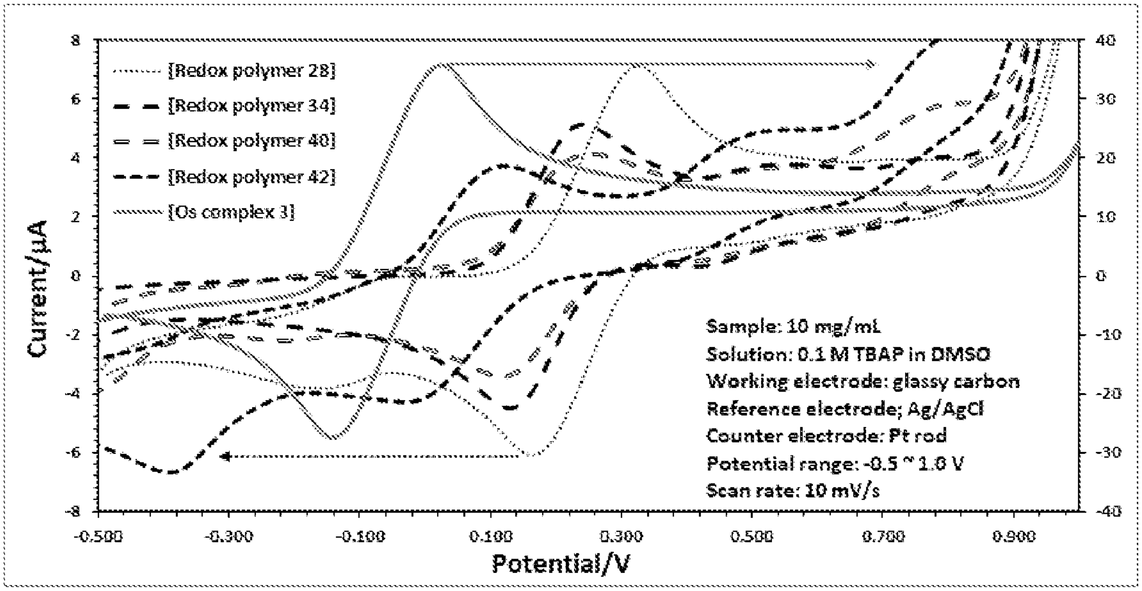
【Figure 3】
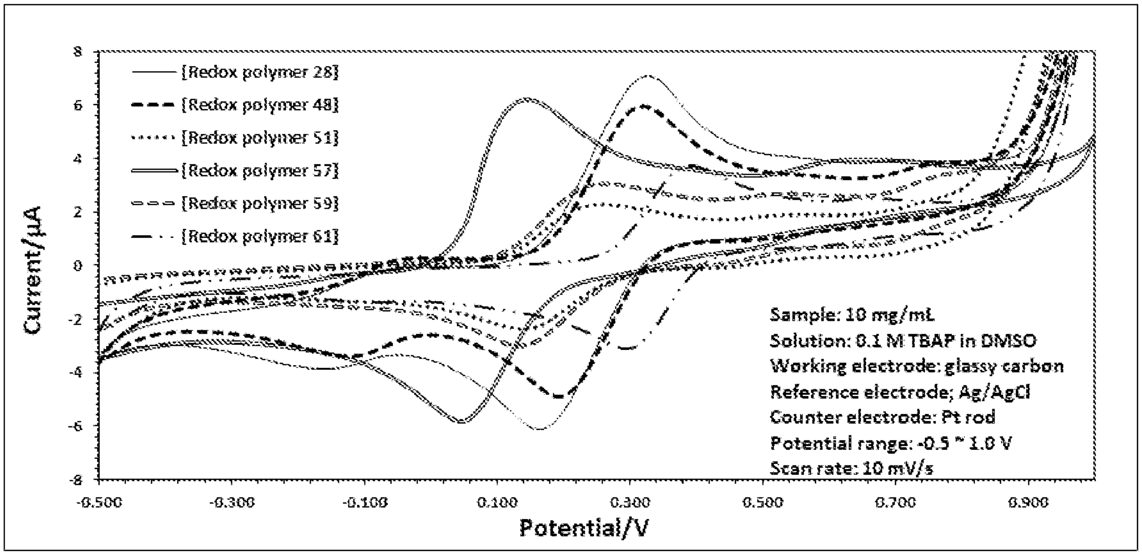

【Figure 4】
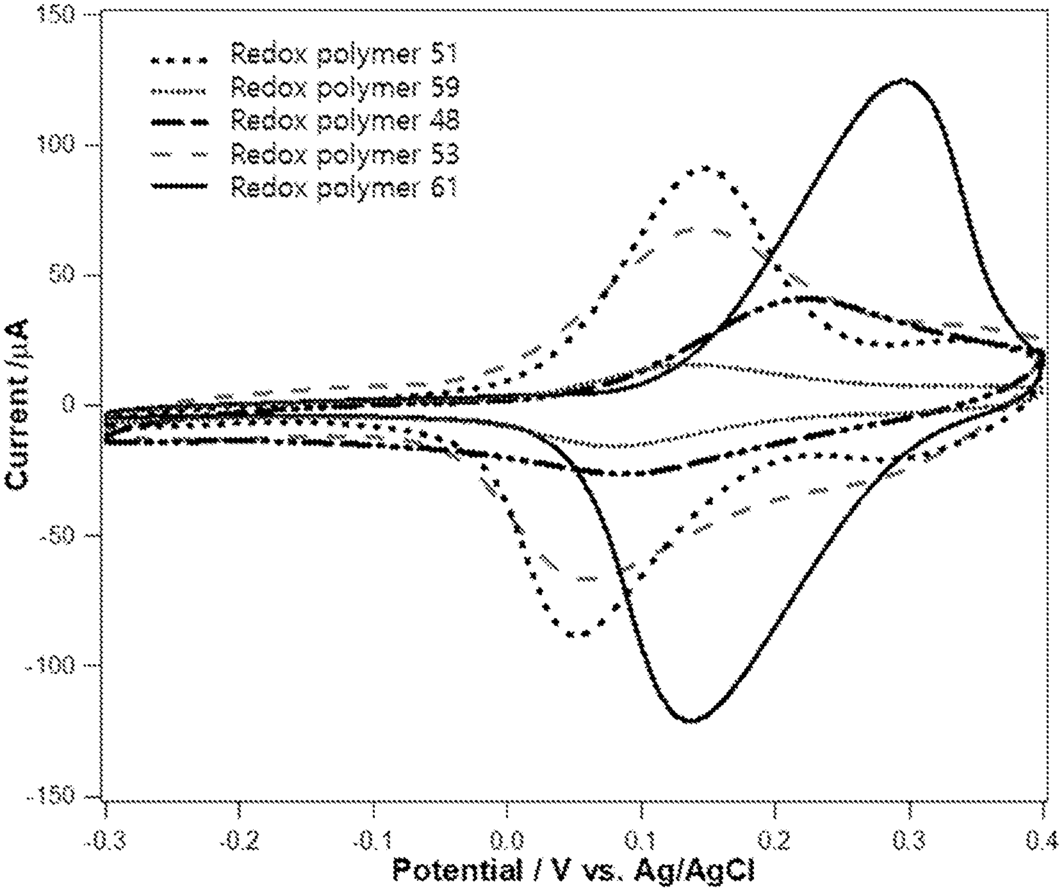

【Figure 5】
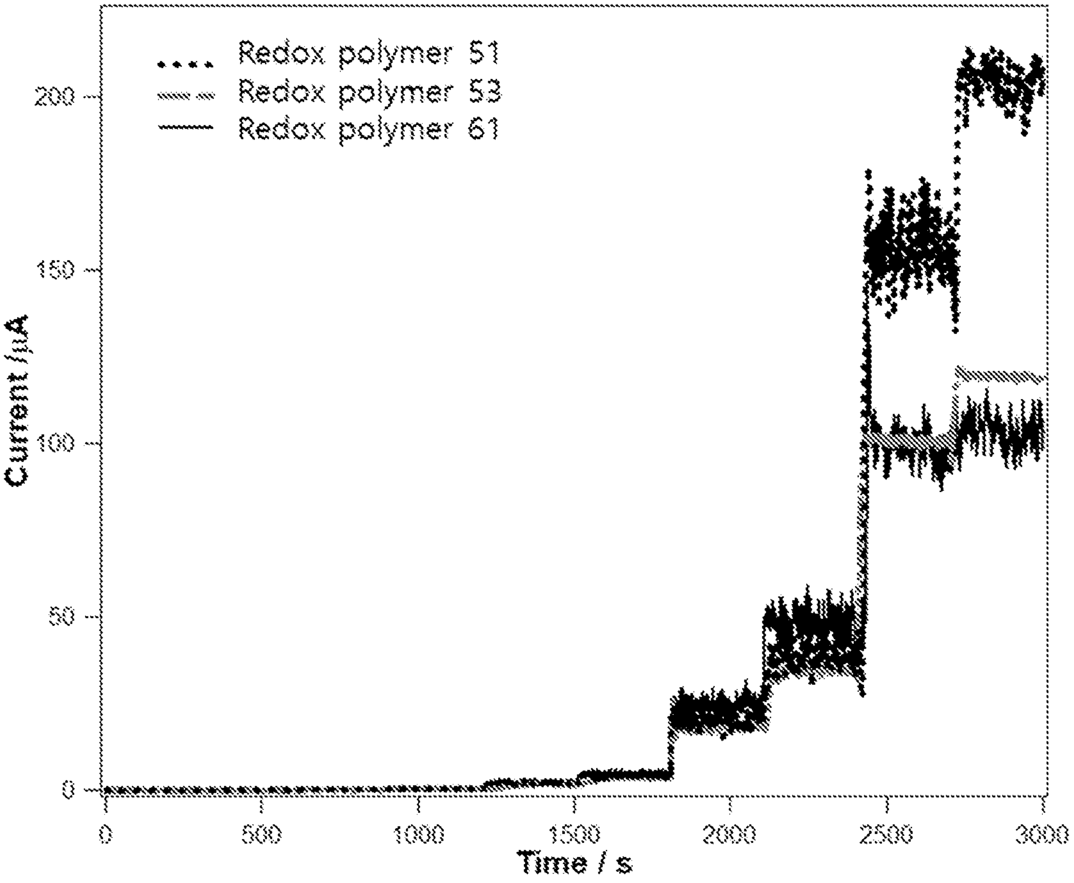

【Figure 6】
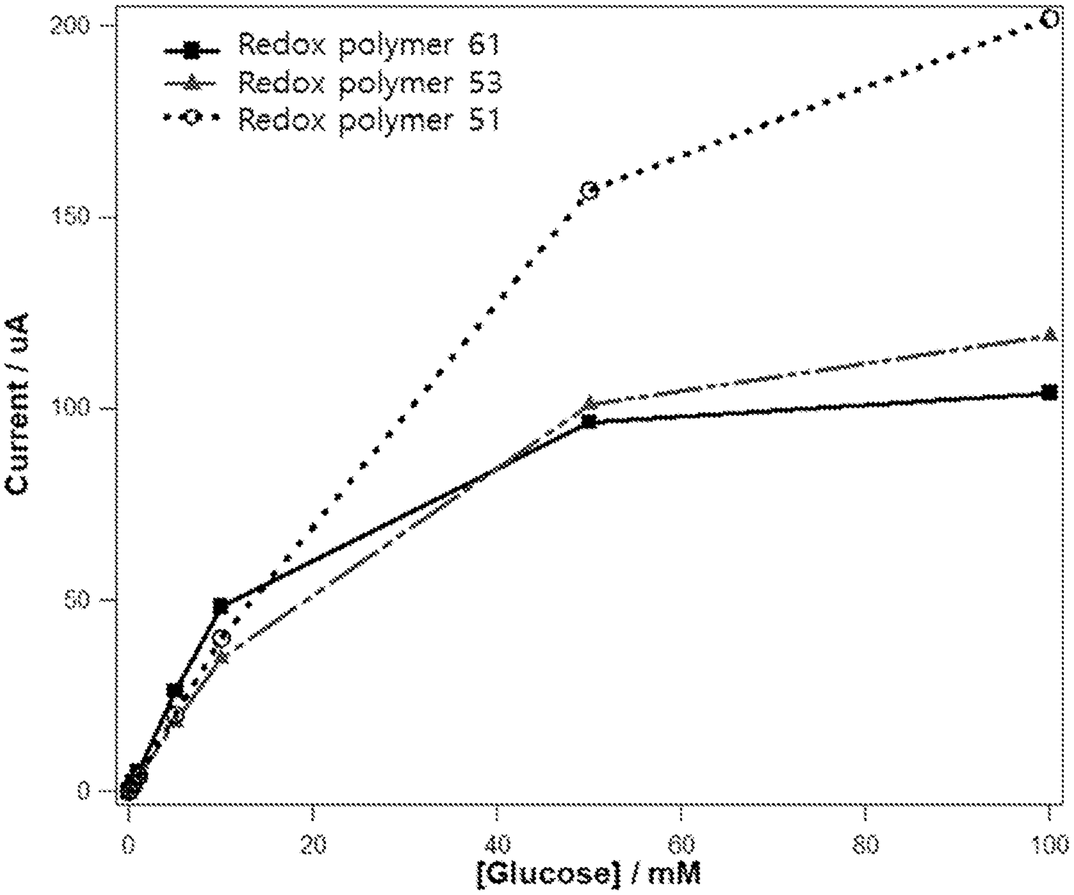

【Figure 7】
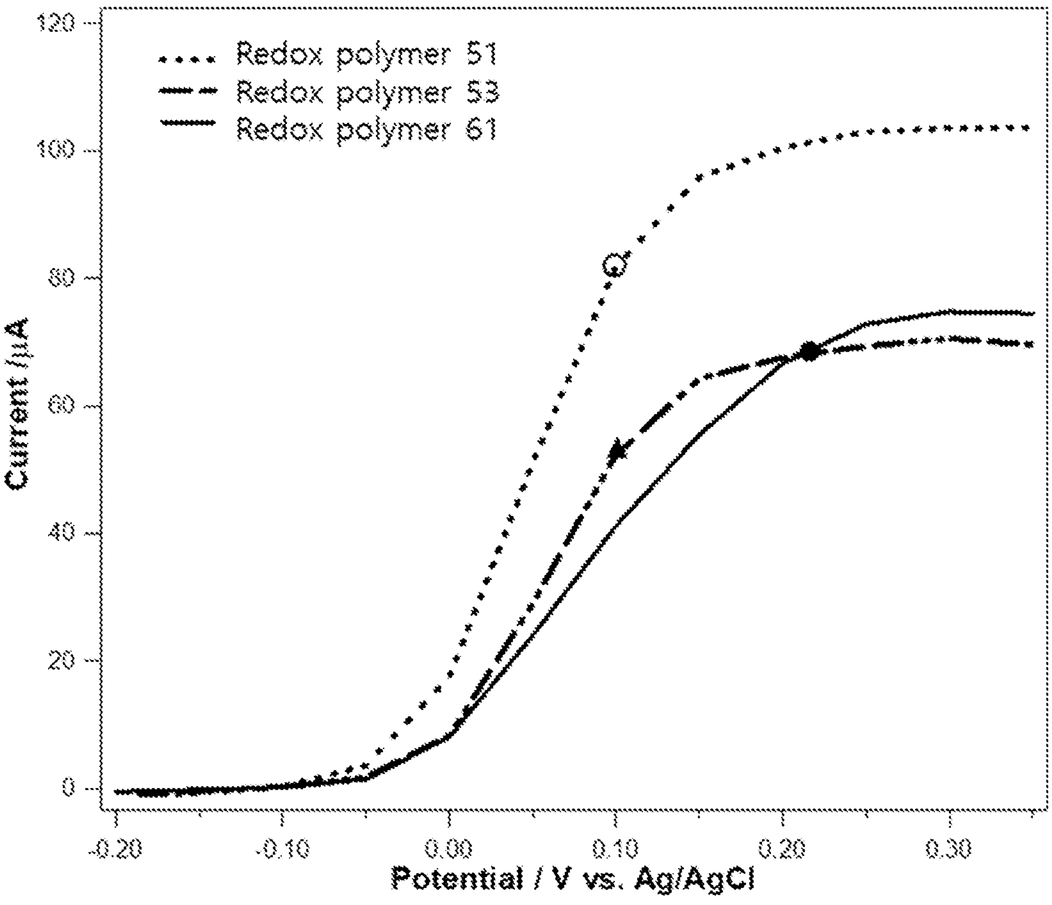

ELECTROCHEMICAL BIOSENSOR, OR SENSING MEMBRANE FOR ELECTROCHEMICAL BIOSENSOR CONTAINING TRANSITION METAL COMPLEX OR OXIDATION-REDUCTION POLYMER

TECHNICAL FIELD

The present invention relates to a transition metal complex having a bidentate ligand comprising pyrazole, triazole, tetrazole, oxadiazole or thiadiazole, or the like and an electrochemical biosensor using the same.

BACKGROUND ART

Recently, interest in development of biosensors for quantitative and qualitative analysis of target analytes has been increasing day by day from the medical field to the environment and food fields. In particular, biosensors using enzymes are chemical sensors used to selectively detect and measure chemical substances contained in a sample by using a functional substance of a living organism or a biological detection function in which a living organism such as microorganisms, and the like sensitively reacts with specific substances, and mostly, have been developed for a medical measurement use, and in addition, research is also being actively conducted in applications in the field of food engineering and environmental measurement.

Periodic measurement of blood glucose is very important in management of diabetes, and therefore, various blood glucose meters are being manufactured so that blood glucose can be easily measured using a portable measuring instrument. The principle of operation of such biosensors is based on an optical method or electrochemical method, and such electrochemical biosensors can reduce an effect by oxygen differently from biosensors by the conventional optical method, and have an advantage of being able to be used without separate retreatment of a sample, even though the sample is turbid. Therefore, various kinds of electrochemical biosensors having accuracy and precision are widely used.

Currently commercialized electrochemical blood glucose sensors mainly use enzyme electrodes, and more specifically, have a structure in which glucose oxidase is fixed by a chemical or physical method on an electrode that can convert electrical signals. Such electrochemical blood glucose sensors are based on the principle of measuring a glucose concentration in an analyte by measuring the current generated by transferring electrons generated when glucose in the analyte such as blood and the like is oxidized by an enzyme. In case of biosensors using enzyme electrodes, as the distance from the active center of the enzyme is too far, a problem that it is not easy to directly transfer electrons generated when a substrate is oxidized into an electrode is caused. Therefore, in order to easily perform this electron transfer reaction, an oxidation-reduction mediator, that is, an electron transfer mediator is necessarily required. Thus, what most significantly determines characteristics of an electrochemical biosensor measuring blood glucose is the type of enzyme and characteristics of the electron transfer mediator to be used.

In the development trend of blood-gathering blood glucose sensors, in order to block changes in measurement values due to a difference in oxygen partial pressure ($pO_2$) depending on blood (venous blood, capillary blood, etc.), it is converted to the use of GDH in which oxygen is excluded from an enzymatic reaction, instead of GOX, in which oxygen participates in the enzymatic reaction with glucose in blood, and in case of the electron transfer mediator, instead of ferricyanide with sensitive stability depending on the humidity, it has been replaced by organic compounds such as quinone derivatives (Phenanthroline quinone, Quineonediimine, etc.) with excellent stability depending on the temperature and humidity or organic metal compounds such as osmium complexes.

The most commonly used electron transfer mediator includes potassium ferricyanide [$K_3Fe(CN)_6$], and due to inexpensive price and great reactivity, it is useful for all sensors using FAD-GOX, PQQ-GDH or FAD-GDH. However, sensors using this electron transfer mediator have measurement errors due to interfering substances such as uric acid or gentisic acid present in blood, and are easy to be deteriorated by the temperature and humidity, so particular attention should be taken in manufacturing and storage, and there are difficulties of accurately detecting glucose at a low concentration due to changes in background current after long-term storage.

Hexamine ruthenium chloride [$Ru(NH_3)_6Cl_3$] has higher oxidation-reduction stability than ferricyanide, and therefore, biosensors using this electron transfer mediator have advantages of easy manufacturing and storage, and high stability due to small background current changes even during long-term storage, but there are disadvantages that it is difficult to manufacture it as a commercially useful sensor, since the reactivity does not match to use with FAD-GDH.

In addition, in using such biosensors, accurately obtaining rapid measurement values with a small amount of sample is a very important problem in terms of maximizing user convenience.

Therefore, development of a new electron transfer mediator which can achieve disadvantages of conventional electron transfer mediators and shortening of the measurement time is still required.

On the other hand, a continuous glucose monitoring (CGM) system is used to manage disease such as diabetes by continuously observing blood glucose, but in conventional enzyme sensors, collecting blood from a fingertip causes significant pain due to a needle during blood-gathering, so the measurement frequency is limited, and thus it cannot be used for such CGM. In order to solve these problems, improved versions of enzyme sensors that can be attached in the body and minimize invasion have been recently developed. In case of blood glucose monitoring enzyme sensors, since a part of the sensor enters the human body, problems caused by loss of the electron transfer mediator in the human body are to be prevented by fixing with a polymer such as polyvinyl pyridine or polyvinyl imidazole or the like, so that the electron transfer mediator comprising a transition metal and the like as described above is absorbed in the human body and causes toxicity and side effects.

As such, for development of a novel electron transfer mediator suitable for CGMS sensors, conventionally, an oxidation-reduction polymer of an enzyme sensor is prepared and used mainly by fixing a transition metal electron transfer mediator comprising bipyridine and bisimidazole ligands on the polymer skeleton. Under this background, the present inventors have confirmed that all of the above requirements can be satisfied when a transition metal complex having a bidentate ligand comprising a heterocyclic compound including pyrazole, triazole, tetrazole, oxadiazole or thiadiazole, or the like, in addition to bipyridine and bisimidazole ligands, thereby completing the present invention.

DISCLOSURE

Technical Problem

The present invention provides a transition metal complex or a salt compound thereof, which has a bidentate ligand comprising a heterocyclic structure such as pyrazole, triazole, tetrazole, oxadiazole or thiadiazole, or the like, in which synthesis of various derivatives and introduction of a functional group are easy.

In one embodiment, the transition metal complex may be a transition metal complex or a salt compound thereof having a bidentate ligand comprising pyridine; and one structure selected from the group consisting of pyrazole, triazole, tetrazole, oxadiazole and thiadiazole.

Another object of the present invention is to provide an oxidation-reduction polymer, comprising the transition metal complex or salt compound thereof.

Other object of the present invention is to provide the transition metal complex or salt compound thereof and/or an oxidation-reduction polymer comprising the same to a device.

In one embodiment, the device may be a device for an electron transfer mediator, specifically, an electrochemical biosensor. In one embodiment, the device may be insertable into the body. In one embodiment, the electrochemical biosensor may be a blood glucose sensor.

Other object of the present invention is to provide a sensing membrane for an electrochemical biosensor comprising an enzyme capable of oxidizing-reducing a liquid biological sample; and the transition metal complex or salt compound thereof and/or an oxidation-reduction polymer comprising the same.

Technical Solution

In one aspect, the present invention provides a transition metal complex or a salt compound thereof, having a bidentate (hereinafter, also called "bidentate") comprising pyridine; and one structure selected from the group consisting of pyrazole, triazole, tetrazole, oxadiazole and thiadiazole.

Specifically, the transition metal complex may be a compound of the following Chemical formula 1.

[Chemical formula 1]

$$[M(L)_a(X_1)_b]^c d(X_2)$$

in the formula,

M is one kind transition metal selected from the group consisting of Fe, Ru, and Os, and L is a bidentate ligand comprising pyridine; and one structure selected from the group consisting of pyrazole, triazole, tetrazole, oxadiazole and thiadiazole, and a is 2 or 3, and $X_1$ is one kind halogen atom selected from the group consisting of F, Cl, Br and I, and b is 0, 1, or 2, and c is an integer selected from 1 to 3 (for example, 1, 2, or 3), and $X_2$ is one kind counter ion selected from the group consisting of F, Cl, Br, I and $PF_6$, and d is 0, 1, or 2.

Hereinafter, the present invention will be described in detail.

All technical terms used in the present invention, unless otherwise defined, are used with the same meaning as commonly understood by those skilled in the art related to the present invention. In addition, in the present description, preferable methods or samples are described, but those similar or equivalent thereto are included in the scope of the present invention. Furthermore, numerical values described in the present description are considered to include the meaning of "about" even if not specified. The contents of all publications described in the present description as references are incorporated in the present description by reference in their entirety.

Definitions of residues used in the present description will be described in detail. Unless otherwise specified, each residue has the following definition and is used with the same meaning as commonly understood by those skilled in the art.

In the present invention, "halo" or "halogen" means for example, fluoro, chloro, bromo and iodo.

In the present description, "alkyl" means an aliphatic hydrocarbon radical, and includes all linear or branched hydrocarbon radicals. For example, the aliphatic hydrocarbon having 1 to 6 carbon atoms, includes methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl, but not limited thereto. Unless otherwise defined, the alkyl may mean alkyl having 1 to 6 carbon atoms, 1 to 5 carbon atoms, 1 to 4 carbon atoms, 1 to 3 carbon atoms, 1 to 2 carbon atoms, 2 to 6 carbon atoms, 2 to 5 carbon atoms, 2 to 4 carbon atoms, 2 to 3 carbon atoms, 3 to 6 carbon atoms, 3 to 5 carbon atoms, 3 to 4 carbon atoms, 1 carbon atom, 2 carbon atoms, 3 carbon atoms, 4 carbon atoms, 5 carbon atoms, or 6 carbon atoms.

In the present description, "alkoxy" represents a —O-alkyl or alkyl-O— group, and herein, the alkyl group is the same as defined above. For example, those such as methoxy, ethoxy, n-propoxy, n-butoxy, and t-butoxy are included, but not limited thereto. The alkoxy group may be substituted or unsubstituted with at least one appropriate group.

In the present description, the term, "hydroxy" or "hydroxyl" alone or combined with another term, means —OH.

In the present description, "amino" represents $—NH_2$, and "nitro" represents $—NO_2$.

In the present description, "aryl" refers to a monovalent aromatic ring having for example, 6 to 20 carbon atoms, 6 to 12 carbon atoms, or 6 to 10 carbon atoms, induced by removing one hydrogen atom in one carbon atom in a parent aromatic ring system. The aryl may comprise a bicyclic radical comprising an aromatic ring fused with a saturated or partially unsaturated ring. An exemplary aryl group may include radicals induced from benzenes (phenyl), substituted phenyl, biphenyl, naphthyl, tetrahydronaphthyl, fluorenyl, toluyl, naphthalenyl, anthracenyl, indenyl, indanyl, and the like, but not limited thereto. The aryl group may be substituted or unsubstituted with at least one appropriate group.

In the present description, "substitution" may be, unless particularly mentioned, that at least one hydrogen atom is one kind to three kinds selected from the group consisting of halogen atoms (for example, F, Cl, Br, or I), cyano group, hydroxyl group, thiol group, nitro group, amino group, imino group, azido group, amidino group, hydrazine group, hydrazono group, oxo group, carbonyl group, carbamyl group, ester group, ether group, carboxyl group, or salts thereof, sulfonic acid or salts thereof, phosphoric acid or salts thereof, alkyl group having 1 to 6 carbon atoms, haloalkyl group having 1 to 6 carbon atoms, alkenyl group having 2 to 6 carbon atoms, haloalkenyl group having 2 to 6 carbon atoms, alkylnyl group having 2 to 6 carbon atoms, haloalkylnyl group having 2 to 6 carbon atoms, alkoxy group having 1 to 6 carbon atoms, haloalkoxy group having 1 to 6 carbon atoms, alkylthio group having 1 to 6 carbon atoms, cycloalkyl group having 3 to 20 carbon atoms, 5-membered to 12-membered heterocycloalkyl group, 5-membered to 12-membered heteroaryl group, aryl group having 6 to 10 carbon atoms, aryloxy group having 6 to 10 carbon atoms and arylthiol group having 6 to 10 carbon atoms.

The transition metal complex provided in the present description, may be a compound of the following Chemical formula 1.

[Chemical formula 1]

$$[M(L)_a(X_1)_b]^c d(X_2)$$

in the formula,

M is one kind transition metal selected from the group consisting of Fe, Ru, and Os, and L is a bidentate ligand comprising pyridine; and one structure selected from the group consisting of pyrazole, triazole, tetrazole, oxadiazole and thiadiazole, and a is 2 or 3, and $X_1$ is one kind halogen atom selected from the group consisting of F, Cl, Br and I, and b is 0, 1, or 2, and c is an integer selected from 1 to 3 (for example, 1, 2, or 3), and $X_2$ is one kind counter ion selected from the group consisting of F, Cl, Br, I and $PF_6$, and d is 0, 1, or 2.

The pyridine may be unsubstituted, or substituted with at least one kind (for example, 1 to 4, 1, 2, 3, or 4) selected from the group consisting of $C_{1-4}$ alkyl group, $C_{1-4}$ alkoxy group, —(CH2)-O—$C_{1-4}$ alkyl group, —(CH2CH2)-O—$C_{1-4}$ alkyl group, and $C_{1-4}$ alkylamino group.

The pyrazole, triazole, tetrazole, oxadiazole, or thiadiazole may be each unsubstituted, or substituted with at least one kind (for example, 1 to 3, 1, 2, or 3) selected from the group consisting of $C_{1-4}$ alkyl group, $C_{1-4}$ alkoxy group, —(CH2)-O—$C_{1-4}$ alkyl group, —(CH2CH2)-O—$C_{1-4}$ alkyl group,

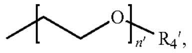

and $C_{1-4}$ alkylamino group.

The $R'_4$ may be hydrogen or substituted or unsubstituted $C_{1-4}$ alkyl, and the n' may be an integer selected from 1 to 4, for example, 1, 2, 3, or 4.

The $C_{1-4}$ alkyl group, alkoxy group, or alkylamino group may mean an alkyl group, alkoxy group, or alkylamino group having 1 to 4, 1 to 3, 1 to 2, 2 to 4, 2 to 4, 3 to 4, 1, 2, 3, or 4 carbon atoms.

The $C_{1-4}$ alkyl group, $C_{1-4}$ alkoxy group, —(CH2)-O—$C_{1-4}$ alkyl group, —(CH2CH2)-O—$C_{1-4}$ alkyl group, or $C_{1-4}$ alkylamino group may be unsubstituted, or substituted. In the substituted $C_{1-4}$ alkyl group, $C_{1-4}$ alkoxy group, —(CH2)-O—$C_{1-4}$ alkyl group, —(CH2CH2)-O—$C_{1-4}$ alkyl group, or $C_{1-4}$ alkylamino group, a hydrogen atom may be substituted with a halogen atom of F, Cl, Br or I, cyano group, hydroxy group, thiol group, nitro group, amino group, imino group, azido group, amidino group, hydrazine group, hydrazono group, oxo group, carbonyl group, carbamyl group, ester group, ether group, carboxyl group or salt thereof, sulfonic acid group or salt thereof, or phosphoric acid or salt thereof.

Specifically, the transition metal complex may be a compound of the following Chemical formula 2.

[Chemical formula 2]

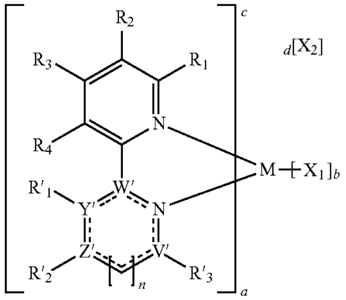

in the formula, $R^1$, $R^2$, $R^3$, and $R^4$ are each independently hydrogen, $C_{1-4}$ alkyl group, $C_{1-4}$ alkoxy group, (CH2)-O—$C_{1-4}$ alkyl group, (CH2CH2)-O—$C_{1-4}$ alkyl group, or $C_{1-4}$ alkylamino group, and n is 0, and at least one of W', Y', Z', and V is nitrogen (N), and W is nitrogen (N) or carbon (C), and Y', Z', and V' are each independently nitrogen (N), sulfur (S), oxygen (O), or carbon (C), and $R'_1$, $R'_2$, and $R'_3$ are each independently hydrogen, $C_{1-4}$ alkyl group, $C_{1-4}$ alkoxy group, —(CH2)-O—$C_{1-4}$ alkyl group, —(CH2CH2)-O—$C_{1-4}$ alkyl group,

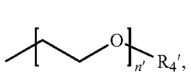

or $C_{1-4}$ alkylamino group, and the dotted line means a bond or no bond, and the $R'_4$ may be hydrogen or substituted or unsubstituted $C_{1-4}$ alkyl, and the n' may be an integer selected from 1 to 4, for example, 1, 2, 3, or 4, and M, a, $X_1$, b, c, $X_2$ and d are as defined in Chemical formula 1 above.

The $C_{1-4}$ alkyl group, $C_{1-4}$ alkoxy group, —(CH2)-O—$C_{1-4}$ alkyl group, —(CH2CH2)-O—$C_{1-4}$ alkyl group, or $C_{1-4}$ alkylamino group may be unsubstituted, or substituted, respectively, and the substituted case is as described above.

Specifically, the transition metal complex may be a compound selected from the following Chemical formula 3 to Chemical formula 25.

[Chemical formula 3]
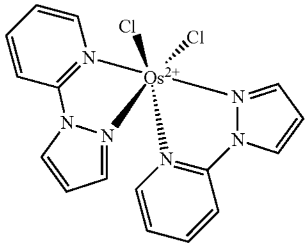
,
[Chemical formuula 4]
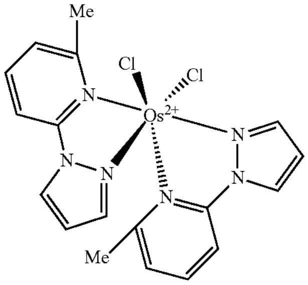
,
[Chemical formula 5]
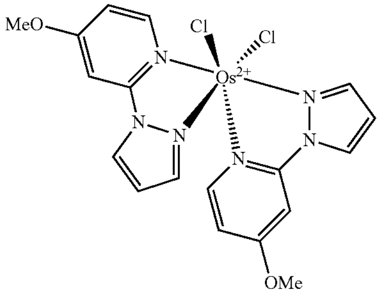
,
[Chemical formula 6]
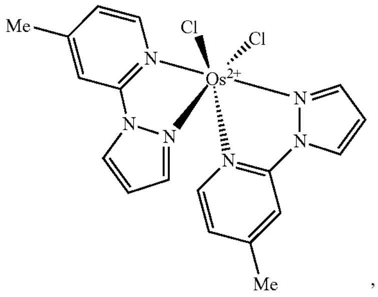
,
[Chemical formula 7]
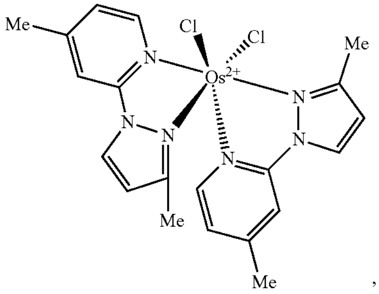
,
-continued
[Chemical formula 8]
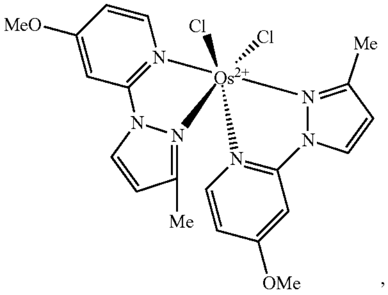
,
[Chemical formula 9]
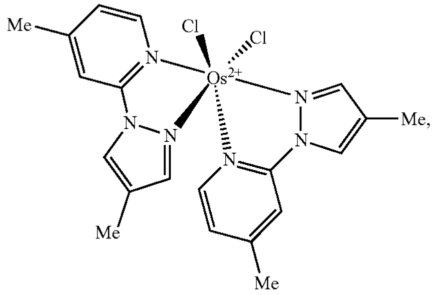
[Chemical formula 10]
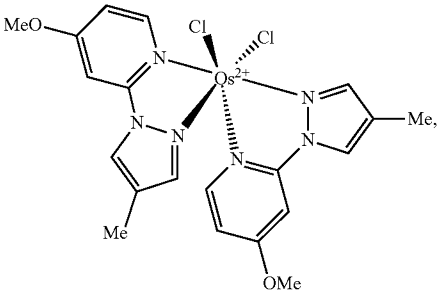
[Chemical formula 11]
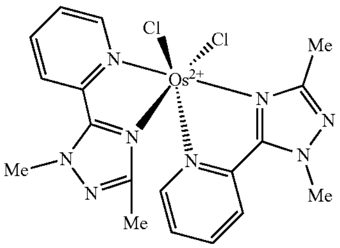
,
[Chemical formula 12]
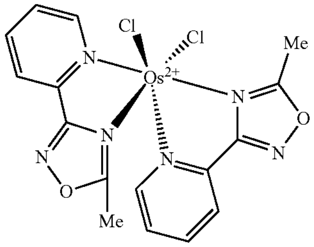
, -continued
[Chemical formula 13]
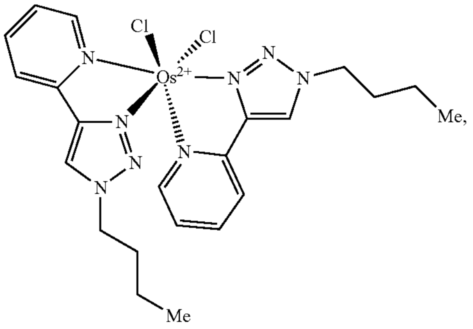
[Chemical formula 14]
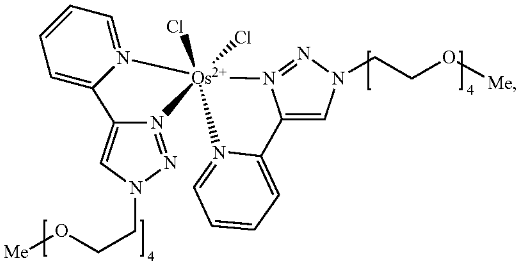
[Chemical formula 15]
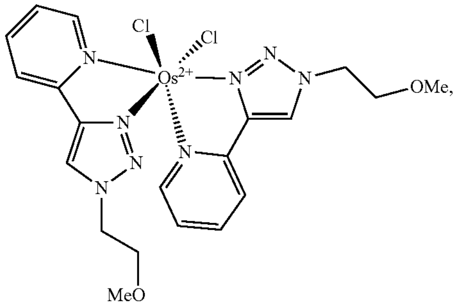
[Chemical formula 16]
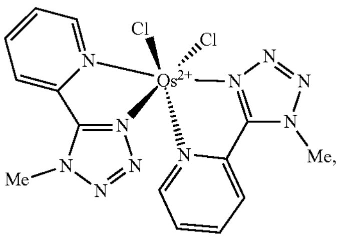
[Chemical formula 17]
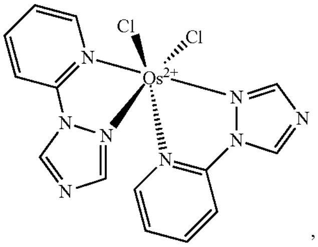
,
-continued
[Chemical formula 18]
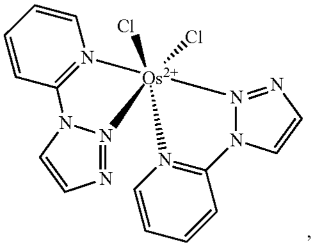
,
[Chemical formula 19]
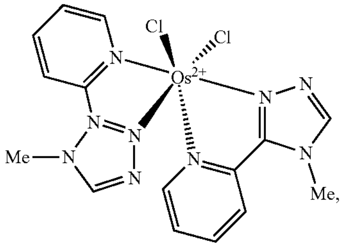
[Chemical formula 20]
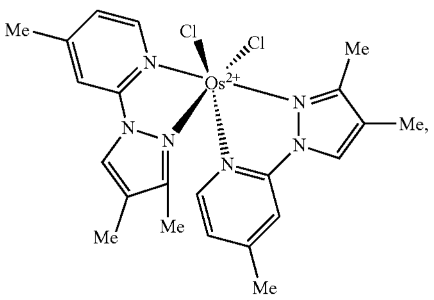
[Chemical formula 21]
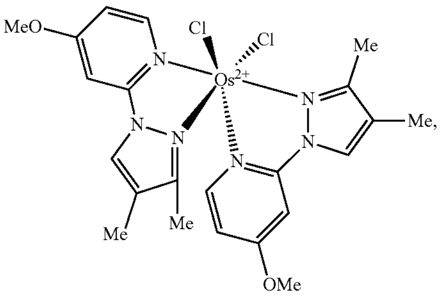
[Chemical formula 22]
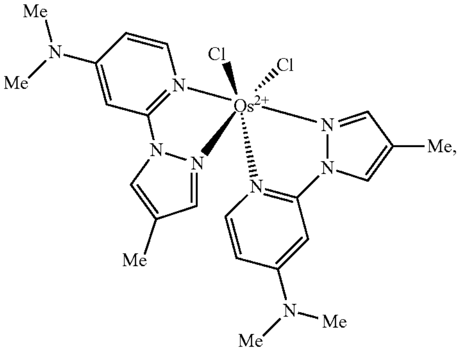

-continued

[Chemical formula 23]

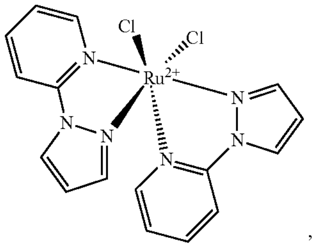

,

[Chemical formula 24]

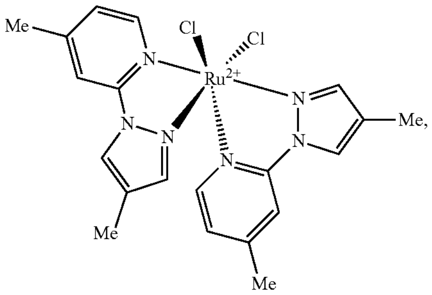

and

[Chemical formula 25]

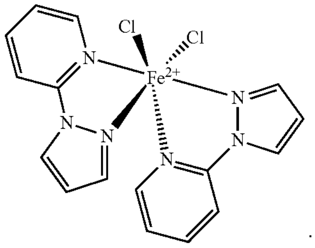

.

In one embodiment, the transition metal complex according to the present invention may comprise a transition metal complex in an oxidized state, specifically, a trivalent osmium complex or a divalent osmium complex. As an oxidizing agent used for oxidation treatment, a commonly used oxidizing agent may be used, and the example of the oxidizing agent may be at least one selected from the group consisting of NaOCl, $H_2O_2$, $O_2$, $O_3$, $PbO_2$, $MnO_2$, $KMnO_4$, $ClO_2$, $F_2$, $CL_2$, $H_2CrO_4$, $N_2O$, $Ag_2O$, $OSO_4$, $H_2S_2O_8$, Ceric ammonium nitrate (CAN), pyridinium chlorochromate, and 2,2'-Dipyridyldisulfide. In addition, when the transition metal complex comprises compounds in an oxidized state and a reduced state, a transition metal complex in an oxidized state or a salt compound thereof may be provided by oxidation treatment.

The transition metal complex according to the present invention may be in a form of an appropriate counter ion and/or a salt compound having an ion, and the salt compound may have high solubility in water, aqueous solution or an organic solvent. In the salt compound, when it consists of small counter anions such as $F^-$, $Cl^-$ and $Br^-$, and the like, it tends to be highly soluble in water or aqueous solution, and when it consists of large counter anions such as hexafluorophosphate ($PF_6^-$) and tetrafluoroborate ($BF_4^-$) and the like, it tends to be highly soluble in an organic solvent. The example of the counter anion may be at least one selected from halide selected from the group consisting of F, Cl, Br and I, hexafluorophosphate and tetrafluoroborate.

In another aspect, the present invention provides an oxidation-reduction polymer, comprising the transition metal complex or salt compound thereof, and comprising a polymer skeleton such as polyvinyl imidazole (PVI) and polyvinyl pyridine (PVP) and the like.

Specifically, the oxidation-reduction polymer may be a compound of the following Chemical formula 26 or Chemical formula 27:

[Chemical formula 26]

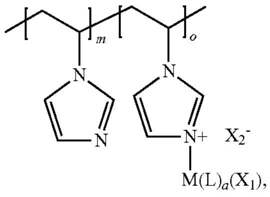

[Chemical formula 27]

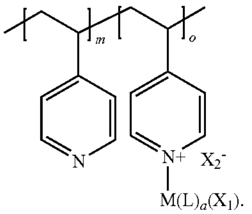

In the formula,

M is one kind transition metal selected from the group consisting of Fe, Ru, and Os, and L is a bidentate ligand comprising pyridine; and one structure selected from the group consisting of pyrazole, triazole, tetrazole, oxadiazole and thiadiazole, and a is 2 or 3, and $X_1$ is one kind halogen atom selected from the group consisting of F, Cl, Br and I, and $X_2$ is one kind counter ion selected from the group consisting of F, Cl, Br, I and $PF_6$, and m or o is an integer selected from 10 to 600, respectively.

The pyridine may be unsubstituted, or substituted with at least one (for example, 1 kind, 2 kinds, 3 kinds, or 4 kinds) selected from the group consisting of $C_{1-4}$ alkyl group, $C_{1-4}$ alkoxy group, —(CH2)-O—$C_{1-4}$ alkyl group, —(CH2CH2)-O—$C_{1-4}$ alkyl group, and $C_{1-4}$ alkylamino group.

The pyrazole, triazole, tetrazole, oxadiazole, or thiadiazole may be unsubstituted, or substituted with at least one (for example, 1 kind, 2 kinds, or 3 kinds) selected from the group consisting of $C_{1-4}$ alkyl group, $C_{1-4}$ alkoxy group, —(CH2)-O—$C_{1-4}$ alkyl group, —(CH2CH2)-O—$C_{1-4}$ alkyl group,

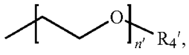

and $C_{1-4}$ alkylamino group.

Specifically, the oxidation-reduction polymer may be a compound selected from the following Chemical formula 28 to Chemical formula 45:
[Chemical formula 28]
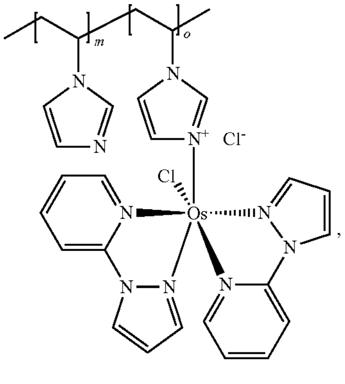
[Chemical formula 29]
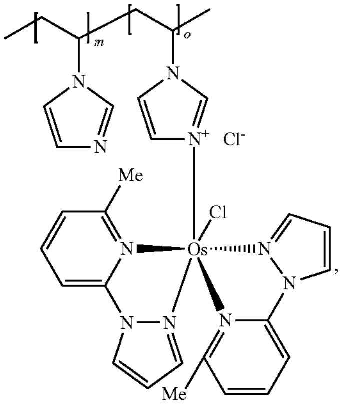
[Chemical formula 30]
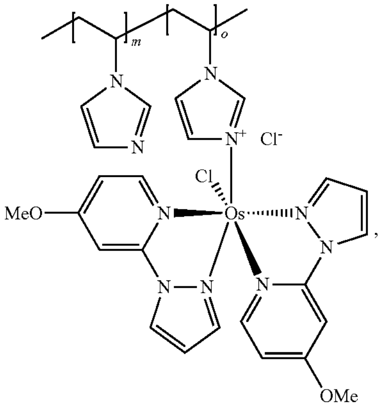
-continued
[Chemical formula 31]
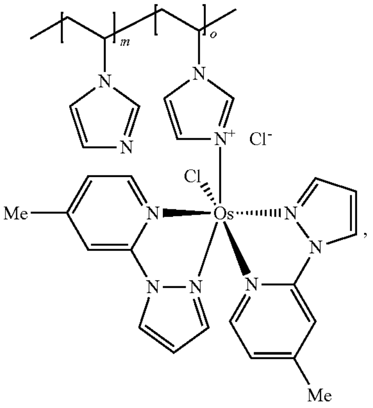
[Chemical formula 32]
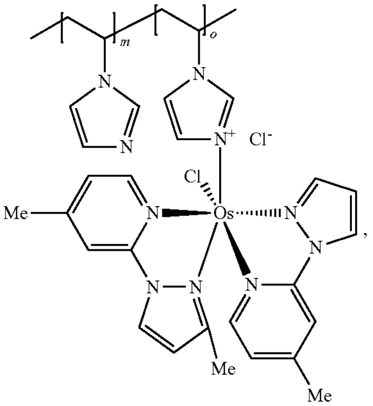
[Chemical formula 33]
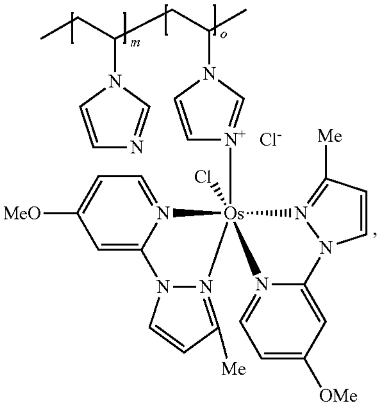

-continued
[Chemical formula 34]
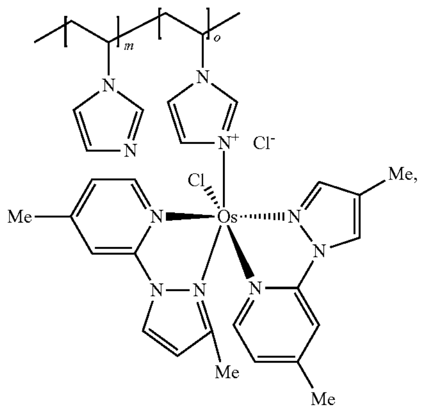
[Chemical formula 35]
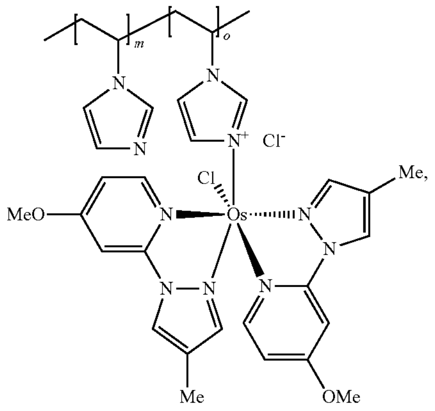
[Chemical formula 36]
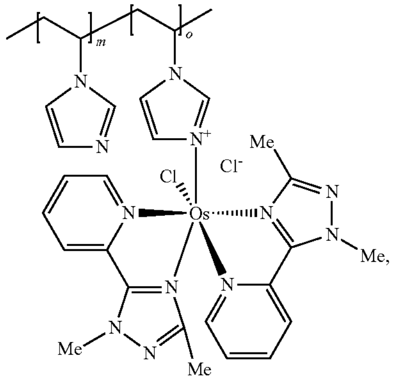
-continued
[Chemical formula 37]
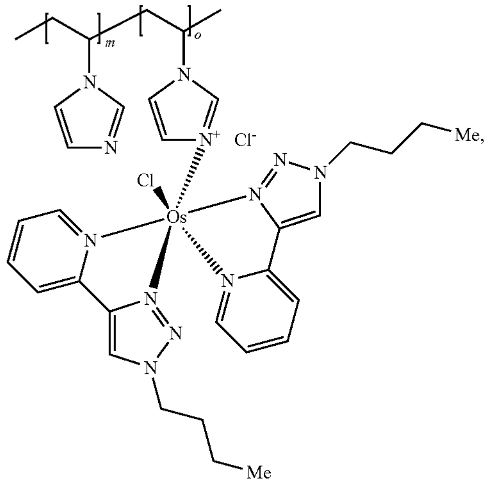
[Chemical formula 38]
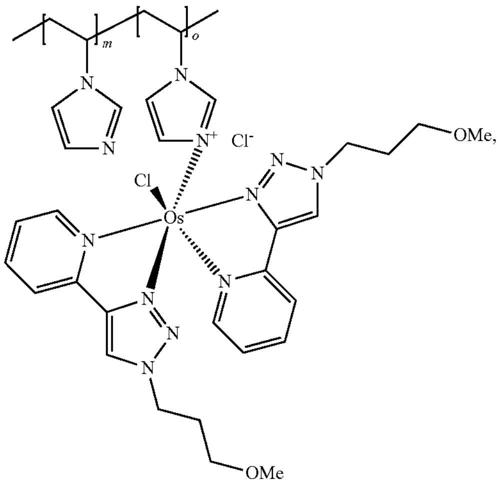
[Chemical formula 39]
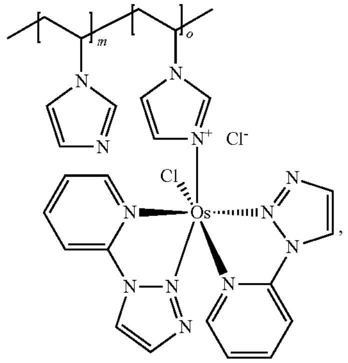

-continued
[Chemical formula 40]
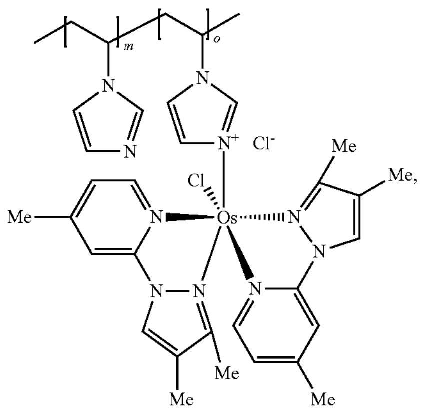
[Chemical formula 41]
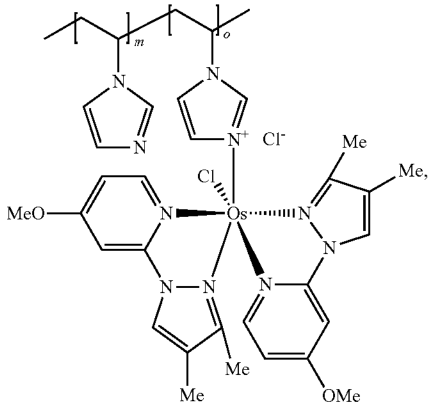
[Chemical formula 42]
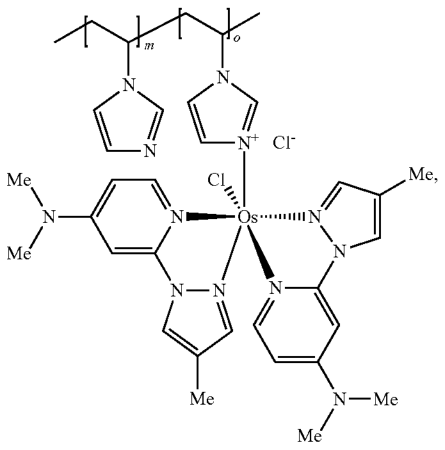
-continued
[Chemical formula 43]
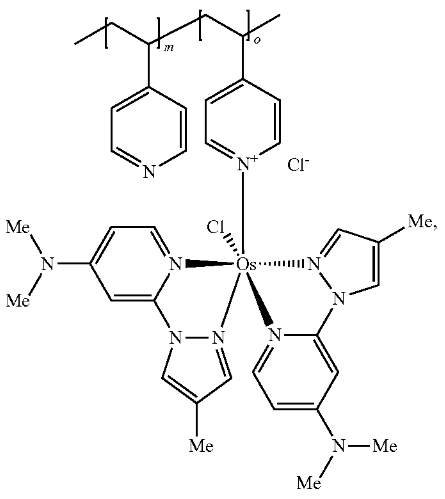
[Chemical formula 44]
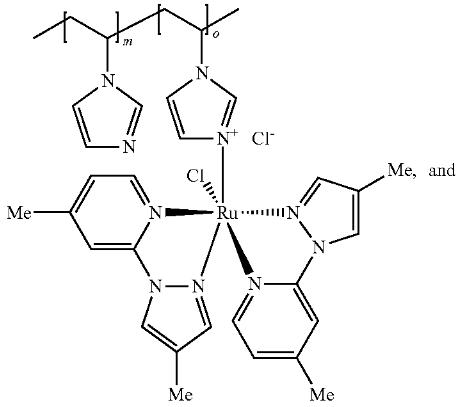
[Chemical formul 45]
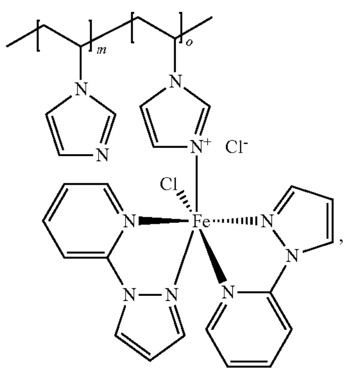
in the formula,
m or o is the same as defined in Chemical formula 26 or Chemical formula 27 above.

In other aspect, in the present invention, the oxidation-reduction polymer further comprises a crosslinkable functional group, and may be a compound of the following Chemical formula 46 or Chemical formula 47.

[Chemical formula 46]

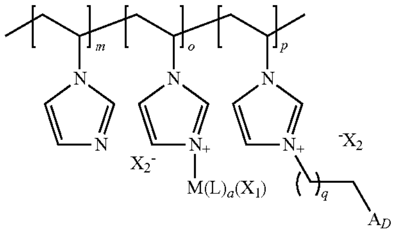

[Chemical formula 47]

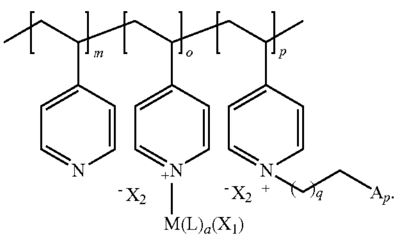

In the formula,

M is one kind transition metal selected from the group consisting of Fe, Ru, Os, Rh and Ir, and L is a bidentate ligand comprising pyridine; and one structure selected from the group consisting of pyrazole, triazole, tetrazole, oxadiazole and thiadiazole, and a is 2 or 3, and $X_1$ is one kind halogen atom selected from the group consisting of F, Cl, Br and I, and $X_2$ is one kind counter ion selected from the group consisting of F, Cl, Br, I and $PF_6$, and $A_D$ is one kind selected from the group consisting of primary and secondary amine groups, ammonium group, halogen group, epoxy group, azide group, acrylate group, alkenyl group, alkynyl group, thiol group, isocyanate, alcohol group, silane group, and

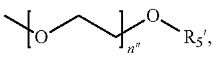

and the $R_5'$ is hydrogen or substituted or unsubstituted $C_{1-4}$ alkyl, and the n" is an integer selected from 1 to 4, and q is an integer selected from 1 to 10, and m, o, or p is an integer selected from 10 to 600, respectively.

The pyridine may be unsubstituted, or substituted with at least one (for example, 1 kind, 2 kinds, 3 kinds, or 4 kinds) selected from the group consisting of $C_{1-4}$ alkyl group, $C_{1-4}$ alkoxy group, —(CH2)-O—$C_{1-4}$ alkyl group, —(CH2CH2)-O—$C_{1-4}$ alkyl group, and $C_{1-4}$ alkylamino group.

The pyrazole, triazole, tetrazole, oxadiazole, or thiadiazole may be unsubstituted, or substituted with at least one (for example, 1 kind, 2 kinds, or 3 kinds) selected from the group consisting of $C_{1-4}$ alkyl group, $C_{1-4}$ alkoxy group, —(CH2)-O—$C_{1-4}$ alkyl group, —(CH2CH2)-O—$C_{1-4}$ alkyl group,

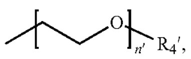

and $C_{1-4}$ alkylamino group, respectively.

Specifically, the oxidation-reduction polymer may be a compound selected from the following Chemical formula 48 to Chemical formula 60.

[Chemical formula 48]

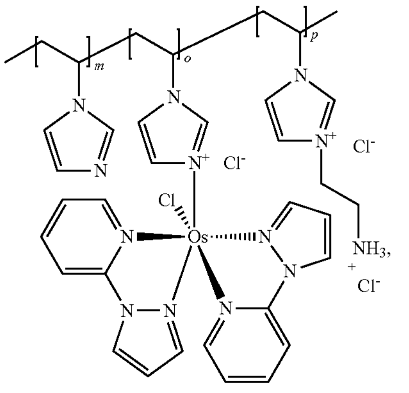

[Chemical formula 49]

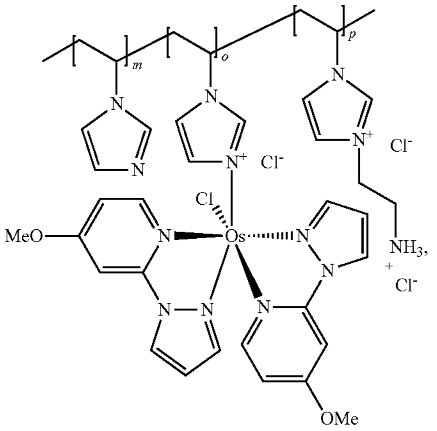

[Chemical formula 50]

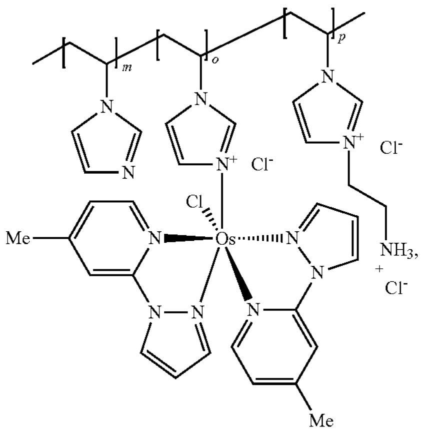

-continued
[Chemical formula 51]
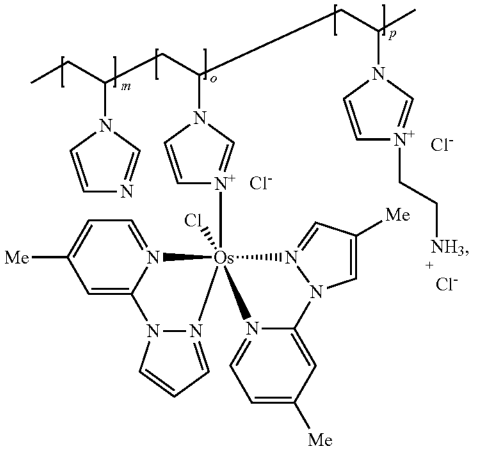
[Chemical formula 52]
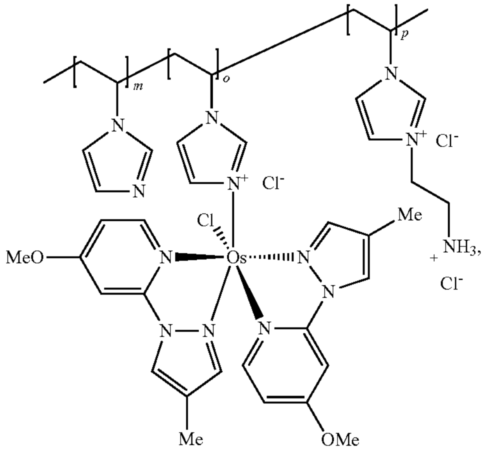
[Chemical formula 53]
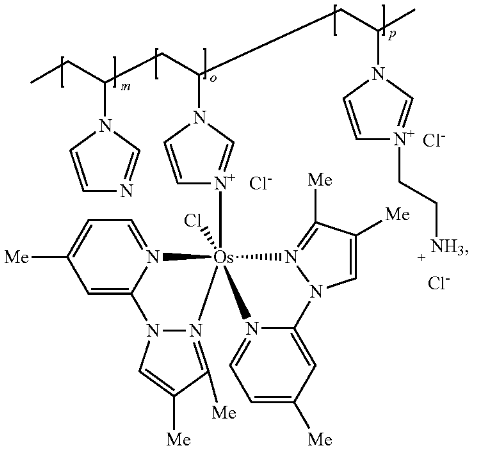
-continued
[Chemical formula 54]
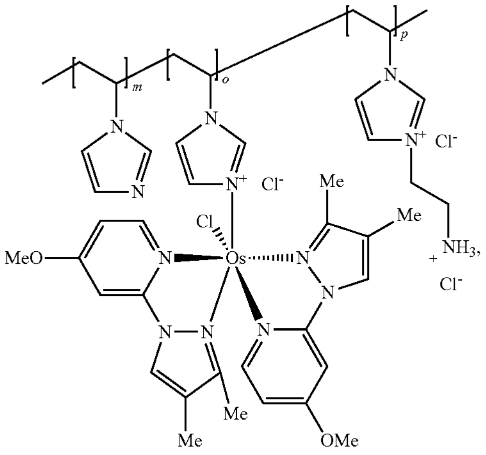
[Chemical formula 55]
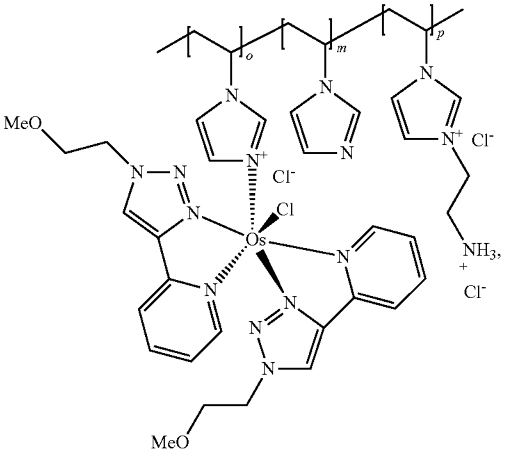
[Chemical formula 56]
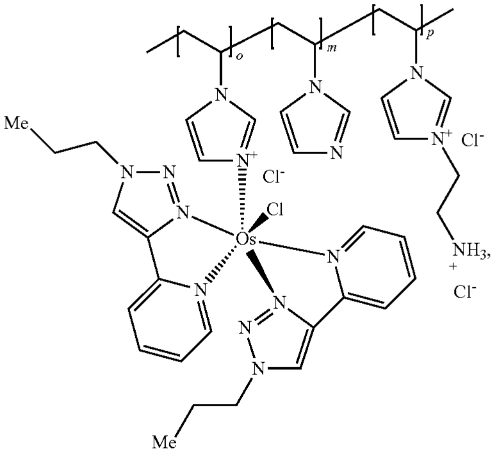

-continued

[Chemical formula 57]

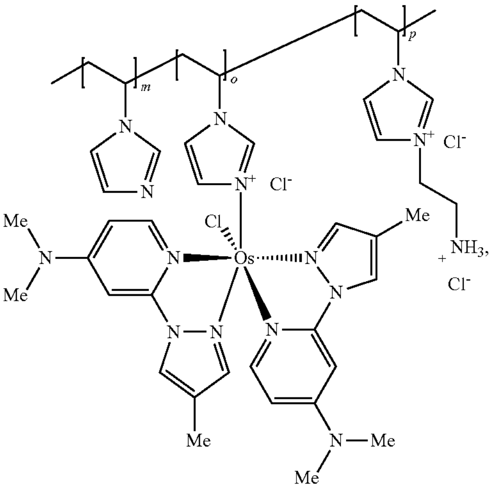

[Chemical formula 58]

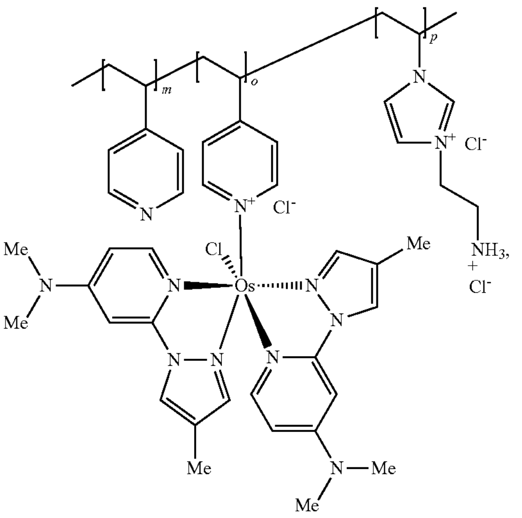

and

[Chemical formula 59]

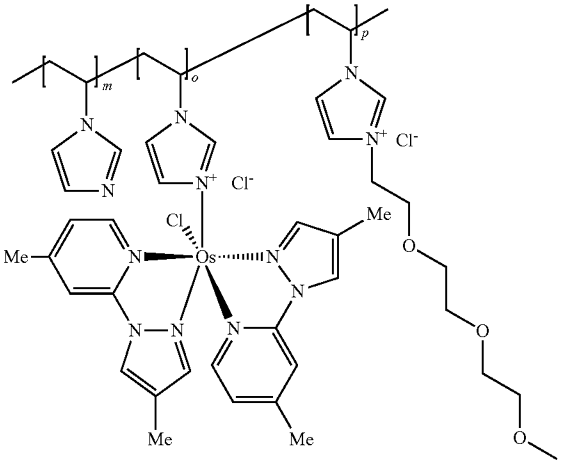

,

-continued

Chemical formula 60]

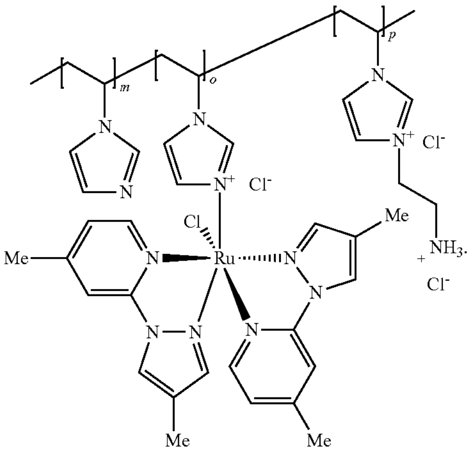

Other aspect provides a device comprising the transition metal complex or salt compound thereof; or the oxidation-reduction polymer.

In one embodiment, the device may be an electrochemical biosensor.

In one embodiment, the device may be insertable in the body, and specifically, may be an electrochemical biosensor insertable in the body.

In one embodiment, the electrochemical biosensor may be a blood glucose sensor, for example, an electrochemical glucose (blood glucose) sensor.

In one embodiment, the electrochemical biosensor may be a continuous blood glucose monitoring sensor.

As the composition of the continuous blood glucose monitoring sensor, the present invention, may comprise for example, an electrode, an insulator, a substrate, a sensing layer comprising the oxidation-reduction polymer and oxidoreductase, a diffusion layer, a protection layer, and the like. In case of the electrode, 2 kinds of electrodes such as a working electrode and a counter electrode may be comprised, and 3 kinds of electrodes such as a working electrode, a counter electrode and a reference electrode may be comprised.

In one embodiment, the biosensor according to the present invention, may be an electrochemical biosensor manufactured by drying after applying a reagent composition comprising the transition metal complex or salt compound thereof; or the oxidation-reduction polymer, and an enzyme capable of oxidizing-reducing a liquid biological sample, on a substrate having at least two, preferably, two or three electrodes.

For example, a planar electrochemical biosensor characterized in that a working electrode and a counter electrode are equipped on the opposite side to each other of a substrate, and a sensing membrane comprising the transition metal complex or oxidation-reduction polymer of the present invention is laminated on the working electrode, and an insulator, a diffusion layer and a protection layer are laminated in order on both sides of the substrate in which the working electrode and counter electrode are equipped, in the electrochemical biosensor.

As a specific aspect, the substrate may be made of at least one material selected from the group consisting of PET (polyethylene terephthalate), PC (polycarbonate) and PI (polyimide).

In addition, as the working electrode, a carbon, gold, platinum, silver or silver/silver chloride electrode may be used.

Furthermore, in case of the electrochemical biosensor having two electrodes, the counter electrode plays a role of the reference electrode, so as the counter electrode, a gold, platinum, silver or silver/silver chloride electrode may be used, and in case of the electrochemical biosensor with 3 electrodes including even the reference electrode, as the reference electrode, a gold, platinum, silver or silver/silver chloride electrode may be used, and as the counter electrode, a carbon electrode may be used.

As the diffusion layer, Nafion, cellulose acetate and silicone rubber may be used, and as the protection layer, silicone rubber, polyurethane, polyurethane-based copolymer, and the like may be used, but not limited thereto.

As a non-limitative example, in case of two electrodes, as the counter electrode plays also a role of the reference electrode, silver chloride or silver may be used, and in case of three electrodes, as the reference electrode, silver chloride or silver may be used, and as the counter electrode, a carbon electrode may be used.

By varying the type of the enzyme comprised in the reagent composition of the present invention, it may be applied for a biosensor for quantification of various materials such as cholesterol, lactate, creatinine, hydrogen peroxide, alcohol, amino acid, and glutamate.

Other aspect provides a sensing membrane for an electrochemical biosensor comprising an enzyme capable of oxidizing-reducing a liquid biological sample; and the transition metal complex or salt compound thereof; or the oxidation-reduction polymer as an electron transfer mediator.

The liquid biological sample may be one or more, two or more, three or more, four or more, or five or more selected from the group consisting of for example, a patient's tissue fluid, blood, cells, plasma, serum, urine, cyst liquid and saliva, but not limited thereto.

In one embodiment, the enzyme may comprise at least one oxidoreductase selected from the group consisting of dehydrogenase, oxidase, and esterase; or at least one oxidoreductase selected from the group consisting of dehydrogenase, oxidase, and esterase and at least one cofactor selected from the group consisting of flavin adenine dinucleotide (FAD), nicotinamide adenine dinucleotide (NAD), and pyrroloquinoline quinone (PQQ).

Oxidoreductase collectively refers to enzymes catalyzing oxidation-reduction reactions of a living body, and in the present invention, it means an enzyme reduced by reacting with a target substance, for example, in case of the biosensor, a target substance to be measured. The enzyme reduced as such reacts with an electron transfer mediator, and the target substance is quantified by measuring the change in current generated then, and the like. The oxidoreductase usable in the present invention may be at least one selected from the group consisting of various kinds of dehydrogenase, oxidase, esterase, and the like, and depending on the target substance for oxidation-reduction or detection, among enzymes belonging to the above enzyme group, an enzyme using the target substance as a substrate may be selected and used.

More specifically, the oxidoreductase may be at least one selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, bilirubin oxidase and the like.

On the other hand, the oxidoreductase may comprise a cofactor playing a role of storing hydrogen stolen by oxidoreductase from a target substance to be measured (for example, target substance), and for example, it may be at least one selected from the group consisting of flavin adenine dinucleotide (FAD), nicotinamide adenine dinucleotide (NAD), pyrroloquinoline quinone (PQQ) and the like.

For example, when a blood glucose concentration is to be measured, as the oxidoreductase, glucose dehydrogenase (GDH) may be used, and the glucose dehydrogenase may be flavin adenine dinucleotide-glucose dehydrogenase (FAD-GDH) comprising FAD as the cofactor, and/or nicotinamide adenine dinucleotide-glucose dehydrogenase comprising FAD-GDH as the cofactor.

In a specific example, the usable oxidoreductase may be at least one selected from the group consisting of FAD-GDH (for example, EC 1.1.99.10, etc.), NAD-GDH (for example, EC 1.1.1.47, etc.), PQQ-GDH (for example, EC1.1.5.2, etc.), glutamate dehydrogenase (for example, EC 1.4.1.2, etc.), glucose oxidase (for example, EC 1.1.3.4, etc.), cholesterol oxidase (for example, EC 1.1.3.6, etc.), cholesterol esterification enzyme (for example, EC 3.1.1.13, etc.), lactate oxidase (for example, EC 1.1.3.2, etc.), ascorbic acid oxidase (for example, EC 1.10.3.3, etc.), alcohol oxidase (for example, EC 1.1.3.13, etc.), alcohol dehydrogenase (for example, EC 1.1.1.1, etc.), bilirubin oxidase (for example, EC 1.3.3.5, etc.) and the like.

Most preferably, the oxidoreductase is glucose dehydrogenase which can maintain activity of 70% or more in a 37° C. buffer solution for 1 week.

The sensing membrane according to the present invention may contain 20 to 700 parts by weight, for example, 60 to 700 parts by weight, or 30 to 340 parts by weight of the oxidation-reduction polymer based on 100 parts by weight of oxidoreductase. The content of the oxidation-reduction polymer may be appropriately adjusted depending on the activity of the oxidoreductase.

Moreover, the sensing membrane according to the present invention may further comprise a carbon nanotube for an increase of membrane performance. Specifically, the carbon nanotube may further increase performance of the sensing membranes, as the electron transfer speed increases, when used with a transition metal complex, particularly, osmium.

In addition, the sensing membrane according to the present invention may further comprise a crosslinking agent.

On the other hand, the sensing membrane according to the present invention may additionally comprise at least one additive selected from the group consisting of surfactants, water-soluble polymers, quaternary ammonium salts, fatty acids, thickeners and the like, for a role of a dispersant during dissolving a reagent, an adhesive during preparing a reagent, a stabilizer during long-term storage, and the like.

The surfactant may play a role of making a composition is evenly spread and aliquoted in a uniform thickness on an electrode, when the composition is aliquoted. As the surfactant, at least one selected from the group consisting of Triton X-100, sodium dodecyl sulfate, perfluorooctane sulfonate, sodium stearate, and the like may be used. The reagent composition according to the present invention may contain the surfactant in an amount of 3 to 25 parts by weight, for example, 10 to 25 parts by weight, based on 100 parts by weight of oxidoreductase, in order to allow it to appropriately perform a role that the reagent is evenly spread on the electrode when the reagent is aliquoted, and the reagent is aliquoted in a uniform thickness. For example, when oxidoreductase with activity of 700 U/mg is used, it may contain 10 to 25 parts by weight of the surfactant based on 100 parts by weight of oxidoreductase, and when the activity of oxidoreductase becomes higher than this, the content of the surfactant may be adjusted lower than this.

The water-soluble polymer is a polymer support of the reagent composition and may perform a role of helping stabilization and dispersing of an enzyme. As the water-soluble polymer, at least one selected from the group consisting of polyvinyl pyrrolidone (PVP), polyvinyl alcohol (PVA), polyperfluoro sulfonate, hydroxyethyl cellulose (HEC), hydroxypropyl cellulose (HPC), carboxy methyl cellulose (CMC), cellulose acetate, polyamide, and the like may be used. The reagent composition according to the present invention may contain the water-soluble polymer in an amount of 10 to 70 parts by weight, for example, 30 to 70 parts by weight, based on 100 parts by weight of oxidoreductase, in order to sufficiently and appropriately exhibit the role of helping stabilization and dispersing of oxidoreductase. For example, when oxidoreductase with activity of 700 U/mg is used, it may contain 30 to 70 parts by weight of the water-soluble polymer based on 100 parts by weight of oxidoreductase, and when the activity of the oxidoreductase is higher than this, the content of the water-soluble polymer may be adjusted lower than this.

The water-soluble polymer may have a weight average molecular weight of about 2,500 g/mol to 3,000,000 g/mol, for example, about 5,000 g/mol to 1,000,000 g/mol, in order to effectively perform the role of helping stabilization and dispersing of the support and enzyme.

The thickener plays a role of firmly attaching a reagent to an electrode. As the thickener, at least one selected from the group consisting of Natrosol, diethylaminoethyl-dextran hydrochloride (DEAE-Dextran hydrochloride) and the like may be used. The electrochemical sensor according to the present invention may contain the thickener in an amount of 10 to 90 parts by weight, for example, 30 to 90 parts by weight, based on 100 parts by weight of oxidoreductase. For example, when oxidoreductase with activity of 700 U/mg is used, it may contain 30 to 90 parts by weight of the thickener based on 100 parts by weight of oxidoreductase, and when the activity of the oxidoreductase is higher than this, the content of the thickener may be adjusted lower than this.

Advantageous Effects

The transition metal complex and oxidation-reduction polymer according to the present invention can easily adjust a potential value depending on the type of ligand introduced, and the size of the ligand is minimized than the conventional bipyridine-based one, so the electron transfer speed is increased, and therefore, the electrochemical biosensor in which this is applied has an advantage of rapid and economical detection.

BRIEF DESCRIPTION OF THE DRAWINGS

FIG. 1*a* to FIG. 10 are cyclic voltammetry curves showing electrochemical characteristics of the transition metal complex having the bidentate ligand comprising pyrazole, triazole, tetrazole, oxadiazole, or thiadiazole according to the present invention.

{Chemical formula 3 (FIG. 1*a*), Chemical formula 4 (FIG. 1*b*), Chemical formula 9 (FIG. 1*c*), Chemical formula 11 (FIG. 1*d*), Chemical formula 14 (FIG. 1*e*), Chemical formula 15 (FIG. 1*f*), Chemical formula 16 (FIG. 1*g*), Chemical formula 17 (FIG. 1*h*), Chemical formula 18 (FIG. 1*i*), Chemical formula 20 (FIG. 1*j*), Chemical formula 22 (FIG. 1*k*), Chemical formula 23 (FIG. 1*l*), Chemical formula 24 (FIG. 1*m*), Chemical formula 25 (FIG. 1*n*), Chemical formula 3, 4, 11, 14, 15, 16 (FIG. 1*o*)}

FIG. 2 is a cyclic voltammetry curves showing electrochemical characteristics of the oxidation-reduction polymer comprising the transition metal complex according to the present invention.

FIG. 3 is a cyclic voltammetry curves showing electrochemical characteristics of the oxidation-reduction polymer comprising the transition metal complex according to the present invention and a crosslinkable functional group.

FIG. 4 shows a potential of an electrode to which the oxidation-reduction polymer according to the present invention is applied.

FIG. 5 and FIG. 6 are graphs which show that all the electrodes to which the oxidation-reduction polymer according to the present invention is applied showed the linearity for glucose at a concentration of 10 mM or less, and showed similar sensitivity, even though voltage lower than the comparative group electrode was applied.

FIG. 7 is a graph which shows that all the electrodes to which the oxidation-reduction polymer according to the present invention is applied showed sensitivity for glucose at voltage lower than the comparative group electrode.

MODE FOR INVENTION

Hereinafter, the present invention will be described in more detail by the following examples. However, the following examples illustrate the present invention only, but the contents of the present invention are not limited by the following examples.

Example 1: Preparation of Transition Metal Complex According to the Present Invention

Example 1.1. Synthesis of Transition Metal Complex of Chemical Formula 3

1) Synthesis of 2-(1H-pyrazol-1-yl)pyridine

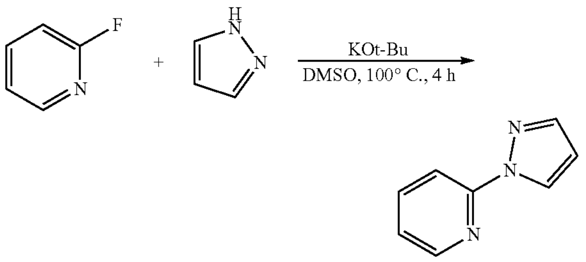

A reflux condenser and a gas inlet were equipped to a 250 mL two-neck round bottom flask, and pyrazole 4.7 g (69 mmol) and potassium butoxide 9.3 g (83 mmol) were added, and dissolved in anhydrous dimethylsulfoxide 40 mL in an argon gas atmosphere. To this reaction mixture, 2-fluoropyrifine 8.0 g (83 mmol) was added and heated to 100° C. in an argon gas atmosphere and stirred for 4 hours. After completing the reaction, the reaction mixture was cooled to a room temperature and extracted with water (100 mL) and ethylacetate (100 mL×3). Organic layers were collected and dried with magnesium sulfate and concentrated under reduced pressure to obtain a transparent, colorless solid. (7.2 g, 72%)

2) Synthesis of $Os(pzpy)_2Cl_2$ [Chemical formula 3]

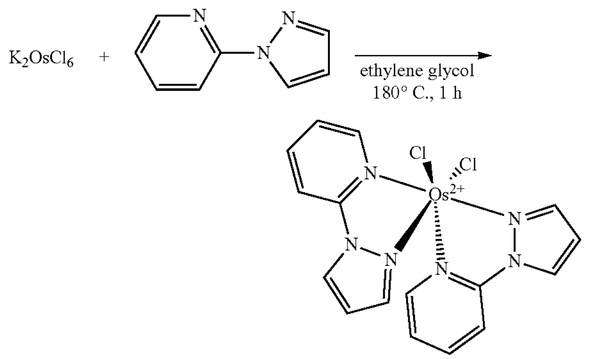

Potassium hexachloroosmate(IV) 5.0 g (10 mmol) and 2-(1H-pyrazol-1-yl)pyridine 2.9 g (20 mmol) prepared in 1) above were added in a 500 mL shrink flask, and dissolved in 200 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (250 mL), thereby obtaining precipitates of the reduced osmium complex. The produced solid was filtered under reduced pressure and washed with water several times, and then dried in a vacuum oven of 40° C. to obtain a green final compound osmium complex. (4.0 g, 75%) HRMS ($^{192}Os$): m/z 552.0240($[M^+]$ required 552.0261)

The entire preparation method of the compound of Chemical formula 3 is as the following Reaction formula 1.

[Reaction formula 1]

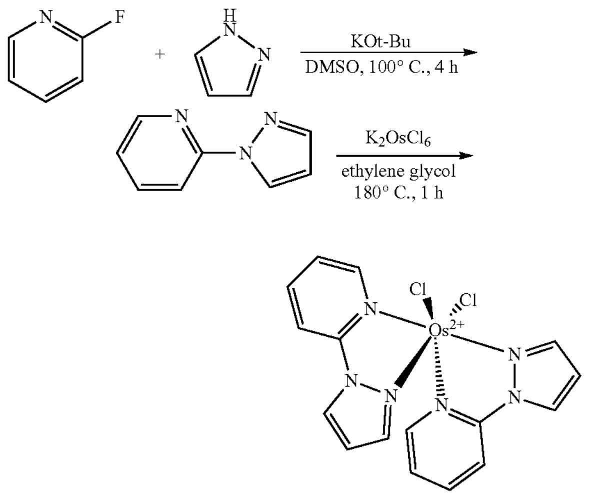

Example 1.2. Synthesis of Transition Metal Complex of Chemical Formula 4

1) Synthesis of 2-methyl-6-(1H-pyrazol-1-yl)pyridine

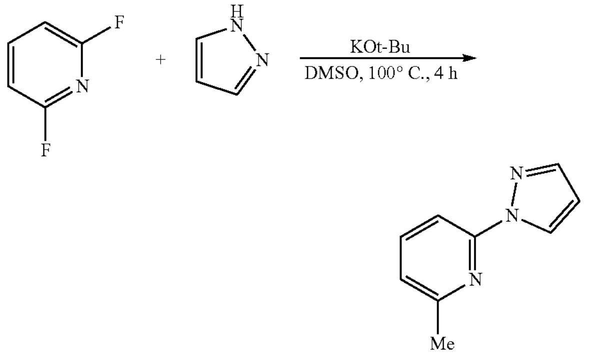

A reflux condenser and a gas inlet were equipped to a 250 mL two-neck round bottom flask, and pyrazole 2.0 g (30 mmol) and potassium tertiary butoxide 4.0 g (36 mmol) were added and dissolved in an anhydrous dimethylsulfoxide 20 mL in an argon gas atmosphere. 2-fluoro-5-methyl pyridine 5.0 g (36 mmol) was added to this reaction mixture and heated to 100° C. in an argon gas atmosphere and stirred for 4 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=5:1) Finally, 2-methyl-6-(1H-pyrazol-1-yl)pyridine of a transparent solid was obtained. (1.4 g, 30%)

2) Synthesis of $Os(pz\text{-}2\text{-}Me\text{-}py)_2Cl_2$ [Chemical formula 4]

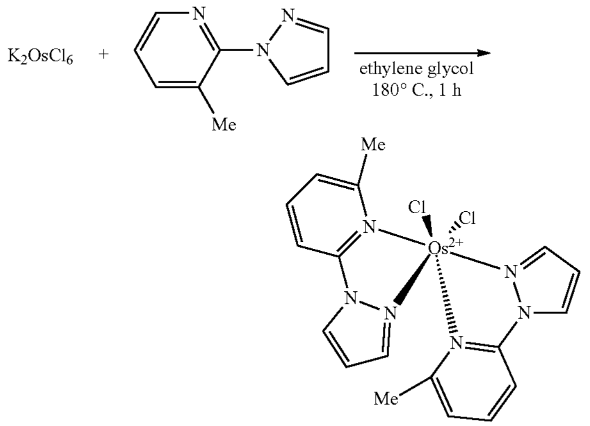

Potassium hexachloroosmate(IV) 1.5 g (3.1 mmol) and 2-(1H-pyrazol-1-yl)pyridine 1.0 g (6.3 mmol) prepared in 1) above were added in a 250 mL shrink flask, and dissolved in 50 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (250 mL), thereby obtaining precipitates of the reduced osmium complex. The produced solid was filtered under reduced pressure and washed with water and acetonitrile several times, and then dried in a vacuum oven to obtain a green final compound osmium complex. (0.27 g, 15%) HRMS ($^{192}Os$): m/z 580.0569([$M^+$] required 580.0574)

The entire preparation method of the compound of Chemical formula 4 is as the following Reaction formula 2.

[Reaction formula 2]

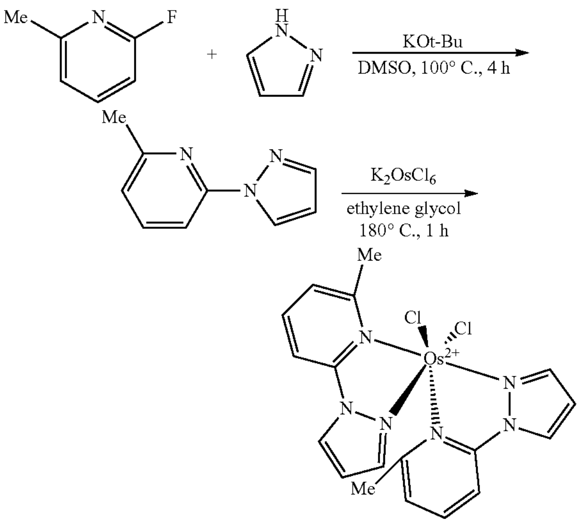

Example 1.3. Synthesis of Transition Metal Complex of Chemical Formula 5

1) Synthesis of 4-methoxy-2-(1H-pyrazol-1-yl)pyridine

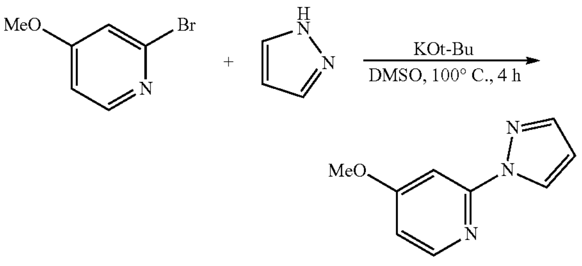

A reflux condenser and a gas inlet were equipped to a 250 mL two-neck round bottom flask, and pyrazole 2.0 g (30 mmol) and potassium tertiary butoxide 4.0 g (36 mmol) were added and dissolved in an anhydrous dimethylsulfoxide 20 mL in an argon gas atmosphere. 2-bromo-4-methoxy pyridine 6.7 g (36 mmol) was added to this reaction mixture and heated to 100° C. in an argon gas atmosphere and stirred for 8 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=3:1) Finally, 4-methoxy-2-(1H-pyrazol-1-yl)pyridine of a transparent solid was obtained. (4.0 g, 63%)

2) Synthesis of $Os(pz\text{-}4\text{-}Meo\text{-}py)_2Cl_2$ [Chemical formula 5]

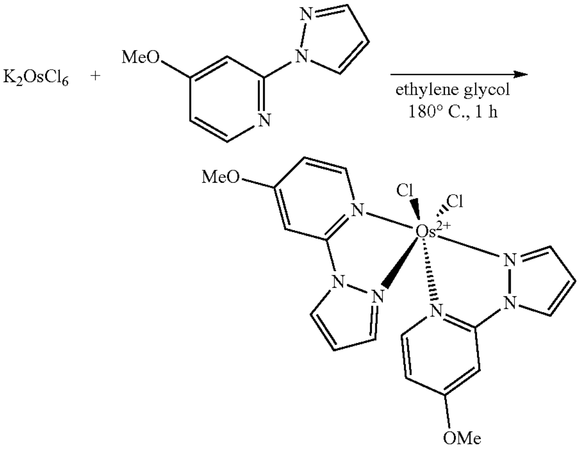

Potassium hexachloroosmate(IV) 2.0 g (4.2 mmol) and 4-methoxy-2-(1H-pyrazol-1-yl)pyridine 1.5 g (8.3 mmol) prepared in 1) above were added in a 250 mL shrink flask, and dissolved in 50 mL ethylene glycol in an argon gas atmosphere, and then argon degassing was performed for 15 minutes. This reaction mixture was heated 10 to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (250 mL), thereby obtaining precipitates of the reduced osmium complex. The produced solid was filtered under reduced pressure and washed with water and acetonitrile several times, and then dried in a vacuum oven to obtain a green final compound osmium complex. (2.0 g, 78%) HRMS ($^{192}Os$): m/z 612.0460([$M^+$] required 612.0472)

The entire preparation method of the compound of Chemical formula 5 is as the following Reaction formula 3.

[Reaction formula 3]

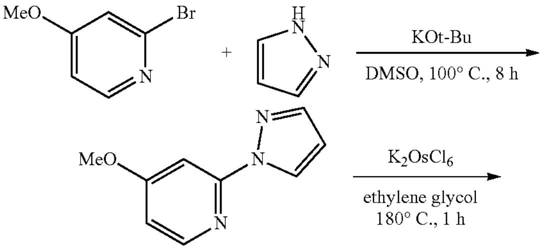

-continued

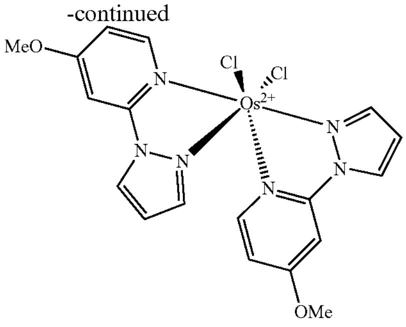

Example 1.4. Synthesis of Transition Metal Complex of Chemical Formula 6

1) Synthesis of 4-methyl-2-(1H-pyrazol-1-yl)pyridine

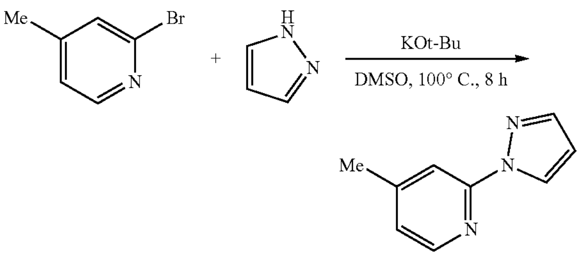

A reflux condenser and a gas inlet were equipped to a 250 mL two-neck round bottom flask, and pyrazole 2.0 g (30 mmol) and potassium tertiary butoxide 4.0 g (36 mmol) were added and dissolved in an anhydrous dimethylsulfoxide 20 mL in an argon gas atmosphere. 2-bromo-4-methyl pyridine 6.2 g (36 mmol) was added to this reaction mixture and heated to 100° C. in an argon gas atmosphere and stirred for 8 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=3:1) Finally, 4-methoxy-2-(1H-pyrazol-1-yl)pyridine of a transparent solid was obtained. (3.5 g, 61%)

2) Synthesis of Os(pz-4-Me-py)$_2$Cl$_2$ [Chemical formula 6]

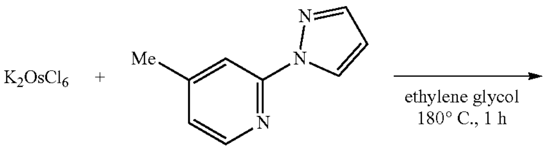

-continued

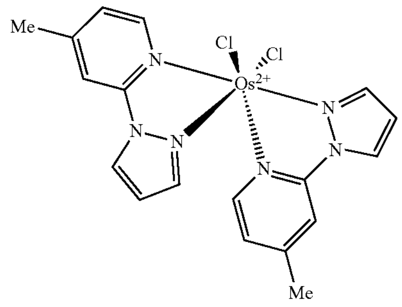

Potassium hexachloroosmate(IV) 2.0 g (4.2 mmol) and 4-methyl-2-(1H-pyrazol-1-yl)pyridine 1.3 g (8.3 mmol) prepared in 1) above were added in a 250 mL shrink flask, and dissolved in 50 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (250 mL), thereby obtaining precipitates of the reduced osmium complex. The produced solid was filtered under reduced pressure and washed with water and acetonitrile several times, and then dried in a vacuum oven to obtain a green final compound osmium complex. (1.0 g, 42%) HRMS ($^{192}$Os): m/z 580.0561([M$^+$] required 580.0574)

The entire preparation method of the compound of Chemical formula 6 is as the following Reaction formula 4.

[Reaction formula 4]

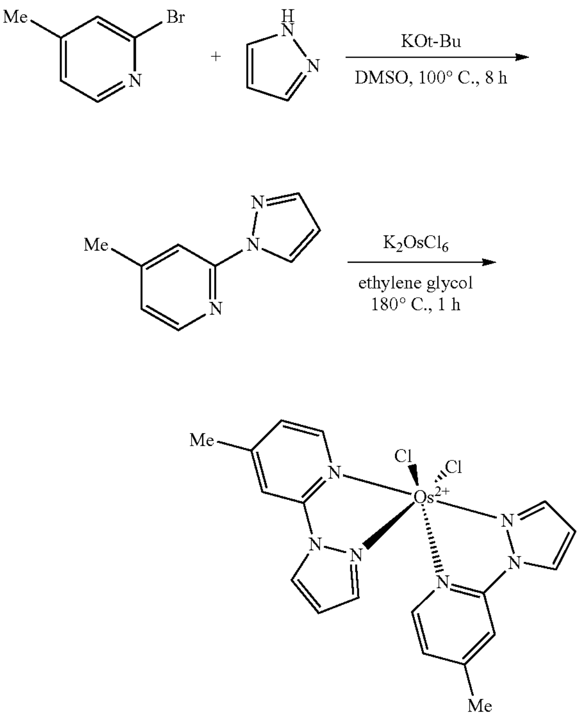

Example 1.5. Synthesis of Transition Metal Complex of Chemical Formula 7

1) Synthesis of 4-methyl-2-(3-methyl-1H-pyrazol-1-yl)pyridine

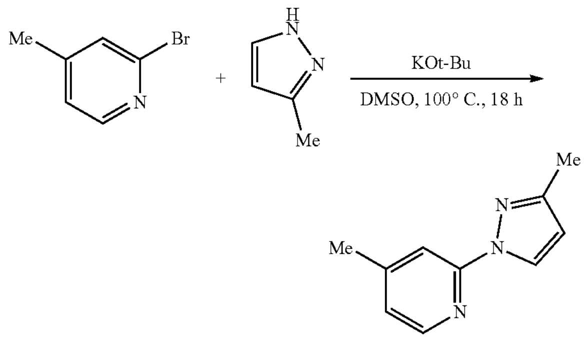

A reflux condenser and a gas inlet were equipped to a 250 mL two-neck round bottom flask, and 3-methylpyrazole 2.5 g (30 mmol) and potassium tertiary butoxide 4.0 g (36 mmol) were added and dissolved in an anhydrous dimethylsulfoxide 20 mL in an argon gas atmosphere. 2-bromo-4-methyl pyridine 6.2 g (36 mmol) was added to this reaction mixture and heated to 100° C. in an argon gas atmosphere and stirred for 18 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=3:1) Finally, 4-methyl-2-(3-methyl-1H-pyrazol-1-yl)pyridine of a transparent solid was obtained. (4.2 g, 80%)

2) Synthesis of $Os(3\text{-}Me\text{-}pz\text{-}4\text{-}Me\text{-}py)_2Cl_2$ [Chemical formula 7]

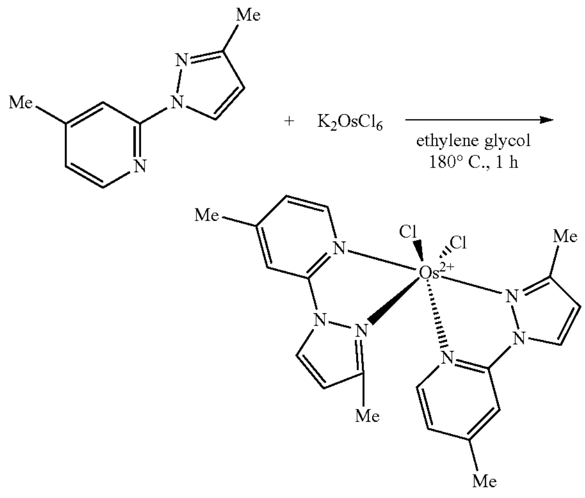

Potassium hexachloroosmate(IV) 2.0 g (4.2 mmol) and 4-methyl-2-(3-methyl-1H-pyrazol-1-yl)pyridine 1.4 g (8.3 mmol) prepared in 1) above were added in a 250 mL shrink flask, and dissolved in 50 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (250 mL), thereby obtaining precipitates of the reduced osmium complex. The produced solid was filtered under reduced pressure and washed with water and acetonitrile several times, and then dried in a vacuum oven to obtain a green final compound osmium complex. (2.0 g, 78%) HRMS ($^{192}Os$): m/z 608.0875([$M^+$] required 608.0887)

The entire preparation method of the compound of Chemical formula 7 is as the following Reaction formula 5.

[Reaction formula 5]

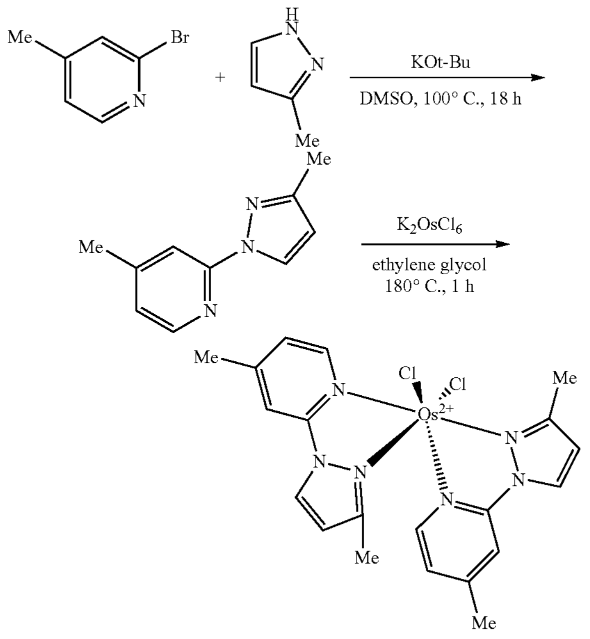

Example 1.6. Synthesis of Transition Metal Complex of Chemical Formula 8

1) Synthesis of 4-methoxy-2-(3-methyl-1H-pyrazol-1-yl)pyridine

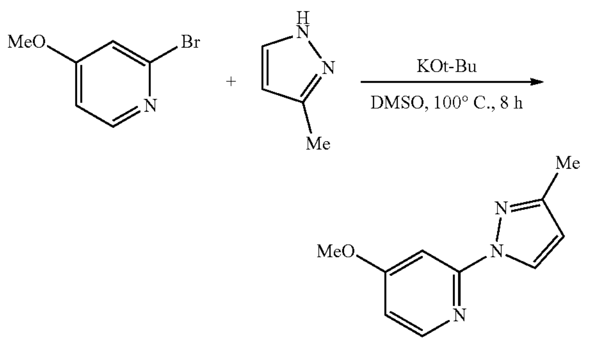

A reflux condenser and a gas inlet were equipped to a 250 mL two-neck round bottom flask, and 3-methylpyrazole 2.5 g (30 mmol) and potassium tertiary butoxide 4.0 g (36 mmol) were added and dissolved in an anhydrous dimethylsulfoxide 20 mL in an argon gas atmosphere. 2-bromo-4-methoxy pyridine 6.7 g (36 mmol) was added to this reaction mixture and heated to 100° C. in an argon gas atmosphere and stirred for 18 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=3:1) Finally, 4-methoxy-2-(3-methyl-1H-pyrazol-1-yl)pyridine of a transparent solid was obtained. (3.0 g, 53%)

2) Synthesis of $Os(3\text{-}Me\text{-}p\text{-}4\text{-}MeO\text{-}py)_2Cl_2$ [Chemical formula 8]

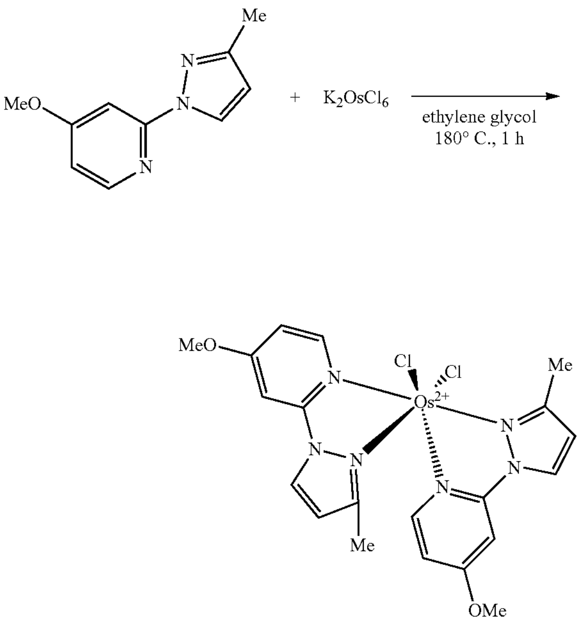

Potassium hexachloroosmate(IV) 2.0 g (4.2 mmol) and 4-methoxy-2-(3-methyl-1H-pyrazol-1-yl)pyridine 1.5 g (8.3 mmol) prepared in 1) above were added in a 250 mL shrink flask, and dissolved in 50 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (250 mL), thereby obtaining precipitates of the reduced osmium complex. The produced solid was filtered under reduced pressure and washed with water and acetonitrile several times, and then dried in a vacuum oven to obtain a green final compound osmium complex. (1.0 g, 37%) HRMS ($^{192}Os$): m/z 640.0775([$M^+$] required 640.0785)

The entire preparation method of the compound of Chemical formula 8 is as the following Reaction formula 6.

[Reaction formula 6]

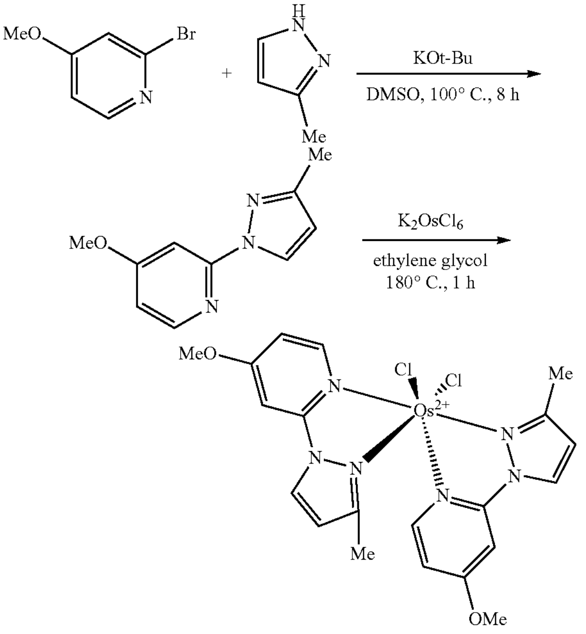

Example 1.7. Synthesis of Transition Metal Complex of Chemical Formula 9

1) Synthesis of 4-methyl-2-(4-methyl-1H-pyrazol-1-yl)pyridine

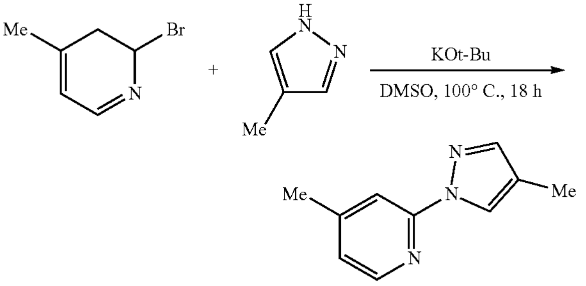

A reflux condenser and a gas inlet were equipped to a 250 mL two-neck round bottom flask, and 4-methylpyrazole 2.5 g (30 mmol) and potassium tertiary butoxide 4.0 g (36 mmol) were added and dissolved in an anhydrous dimethylsulfoxide 20 mL in an argon gas atmosphere. 2-bromo-4-methyl pyridine 6.2 g (36 mmol) was added to this reaction mixture and heated to 100° C. in an argon gas atmosphere and stirred for 18 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=3:1) Finally, 4-methyl-2-(4-methyl-1H-pyrazol-1-yl)pyridine of a transparent solid was obtained. (4.5 g, 86%)

2) Synthesis of $Os(4\text{-}Me\text{-}pz\text{-}4\text{-}Me\text{-}py)_2Cl_2$ [Chemical formula 9]

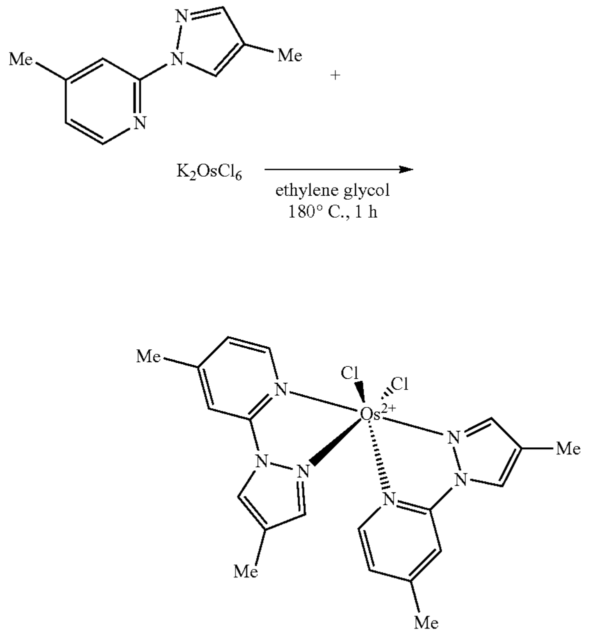

Potassium hexachloroosmate(IV) 5.0 g (10 mmol) and 4-methyl-2-(4-methyl-1H-pyrazol-1-yl)pyridine 4.1 g (21 mmol) prepared in 1) above were added in a 250 mL shrink flask, and dissolved in 100 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (250 mL), thereby obtaining precipitates of the reduced osmium complex. The produced solid was filtered under reduced pressure and washed with water and acetonitrile several times, and then dried in a vacuum oven to obtain a green final compound osmium complex. (5.5 g, 91%) HRMS ($^{192}Os$): m/z 608.0871([$M^+$] required 608.0887)

The entire preparation method of the compound of Chemical formula 9 is as the following Reaction formula 7.

[Reaction formula 7]

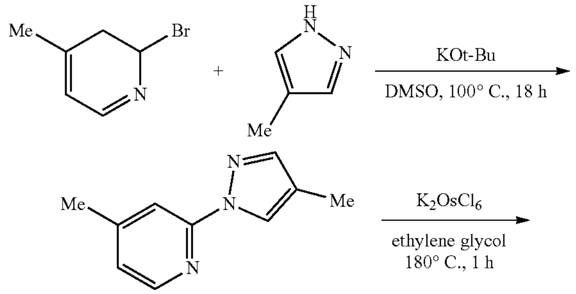

-continued

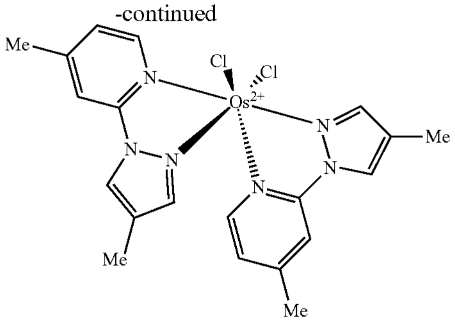

Example 1.8. Synthesis of Transition Metal Complex of Chemical Formula 10

1) Synthesis of 4-methoxy-2-(4-methyl-1H-pyrazol-1-yl)pyridine

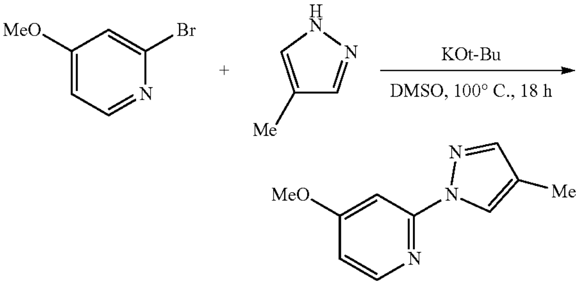

A reflux condenser and a gas inlet were equipped to a 250 mL two-neck round bottom flask, and 4-methylpyrazole 2.5 g (30 mmol) and potassium tertiary butoxide 4.0 g (36 mmol) were added and dissolved in an anhydrous dimethylsulfoxide 20 mL in an argon gas atmosphere. 2-bromo-4-methoxy pyridine 6.7 g (36 mmol) was added to this reaction mixture and heated to 100° C. in an argon gas atmosphere and stirred for 18 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=3:1) Finally, 4-methoxy-2-(4-methyl-1H-pyrazol-1-yl)pyridine of a transparent solid was obtained. (2.8 g, 50%)

2) Synthesis of $Os(4\text{-}Me\text{-}pz4\text{-}MeO\text{-}py)_2Cl_2$ [Chemical formula 10]

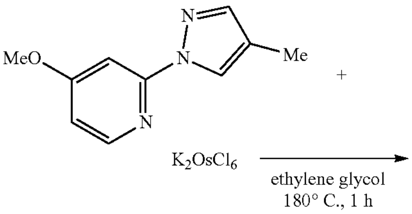

-continued

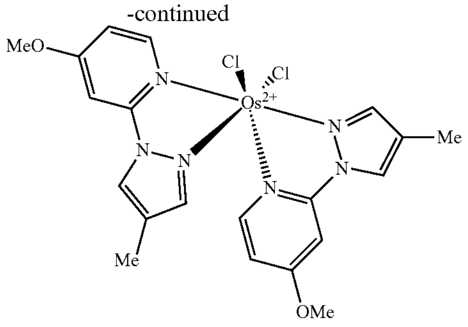

Potassium hexachloroosmate(IV) 3.0 g (6.2 mmol) and 4-methoxy-2-(4-methyl-1H-pyrazol-1-yl)pyridine 2.4 g (12 mmol) prepared in 1) above were added in a 250 mL shrink flask, and dissolved in 60 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (250 mL), thereby obtaining precipitates of the reduced osmium complex. The produced solid was filtered under reduced pressure and washed with water and acetonitrile several times, and then dried in a vacuum oven to obtain a green final compound osmium complex. (2.3 g, 58%) HRMS ($^{192}Os$): m/z 640.0792([$M^+$] required 640.0785)

The entire preparation method of the compound of Chemical formula 10 is as the following Reaction formula 8.

[Reaction formula 8]

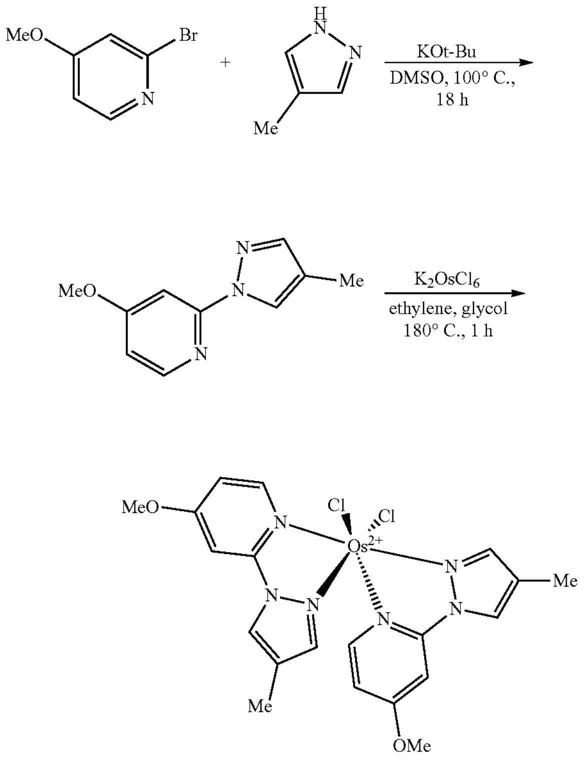

Example 1.9. Synthesis of Transition Metal Complex of Chemical Formula 11

1) Synthesis of (pyridin-2-yl)amidrazone

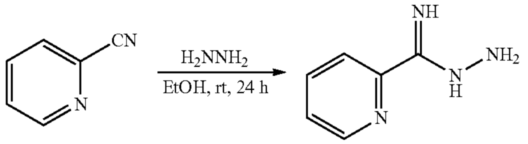

2-cyanopyridine 5.2 g (50 mmol) and hydrazine hydrates 2.7 g (55 mmol) were added in a 100 mL two-neck round bottom flask, and ethanol 4 mL was added and they were stirred at a room temperature for 24 hours. After completing the reaction, the reaction mixture was filtered under reduced pressure to remove remaining solvents, and washed with benzene. The filtered solid was recrystallized in toluene to obtain (pyridin-2-yl)amidrazone. (4.2 g, 61%)

2) Synthesis of 2-(1,3-dimethyl-1H-1,2,4-triazol-5-yl)pyridine

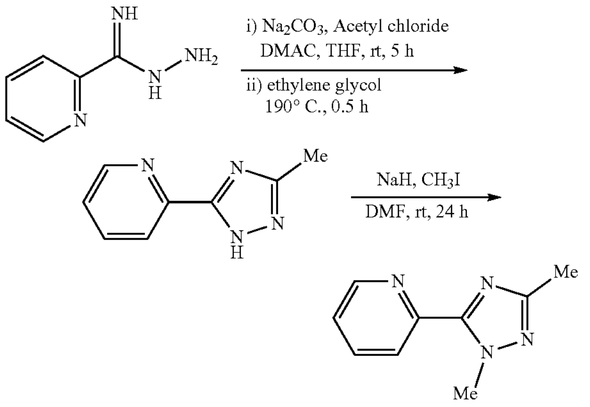

(Pyridin-2-yl)amidrazone prepared in 1) above 2.0 g (15 mmol) and sodium carbonate 1.6 g (15 mmol) were added in a 50 mL shrink flask, and dimethyl acetamide 15 mL and tetrahydrofuran 5 mL which were solvents were added and they were stirred at 0° C. Additionally, anhydrous dimethyl acetamide 5 mL and acetyl chloride 1.1 mL (15 mmol) were added to a 10 mL round bottom flask, and it was blocked with a rubber septa, and then it was dropped to the reaction mixture through a cannula under argon and it was stirred at a room temperature for 5 hours. After completing the reaction, the reaction mixture was filtered under reduced pressure to remove remaining solvents and it was washed with ethanol and distilled water to obtain a white solid. The white solid and ethylene glycol 20 mL were added in a 50 mL one-neck flask, and it was heated to 190° C. and stirred for 30 minutes. After completing the reaction, the reaction mixture was cooled to a room temperature and the ethylene glycol solvent was removed through distillation under reduced pressure to finally obtain 2-(5-R-2H-1,2,4-triazol-3-yl)pyridine of a yellow solid. (0.22 g, 9%)

2-(3-methyl-1H-1,2,4-triazol-5-yl)pyridine 0.22 g (1.4 mmol) was added in a 50 mL one-neck flask, and it was dissolved in anhydrous dimethyl formamide 5 mL in an argon gas atmosphere, and then sodium hydride 83 mg (2.0 mmol) was added. This reaction mixture was stirred to a room temperature for 20 minutes and iodomethane 0.3 g (2.0 mmol) was added in an argon gas atmosphere, and then it was stirred at a room temperature for 24 hours again. After completing the reaction, the reaction mixture was extracted with water (100 mL) and ethylacetate (100 mL×3). Organic layers were collected and concentrated under reduced pressure and purified by column chromatography using ethylacetate and hexane as developing solvents. (hexane:ethylacetate=7:3) Finally, 2-(1,3-dimethyl-1H-1,2,4-triazol-5-yl) pyridine was obtained. (83 mg, 34%)

3) Synthesis of $Os(Dmtz\text{-}py)_2Cl_2$ [Chemical formula 11]

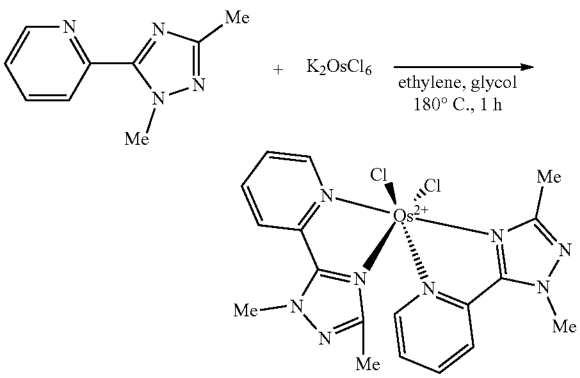

Potassium hexachloroosmate(IV) 14 mg (28.7 mmol) and 2-(1,3-dimethyl-1H-1,2,4-triazol-5-yl)pyridine 10 mg (57 umol) prepared in 2) above were added in a 5 mL Corn vial, and dissolved in 2 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (10 mL), thereby obtaining precipitates of the reduced osmium complex. The produced solid was filtered under reduced pressure and washed with water several times, and then dried in a vacuum oven of 40° C. to obtain a brown final compound osmium complex. (15 mg, 86%) HRMS ($^{192}Os$): m/z 610.0797([$M^+$] required 610.0792)

The entire preparation method of the compound of Chemical formula 11 is as the following Reaction formula 9.

[Reaction formula 9]

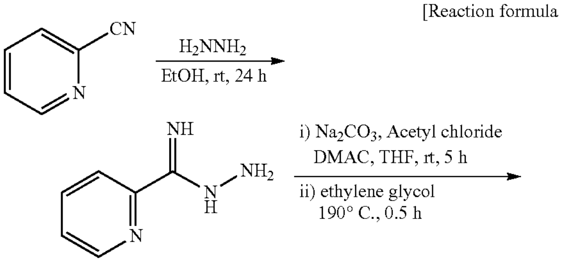

-continued

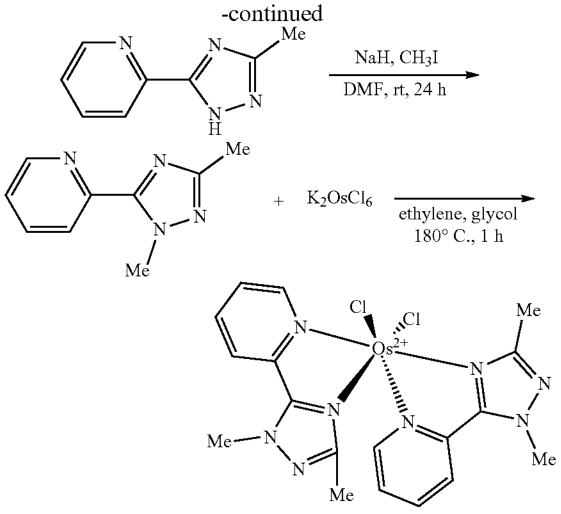

Example 1.10. Synthesis of Transition Metal Complex of Chemical Formula 12

1) Synthesis of 5-methyl-3-(pyridin-2-yl)-1,2,4-oxadiazole

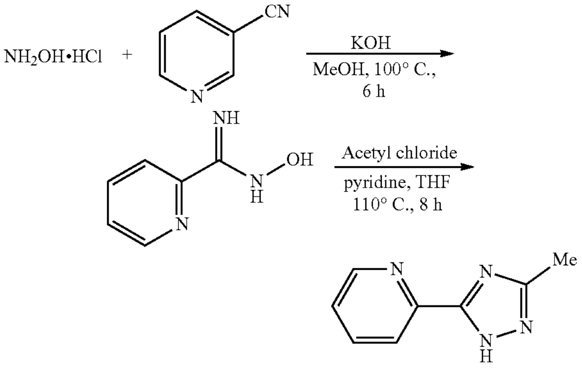

A reflux condenser and a gas inlet were equipped to a 250 mL two-neck round bottom flask, and ammonium hydroxyl chloride 7.0 g (0.1 mol) and potassium hydroxide 6.0 g (0.1 mol) were added in methanol 100 ml, and it was heated to 100° C. and stirred for 30 minutes. The produced potassium chloride was concentrated under reduced pressure and removed, and pyridine carbonitrile 7.0 g (60 mmol) was added to the filtered reaction solution and heated to 100° C., and stirred for 1 hour. After completing the reaction, the mixture was concentrated under reduced pressure and washed with distilled water to obtain hydroxy picolinimidamide of a transparent solid. (9.0 g, 65%)

A reflux condenser and a gas inlet were equipped to a 250 mL two-neck round bottom flask, and hydroxy picolinimidamide 1.0 g (7.3 mmol), pyridine 1.0 g (12.3 mmol), and acetyl chloride 0.7 g (8.8 mmol) were added to tetrahydrofuran 60 ml, and it was heated to 110° C. and stirred for 8 hours. After completing the reaction, the reaction mixture was cooled to a room temperature and extracted with water (100 mL) and ethylacetate (100 mL×3). Organic layers were concentrated under reduced pressure and after removing solvents, 5-methyl-3-(pyridin-2-yl)-1,2,4-oxadiazole of a transparent solid was obtained. (0.85 g, 72%)

2) Synthesis of $Os(Me\text{-}oxz\text{-}py)_2Cl_2$ [Chemical formula 12]

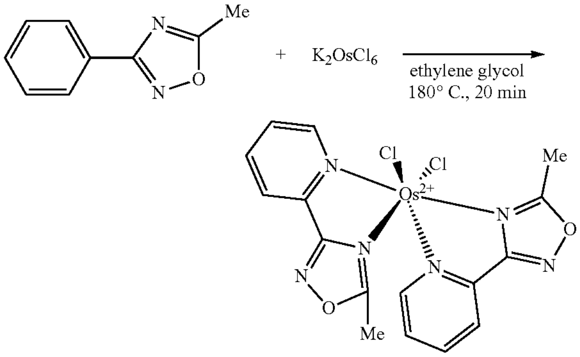

Potassium hexachloroosmate(IV) 0.6 g (1.4 mmol) and 5-methyl-3-(pyridin-2-yl)-1,2,4-oxadiazole 0.5 g (2.9 mmol) prepared in 1) above were added in a 250 mL shrink flask, and dissolved in 50 mL ethylene glycol in an argon gas atmosphere, and then argon degassing was performed for 15 minutes. This reaction mixture was heated to 180° C. and stirred for 20 minutes. After completing the reaction, the reaction mixture was cooled to a room temperature and produced red precipitates were filtered under reduced pressure and removed. The filtrate was dropped in a sodium dithionite 1.0 M aqueous solution (30 mL), thereby obtaining precipitates of the reduced osmium complex. The produced solid was filtered under reduced pressure and washed with water and acetonitrile several times, and then dried in a vacuum oven to obtain a yellow-brown final compound osmium complex. (0.6 g, 70%)

The entire preparation method of the compound of Chemical formula 12 is as the following Reaction formula 10.

[Reaction formula 10]

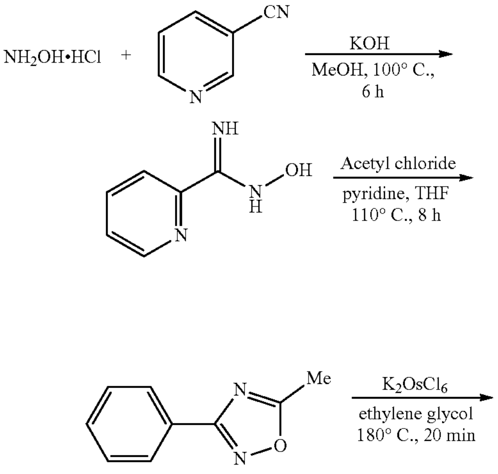

-continued

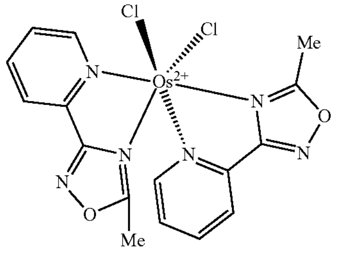

Example 1.11. Synthesis of Transition Metal Complex of Chemical Formula 13

1) Synthesis of 2-(1-butyl-1H-1,2,3-triazol-4-yl)pyridine

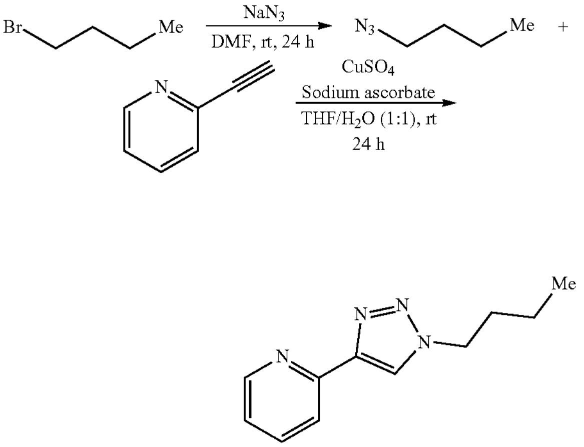

1-bromobutane 2.0 g (14 mmol) and sodium azide 0.9 g (14 mmol) were added in a 250 mL round bottom flask, and anhydrous dimethylformamide of 50 mL was added and it was stirred at a room temperature for 24 hours. After completing the reaction, this reaction mixture was extracted with water (100 mL) and diethylether (100 mL×3). Organic layers were collected and dried with magnesium sulfate, and concentrated under reduced pressure, and after removing solvents, without additional purification, the next reaction was progressed. 1-azidobutane and 2-ethynylpyridine 1.5 g (14 mmol) were added in a 250 mL two-neck round bottom flask, and tetrahydrofuran/water (40 mL/40 mL) was added and stirred at a room temperature. Sodium ascorbate 0.3 g (1.4 mmol) and copper sulfate 23 mg (0.14 mmol) were added to this reaction mixture, and argon degassing was performed for 15 minutes, and then it was stirred at a room temperature for 2 hours. After completing the reaction, the reaction mixture was extracted with water (100 mL) and ethylacetate (100 mL×3), and organic layers were collected and dried with magnesium sulfate. This solution was concentrated under reduced pressure and solvents were removed and it was purified by column chromatography using ethylacetate and hexane as developing solvents. (hexane:ethylacetate=1:4) Finally, 2-(1-(2-methoxyethynyl)-1H-1,2,3-triazol-4-yl)pyridine was obtained. (1.5 g, 52%)

2) Synthesis of $Os(3\text{-}Bu\text{-}tz\text{-}py)_2Cl_2$ [Chemical formula 13]

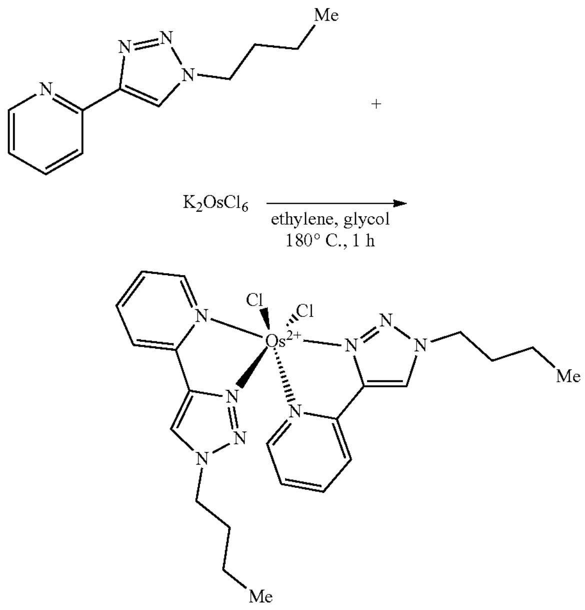

Potassium hexachloroosmate(IV) 0.5 g (1.0 mmol) and 2-(1-butyl-1H-1,2,3-triazol-4-yl)pyridine 0.4 g (2.0 mmol) prepared in 1) above were added in a 100 mL shrink flask, and dissolved in 15 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (200 mL), thereby obtaining precipitates of the reduced osmium complex. The produced solid was filtered under reduced pressure and washed with water several times, and then dried in a vacuum oven of 40° C. to obtain a final compound osmium complex. (0.4 g, 56%)

The entire preparation method of the compound of Chemical formula 13 is as the following Reaction formula 11.

[Reaction formula 11]

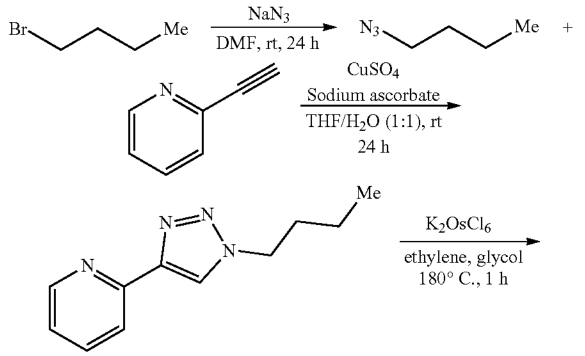

-continued

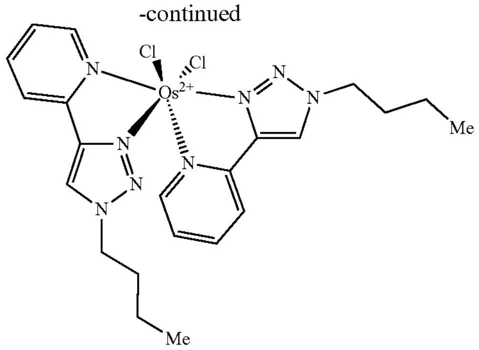

Example 1.12. Synthesis of Transition Metal Complex of Chemical Formula 14

1) Synthesis of 13-bromo-2,5,8,11-tetraoxatridecane

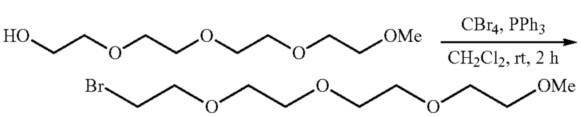

Tetraethylene glycol monomethyl ether 2.0 g (9.6 mmol) and tetrabromomethane 3.8 g (11.5 mmol) were added in a 250 mL round bottom flask, and dissolved in dichloromethane 50 mL, and then stirred at 0° C. using an ice tank. After that, during maintaining 0° C., triphenylphosphine 3.0 g (11.5 mmol) was subdivided for 15 minutes and slowly added and stirred at a room temperature for 2 hours. After completing the reaction, the reaction mixture was extracted with water (100 mL) and dichloromethane (100 mL×3). Organic layers were collected and concentrated under reduced pressure and purified by column chromatography using ethylacetate and hexane as developing solvents. (hexane:ethylacetate=2:1 (methanol 8%)) Finally, 13-bromo-2,5,8,11-tetraoxatridecane of yellow oil was obtained. (1.4 g, 54%)

2) Synthesis of 2-(1-(2,5,8,11-tetraoxatridecan-13-yl)-1H-1,2,3,-triazol-4-yl)pyridine

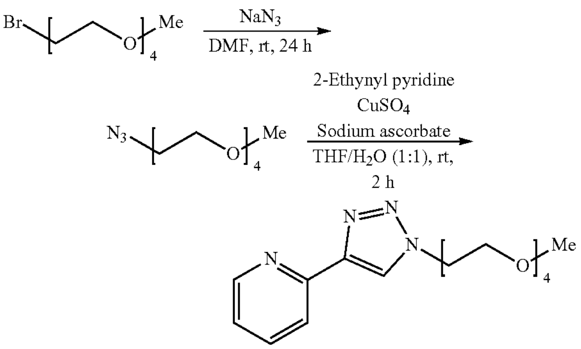

13-bromo-2,5,8,11-tetraoxatridecane 1.4 g (5.2 mmol) prepared in 1) above and sodium azide 0.34 g (5.2 mmol) were added in a 250 mL round bottom flask, and anhydrous dimethylformamide of 40 mL was added and stirred at a room temperature for 24 hours. After completing the reaction, this reaction mixture was extracted with water (100 mL) and diethylether (100 mL×3). Organic layers were collected and dried with magnesium sulfate, and concentrated under reduced pressure, and after removing solvents, without additional purification, the next reaction was progressed. 13-azido-2,5,8,11-tetraoxatridecane and 2-ethynylpyridine 0.8 g (7.7 mmol) were added in a 250 mL two-neck round bottom flask, and tetrahydrofuran/water (40 mL/40 mL) was added and stirred at a room temperature. Sodium ascorbate 0.15 g (0.8 mmol), and cooper sulfate 12 mg (0.08 mmol) were added to this reaction mixture and argon degassing was performed for 15 minutes, and then it was stirred at a room temperature for 2 hours. After completing the reaction, the reaction mixture was extracted with water (100 mL) and ethylacetate (100 mL×3), and organic layers were collected and layers were collected and dried with magnesium sulfate. This solution was concentrated under reduced pressure and solvents were removed, and it was purified by column chromatography using ethyl acetate and hexane as developing solvents. (hexane:ethylacetate=1:2 (methanol 5%)) Finally, 2-(1-(2,5,8,11-tetraoxatridecan-13-yl)-1H-1,2,3,-triazol-4-yl)pyridine was obtained. (0.86 g, 43%)

3) Synthesis of $Os(3\text{-}tz\text{-}teg\text{-}py)_2Cl_2$ [Chemical formula 14]

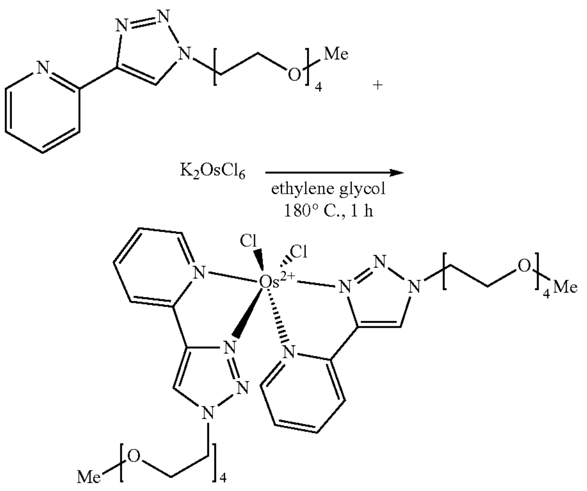

Potassium hexachloroosmate(IV) 0.1 g (0.21 mmol) and 2-(1-(2,5,8,11-tetraoxatridecan-13-yl)-1H-1,2,3,-triazol-4-yl)pyridine 0.14 g (0.42 mmol) prepared in 2) above were added in a 50 mL shrink flask, and dissolved in 15 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (10 mL), thereby obtaining precipitates of the reduced osmium complex. The produced solid was filtered under reduced pressure and washed with water several times, and then dried in a vacuum oven of 40° C. to obtain a black-purple final compound osmium complex. (0.1 g, 56%)

The entire preparation method of the compound of Chemical formula 14 is as the following Reaction formula 12.

[Reaction formula 12]

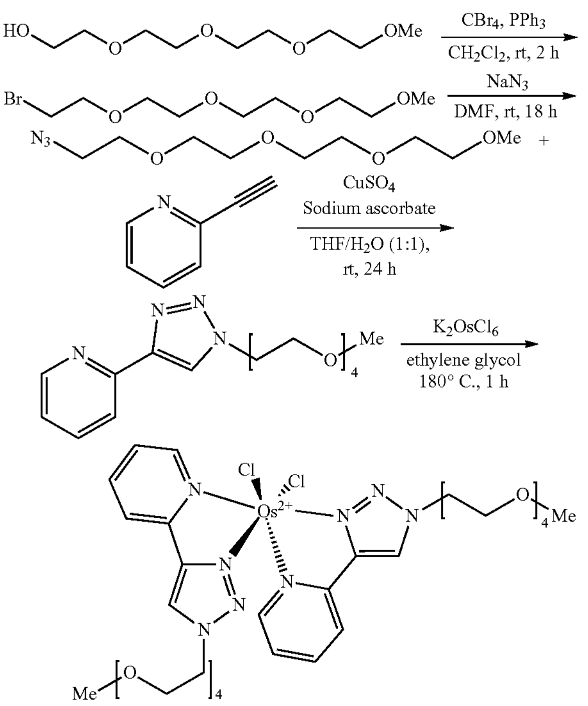

Example 1.13. Synthesis of Transition Metal Complex of Chemical Formula 15

1) Synthesis of 2-(1-(2-methoxyethynyl)-1H-1,2,3-triazol-4-yl)pyridine

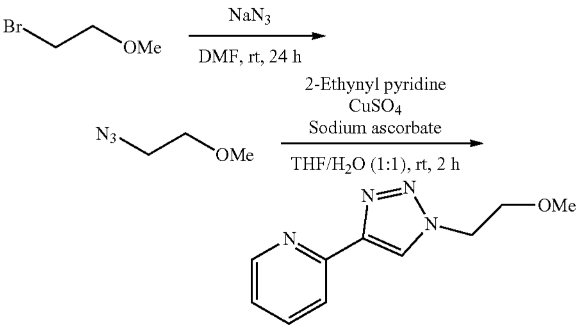

2-Bromoethyl methyl ether 2.0 g (14 mmol) and sodium azide 0.1 g (14 mmol) were added in a 250 mL round bottom flask, and anhydrous dimethylformamide of 50 mL was added and stirred at a room temperature for 24 hours. After completing the reaction, this reaction mixture was extracted with water (100 mL) and diethylether (100 mL×3). Organic layers were collected and concentrated under reduced pressure and after removing the solvent, without addition purification, the next reaction was progressed. 2-azidoethyl methyl ether and 2-ethynyl pyridine 1.5 g (14 mmol) were added in a 250 mL two-neck round bottom flask, and tetrahydrofuran/water (40 mL/40 mL) was added, and stirred at a room temperature. Sodium ascorbate 0.28 g (1.4 mmol) and copper sulfate 0.02 g (0.14 mmol) were added to this reaction mixture, and argon degassing was performed for 15 minutes, and then it was stirred at a room temperature for 2 hours. After completing the reaction, the reaction mixture was extracted with water (100 mL) and ethylacetate (100 mL×3). Organic layers were collected and dried with magnesium sulfate. This solution was concentrated under reduced pressured to remove solvents, and it was purified by column chromatography using ethylacetate and hexane as developing solvents. (hexane:ethylacetate=1:4) Finally, 2-(1-(2-methoxyethynyl)-1H-1,2,3-triazol-4-yl)pyridine was obtained. (1.5 g, 52%)

2) Synthesis of Os(3-mo-tz-py)$_2$Cl$_2$ [Chemical formula 15]

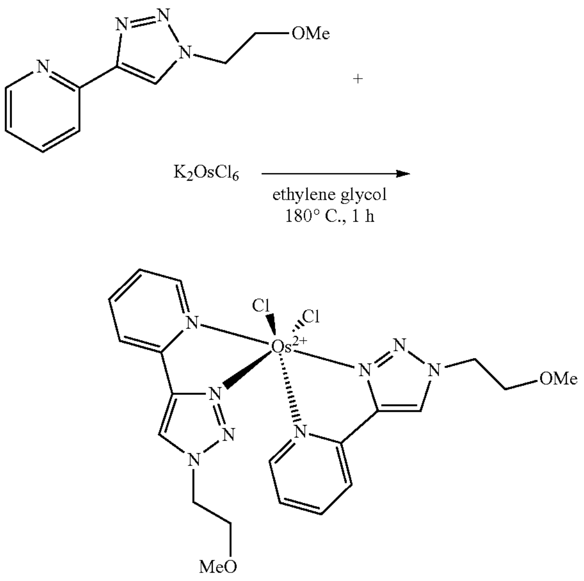

Potassium hexachloroosmate(IV) 0.5 g (1.0 mmol) and 2-(1-(2-methoxyethynyl)-1H-1,2,3-triazol-4-yl)pyridine 0.4 g (2.1 mmol) prepared in 1) above were added in a 100 mL shrink flask, and dissolved in 15 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (200 mL), thereby obtaining precipitates of the reduced osmium complex. The produced solid was filtered under reduced pressure and washed with water several times, and then dried in a vacuum oven of 40° C. to obtain a green final compound osmium complex. (0.4 g, 56%) HRMS ($^{192}$OS): m/z 670.09967([M$^+$] required 670.10)

The entire preparation method of the compound of Chemical formula 15 is as the following Reaction formula 13.

[Reaction formula 13]

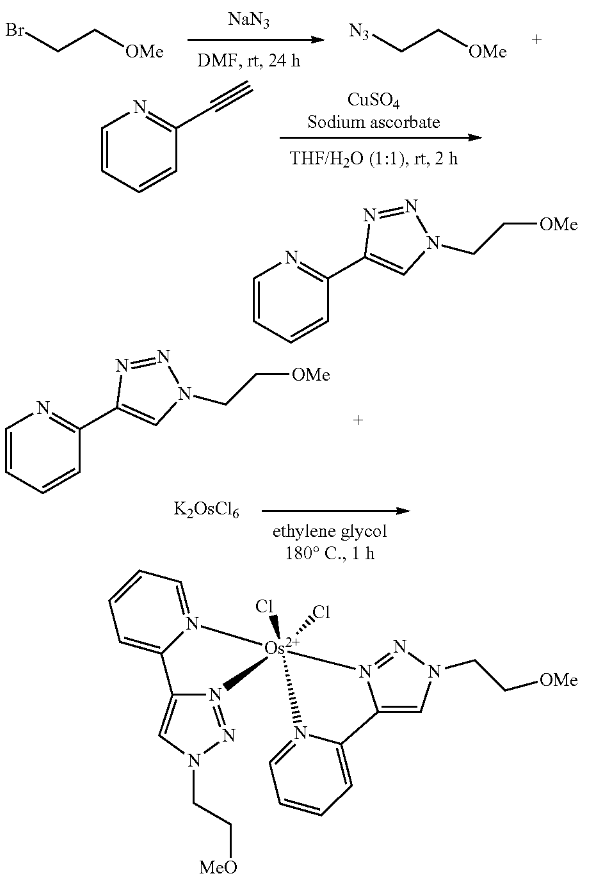

Example 1.14. Synthesis of Transition Metal Complex of Chemical Formula 16

1) Synthesis of 2-(1H-tetrazole-5-yl)pyridine

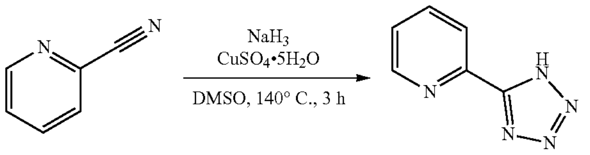 [SMILES: N#Cc1ccccn1 ; "NaH3CuSO4·5H2O" ; c1ccc(-c2nnn[nH]2)nc1]

A reflux condenser and a gas inlet were equipped to a 250 mL two-neck round bottom flask, and sodium azide 1.3 g (19.2 mmol), 2-ethynyl pyridine 2.0 g (19.2 mmol) and copper sulfate 96 mg (0.38 mmol) were added and dissolved in an anhydrous dimethylsulfoxide 40 mL in an argon gas atmosphere. For this reaction mixture, argon degassing was performed for 15 minutes, and then it was heated to 140° C. and stirred for 3 hours. After completing the reaction, the reaction mixture was cooled to a room temperature and extracted with water (100 mL) and ethylacetate (100 mL×3), and organic layers were collected and dried with magnesium sulfate. This solution was concentrated under reduced pressure to remove solvents, and finally, 2-(1H-tetrazole-5-yl) pyridine of a yellow solid was obtained. (1.1 g, 41%)

2) Synthesis of 2-(1-methyl-1H-tetrazole-5-yl)pyridine

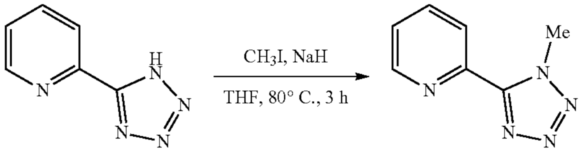

A reflux condenser and a gas inlet were equipped to a 100 mL two-neck round bottom flask, and 2-(1H-tetrazole-5-yl) pyridine 1.0 g (6.8 mmol) prepared in 1) above was added and dissolved in an anhydrous tetrahydrofuran (30 mL) in an argon gas atmosphere, and then sodium hydride 0.4 g (10 mmol) was added. This reaction mixture was stirred at a room temperature for 30 minutes, and iodomethane 1.5 g (10 mmol) was added in an argon gas atmosphere, and then it was heated to 80° C. and stirred for 3 hours. After completing the reaction, the reaction mixture was cooled to a room temperature and extracted with water (100 mL) and ethylacetate (100 mL×3). Organic layers were concentrated under reduced pressure and after removing the solvent, it was purified by column chromatography using ethylacetate and hexane as developing solvents. (hexane:ethylacetate=1:3) Finally, 2-(1-methyl-1H-tetrazole-5-yl)pyridine was obtained. (0.4 g. 40%)

3) Synthesis of Os(tetraz-py)$_2$Cl$_2$ [Chemical formula 16]

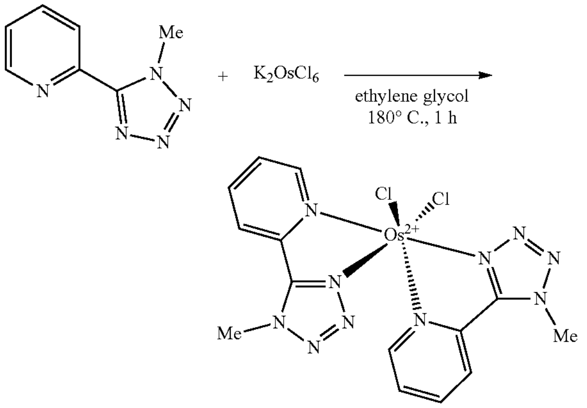

Potassium hexachloroosmate(IV) 0.10 g (0.21 mmol) and 2-(1-methyl-1H-tetrazole-5-yl)pyridine 0.7 g (0.42 mmol) prepared in 2) above were added in a 50 mL shrink flask, and dissolved in 5 mL ethylene glycol in an argon gas atmosphere, and then argon degassing was performed for 15 minutes. This reaction mixture was heated 15 to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (200 mL), thereby obtaining precipitates of the reduced osmium complex. The produced solid was filtered under reduced pressure and washed with water several times, and then dried in a vacuum oven of 40° C. to obtain a green final compound osmium complex. (0.1 g, 84%) HRMS ($^{192}$OS): m/z 584.0383([M$^+$] required 584.04)

The entire preparation method of the compound of Chemical formula 16 is as the following Reaction formula 14.

[Reaction formula 14]

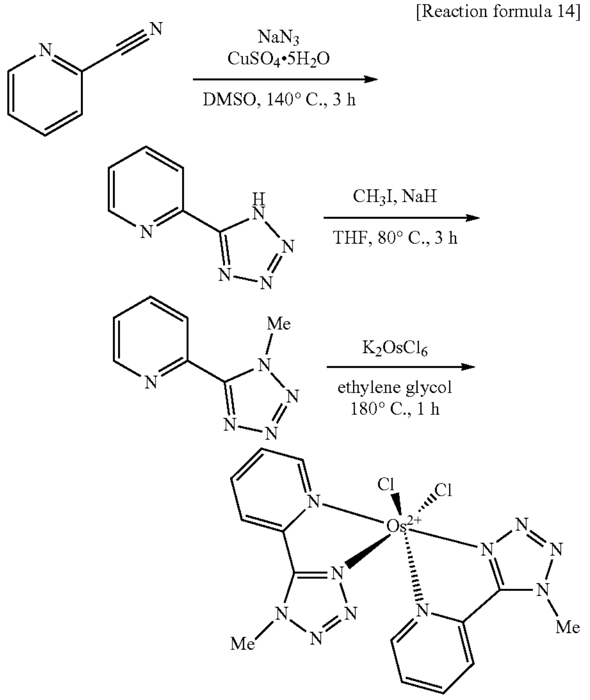

Example 1.15. Synthesis of Transition Metal Complex of Chemical Formula 17

1) Synthesis of 2-(1H-1,2,4-triazol-1-yl)pyridine

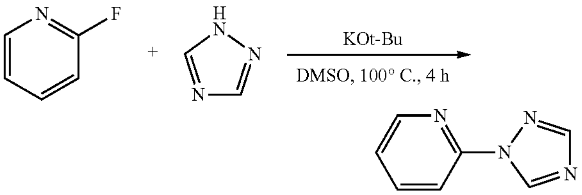

A reflux condenser and a gas inlet were equipped to a 250 mL two-neck round bottom flask, and 1H-1,2,4 triazole 3.0 g (43 mmol) and potassium tertiary butoxide 5.8 g (52 mmol) were added and dissolved in an anhydrous dimethylsulfoxide 40 mL in an argon gas atmosphere. 2-fluoropyridine 5.0 g (52 mmol) was added to this reaction mixture and heated to 100° C. in an argon gas atmosphere and stirred for 4 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=5:1) Finally, 2-(1H-1,2,4-triazol-1-yl)pyridine of a transparent solid was obtained. (4.3 g, 57%)

2) Synthesis of $Os(1,2,4tz\text{-}py)_2Cl_2$ [Chemical formula 17]

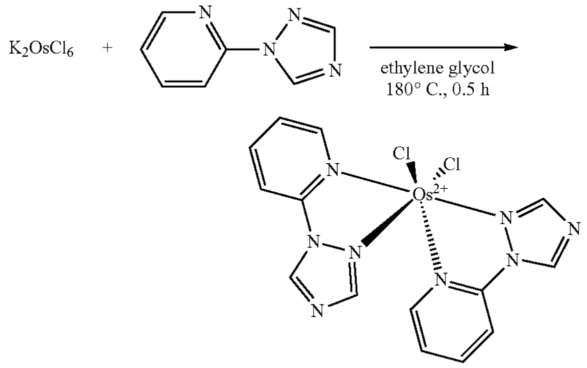

Potassium hexachloroosmate(IV) 0.6 g (1.4 mmol) and 2-(1H-1,2,4-triazol-1-yl)pyridine 0.4 g (2.9 mmol) prepared in 1) above were added in a 250 mL shrink flask, and dissolved in 50 mL ethylene glycol in an argon gas atmosphere, and then argon degassing was performed for 15 minutes. This reaction mixture was heated to 180° C. and stirred for 30 minutes. After completing the reaction, the reaction mixture was cooled to a room temperature and produced red precipitates were filtered under reduced pressure and removed. The filtrate was dropped in a sodium dithionite 1.0 M aqueous solution (30 mL), thereby obtaining precipitates of the reduced osmium complex. The produced solid was filtered under reduced pressure and washed with water and acetonitrile several times, and then dried in a vacuum oven to obtain a crimson final compound osmium complex. (0.3 g, 62%)

The entire preparation method of the compound of Chemical formula 17 is as the following Reaction formula 15.

[Reaction formula 15]

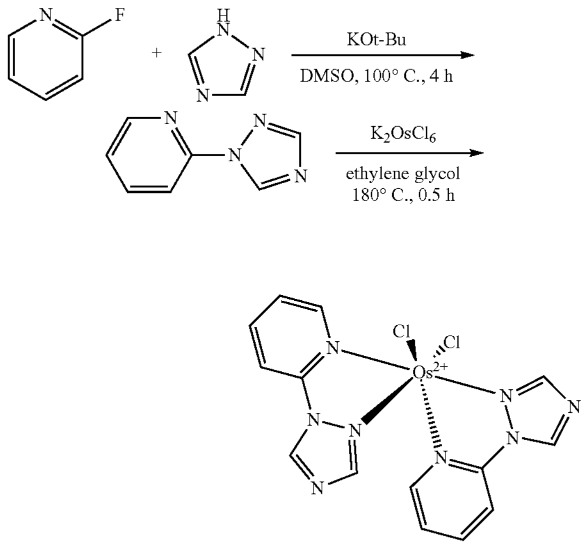

Example 1.16. Synthesis of Transition Metal Complex of Chemical Formula 18

1) Synthesis of 2-(1H-1,2,3-triazol-1-yl)pyridine

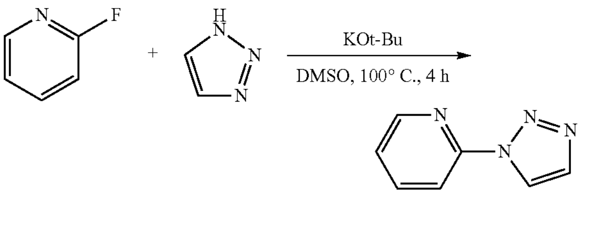

A reflux condenser and a gas inlet were equipped to a 250 mL two-neck round bottom flask, and 1H-1,2,3 triazole 3.0 g (43 mmol) and potassium tertiary butoxide 5.8 g (52 mmol) were added and dissolved in an anhydrous dimethylsulfoxide 40 mL in an argon gas atmosphere. 2-fluoropyridine 5.0 g (52 mmol) was added to this reaction mixture and heated to 100° C. in an argon gas atmosphere and stirred for 4 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=5:1) Finally, 2-(1H-1,2,3-triazol-1-yl)pyridine of a transparent solid was obtained. (3.5 g, 56%)

2) Synthesis of $Os(1,2,3tz\text{-}py)_2Cl_2$ [Chemical formula 18]

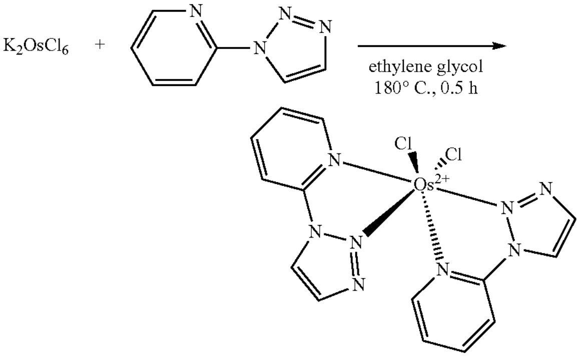

Potassium hexachloroosmate(IV) 0.6 g (1.4 mmol) and 2-(1H-1,2,3-triazol-1-yl)pyridine 0.4 g (2.9 mmol) prepared in 1) above were added in a 250 mL shrink flask, and dissolved in 50 mL ethylene glycol in an argon gas atmosphere, and then argon degassing was performed for 15 minutes. This reaction mixture was heated to 180° C. and stirred for 30 minutes. After completing the reaction, the reaction mixture was cooled to a room temperature and produced red precipitates were filtered under reduced pressure and removed. The filtrate was dropped in a sodium dithionite 1.0 M aqueous solution (30 mL), thereby obtaining precipitates of the reduced osmium complex. The produced solid was filtered under reduced pressure and washed with water and acetonitrile several times, and then dried in a vacuum oven to obtain a green final compound osmium complex. (0.4 g, 69%)

The entire preparation method of the compound of Chemical formula 18 is as the following Reaction formula 16.

[Reaction formula 16]

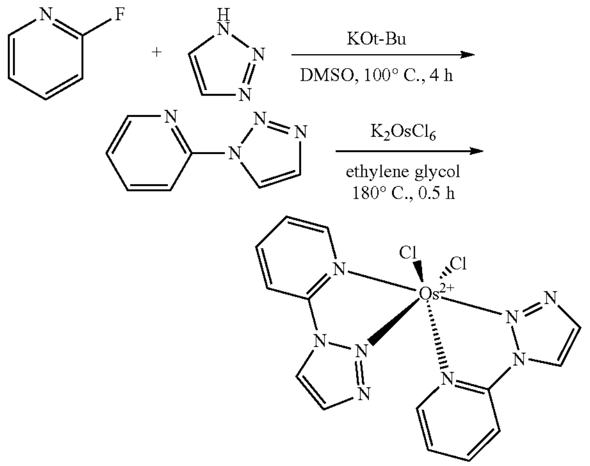

Example 1.17. Synthesis of Transition Metal Complex of Chemical Formula 19

1) Synthesis of 2-(1-methyl-1H-1,2,4-triazol-5-yl)pyridine

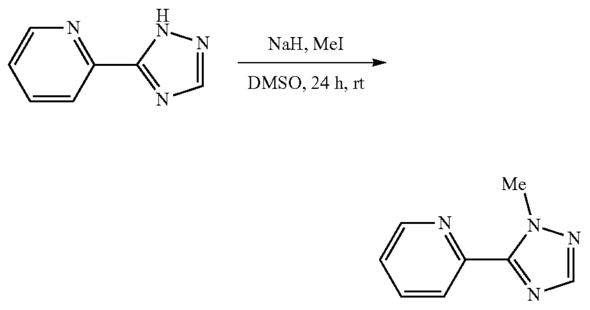

2-(1H-1,2,4-triazol-5-yl)pyridine 1.0 g (6.8 mmol) and sodium hydride 0.4 g (0.01 mmol) were added in a 100 mL two-neck round bottom flask, and dissolved in anhydrous dimethylsulfoxide 50 mL. Methyl iodide 1.4 g (0.01 mmol) was dropped in this reaction mixture using a dropping funnel, and stirred at a room temperature for 24 hours. After completion, the reaction mixture was extracted with water (100 mL) and ethylacetate (100 mL×3). Organic layers were collected and concentrated under reduced pressure, and after removing solvents, it was purified by column chromatography using ethylacetate and hexane as developing solvents. (hexane:ethylacetate=5:1) Finally, 2-(1-methyl-1H-1,2,4-triazol-5-yl)pyridine of a transparent solid was obtained. (0.9 g, 86%)

2) Synthesis of Os(4-Me-1,2,4tz-py)$_2$Cl$_2$ [Chemical formula 19]

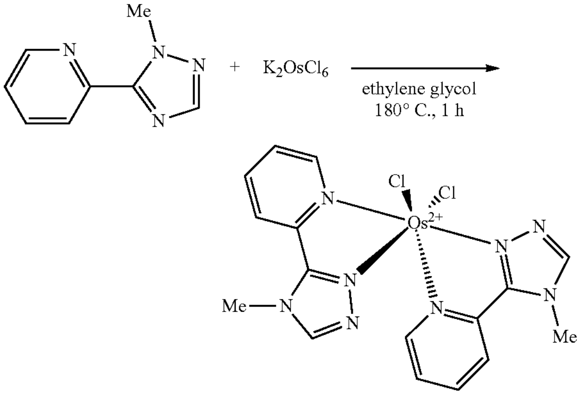

Potassium hexachloroosmate(IV) 0.6 g (1.4 mmol) and 2-(1-methyl-1H-1,2,4-triazol-5-yl)pyridine 0.5 g (2.9 mmol) prepared in 1) above were added in a 250 mL shrink flask, and dissolved in 50 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (30 mL), thereby obtaining precipitates of the reduced osmium complex. The produced solid was filtered under reduced pressure and washed with water and acetonitrile several times, and then dried in a vacuum oven to obtain a green final compound osmium complex. (0.2 g, 25%).

The entire preparation method of the compound of Chemical formula 19 is as the following Reaction formula 17.

[Reaction formula 17]

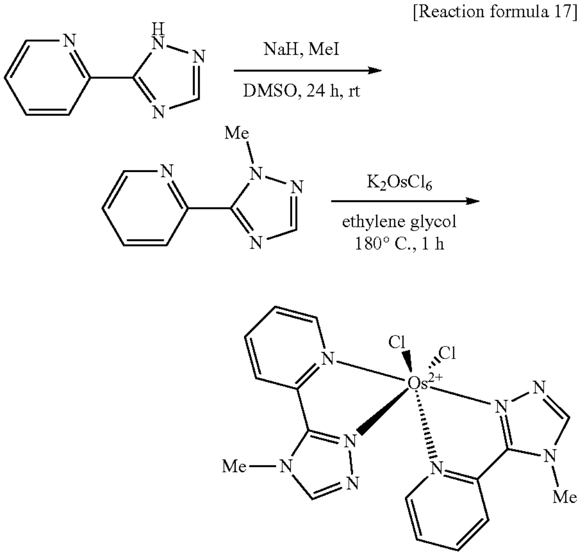

Example 1.18. Synthesis of Transition Metal Complex of Chemical Formula 20

1) Synthesis of 2-(3,4-dimethyl-1H-pyrazol-1-yl)-4-methylpyridine

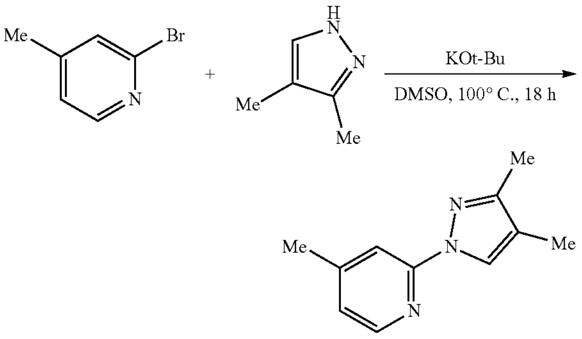

A reflux condenser and a gas inlet were equipped to a 250 mL two-neck round bottom flask, and 3,4-dimethylpyrazole 2.1 g (22 mmol) and potassium tertiary butoxide 2.5 g (22 mmol) were added and dissolved in an anhydrous dimethylsulfoxide 20 mL in an argon gas atmosphere. 2-bromo-4-methyl pyridine 3.5 g (20 mmol) was added to this reaction mixture and heated to 100° C. in an argon gas atmosphere and stirred for 18 hours. After completing the reaction, the reaction mixture was cooled to a room temperature and extracted with water (100 mL) and ethylacetate (100 mL×3). Organic layers were collected and concentrated under reduced pressure and after removing the solvent, it was purified by column chromatography using ethylacetate and hexane as developing solvents. (hexane:ethylacetate=3:1) Finally, 4-methyl-2-(3-methyl-1H-pyrazol-1-yl)pyridine of a transparent solid was obtained. (2.4 g, 63%)

2) Synthesis of Os(3,4-DiMe-pz-4-Me-py)$_2$Cl$_2$ [Chemical formula 20]

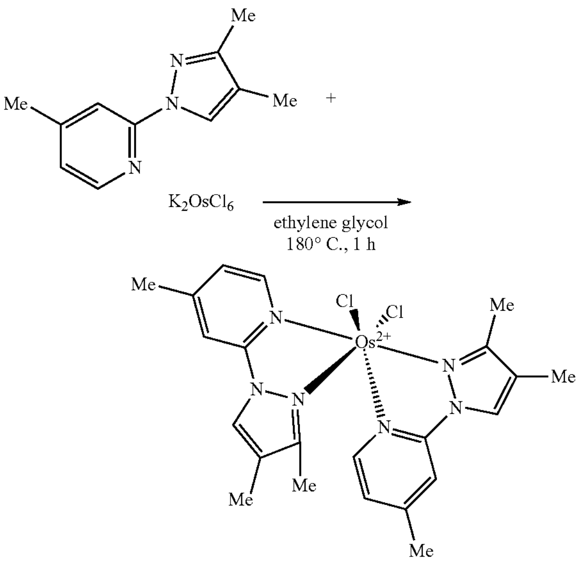

Potassium hexachloroosmate(IV) 0.5 g (1.0 mmol) and 2-(3,4-dimethyl-1H-pyrazol-1-yl)-4-methylpyridine 0.4 g (2.0 mmol) prepared in 1) above were added in a 50 mL shrink flask, and dissolved in 15 mL ethylene glycol in an argon gas atmosphere, and then argon degassing was performed for 15 minutes. This reaction mixture was heated to 180° C. and stirred for 1 hour. After completing the reaction, the reaction mixture was cooled to a room temperature and produced red precipitates were filtered under reduced pressure and removed. The filtrate was dropped in a sodium dithionite 1.0 M aqueous solution (100 mL), thereby obtaining precipitates of the reduced osmium complex. The produced solid was filtered under reduced pressure and washed with water and acetonitrile several times, and then dried in a vacuum oven to obtain a green final compound osmium complex. (0.4 g, 62%) HRMS ($^{192}$Os): m/z 636.1205([M$^+$] required 636.1200)

The entire preparation method of the compound of Chemical formula 20 is as the following Reaction formula 18.

[Reaction formula 18]

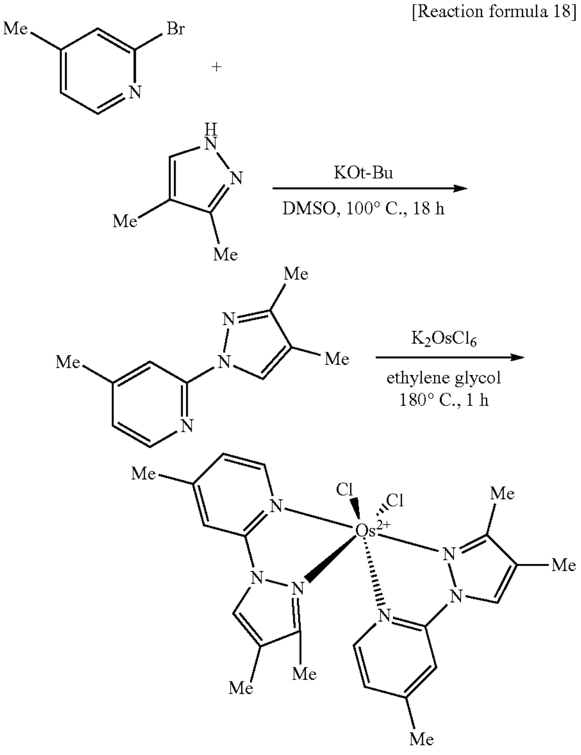

Example 1.19. Synthesis of Transition Metal Complex of Chemical Formula 21

1) Synthesis of 2-(3,4-dimethyl-1H-pyrazol-1-yl)-4-methoxypyridine

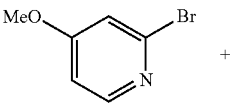

-continued

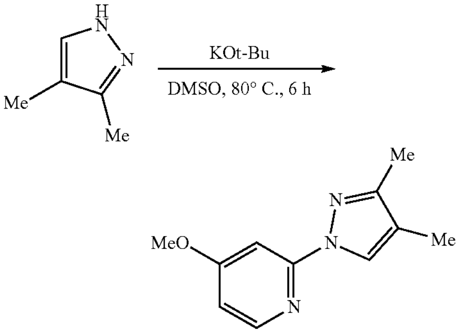

A reflux condenser and a gas inlet were equipped to a 50 mL two-neck round bottom flask, and 3,4-dimethylpyrazole 0.6 g (6 mmol) and potassium tertiary butoxide 0.7 g (6 mmol) were added and dissolved in an anhydrous dimethylsulfoxide 8 mL in an argon gas atmosphere. 2-bromo-4-methoxy pyridine 1.0 g (5. mmol) was added to this reaction mixture and heated to 80° C. in an argon gas atmosphere and stirred for 6 hours. After completing the reaction, the reaction mixture was cooled to a room temperature and extracted with water (50 mL) and ethylacetate (50 mL×3). Organic layers were collected and concentrated under reduced pressure and after removing the solvent, it was purified by column chromatography using ethylacetate and hexane as developing solvents. (hexane:ethylacetate=3:1) Finally, 4-methyl-2-(3-methyl-1H-pyrazol-1-yl)pyridine of a transparent solid was obtained. (0.4 g, 37%)

2) Synthesis of Os(3,4-DiMe-pz-4-MeO-py)$_2$Cl$_2$ [Chemical formula 21]

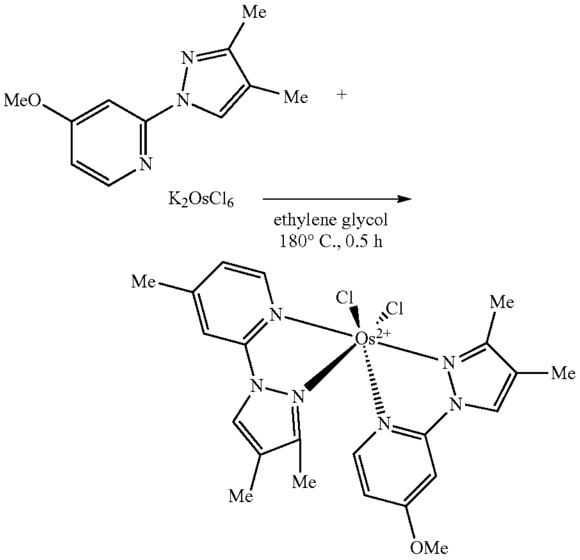

Potassium hexachloroosmate(IV) 0.5 g (1.0 mmol) and 2-(3,4-dimethyl-1H-pyrazol-1-yl)-4-methoxypyridine 0.4 g (2.0 mmol) prepared in 1) above were added in a 50 mL shrink flask, and dissolved in 15 mL ethylene glycol in an argon gas atmosphere, and then argon degassing was performed for 15 minutes. This reaction mixture was heated to 180° C. and stirred for 30 minutes. After completing the reaction, the reaction mixture was cooled to a room temperature and produced red precipitates were filtered under reduced pressure and removed. The filtrate was dropped in a sodium dithionite 1.0 M aqueous solution (100 mL), thereby obtaining precipitates of the reduced osmium complex. The produced solid was filtered under reduced pressure and washed with water and acetonitrile several times, and then dried in a vacuum oven to obtain a brown final compound osmium complex. (0.4 g, 64%) HRMS ($^{192}$Os): m/z 668.1103([M$^+$] required 668.1098)

The entire preparation method of the compound of Chemical formula 21 is as the following Reaction formula 19.

[Reaction formula 19]

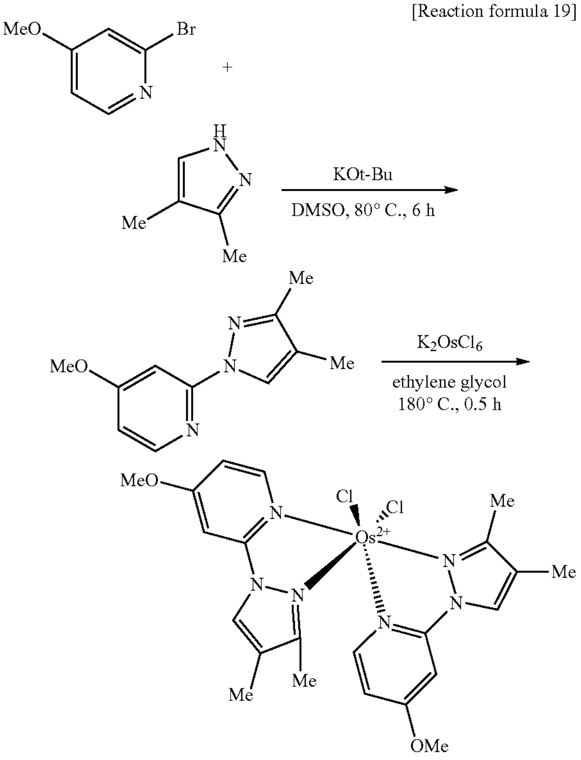

Example 1.20. Synthesis of Transition Metal Complex of Chemical Formula 22

1) Synthesis of N,N-dimethyl-2-(4-methyl-1H-pyrazol-1-yl)pyridine-4-amine

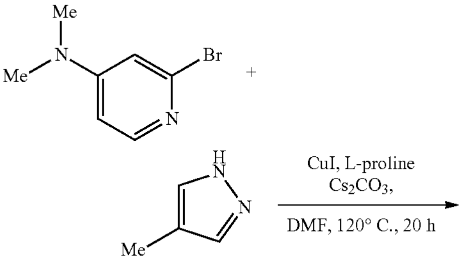

-continued

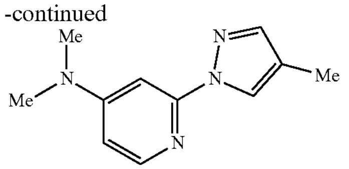

A reflux condenser and a gas inlet were equipped to a 50 mL two-neck round bottom flask, and 4-dimethylamino-2-bromo pyridine 1.0 g (5.0 mmol), 4-methylpyrazole 1.2 g (15 mmol), cooper iodide 0.14 g (0.75 mmol), L-proline 0.17 g (1.5 mmol) and cesium carbonate 4.1 g (12.5 mmol) were added and dissolved in an anhydrous dimethylformamide 20 mL in an argon gas atmosphere. This reaction mixture was heated to 120° C. and stirred for 20 hours. After completing the reaction, the reaction mixture was cooled to a room temperature and extracted with water (50 mL) and ethylacetate (50 mL×3). Organic layers were collected and concentrated under reduced pressure and after removing the solvent, it was purified by column chromatography using ethylacetate and hexane as developing solvents. (hexane: ethylacetate=5:1) Finally, N,N-dimethyl-2-(4-methyl-1H-pyrazol-1-yl)pyridine-4-amine of a white solid was obtained. (0.5 g, 50%)

2) Synthesis of Os(4-Me-pz-4-DiAM-py)$_2$Cl$_2$ [Chemical formula 22]

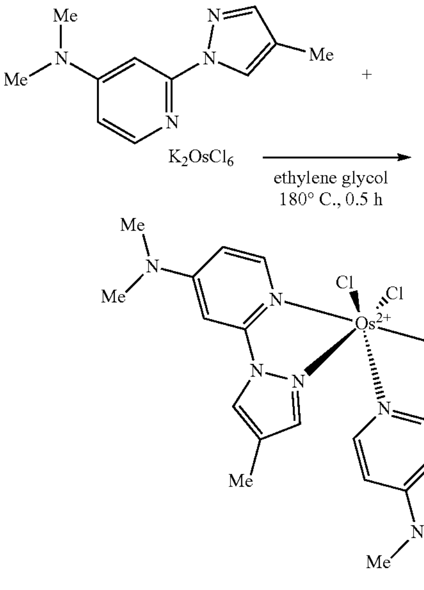

Potassium hexachloroosmate(IV) 0.6 g (1.2 mmol) and N,N-dimethyl-2-(4-methyl-1H-pyrazol-1-yl)pyridine-4-amine 0.5 g (2.4 mmol) prepared in 1) above were added in a 50 mL shrink flask, and dissolved in 15 mL ethylene glycol in an argon gas atmosphere, and then argon degassing was performed for 15 minutes. This reaction mixture was heated to 180° C. and stirred for 30 minutes. After completing the reaction, the reaction mixture was cooled to a room temperature and produced red precipitates were filtered under reduced pressure and removed. The filtrate was dropped in a sodium dithionite 1.0 M aqueous solution (100 mL), thereby obtaining precipitates of the reduced osmium complex. The produced solid was filtered under reduced pressure and washed with water and acetonitrile several times, and then dried in a vacuum oven to obtain a black-red final compound osmium complex. (0.5 g, 75%) HRMS ($^{192}$Os): m/z 666.1421([M$^+$] required 666.1418)

The entire preparation method of the compound of Chemical formula 22 is as the following Reaction formula 20.

[Reaction formula 20]

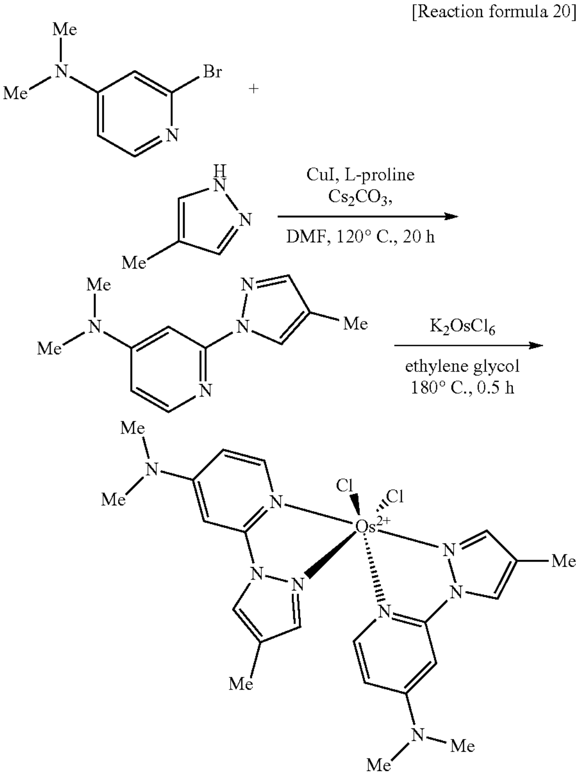

Example 1.21. Synthesis of Transition Metal Complex of Chemical Formula 23

1) Synthesis of Ru(DMSO)$_4$Cl$_2$ $RuCl_3$ x$H_2O$ —DMSO, 170° C., 0.5 h→ Ru(DMSO)$_4$Cl$_2$ $RuCl_3$*x$H_2O$ 0.9 g (4.3 mmol) and anhydrous dimethylsulfoxide (5 mL) were added in a 50 mL shrink flask and degassing was performed in an argon gas atmosphere for 10 minutes. This dark red suspension was heated to 170° C. and stirred for 30 minutes. After maintaining this temperature, until the color of this reaction solution was changed to dark yellow, the temperature was lowered to a room temperature to terminate the reaction. Acetone of 4 mL was added to this reaction solution and it was cooled to 0° C., and then left still for 4~5 hours. The produced solid was filtered under reduced pressure and washed with cool acetone. Finally, Ru(DMSO)$_4$Cl$_2$ of a yellow solid was obtained. Without additional purification, it was used for the next reaction. (1.5 g, 75%)

2) Synthesis of $Ru(pzpy)_2Cl_2$ [Chemical formula 23]

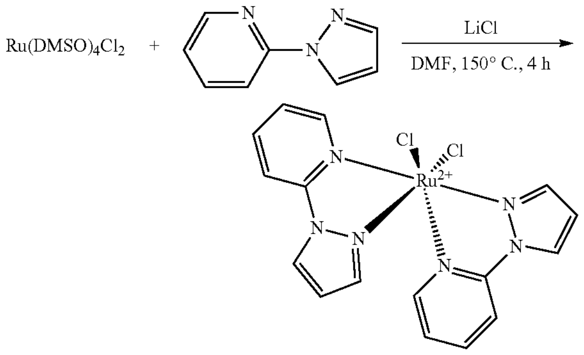

$Ru(DMSO)_4Cl_2$ 0.4 g (0.86 mmol), 2-(1H-pyrazol-1-yl) pyridine 0.25 g (1.7 mmol) prepared in the above experimental example, lithium chloride 1.8 g (43.0 mmol) and anhydrous dimethylformaide (15 mL) were added in a 50 mL shrink flask and degassing was performed for 10 minutes in an argon gas atmosphere. For light blocking, this reaction container was wrapped with aluminum foil and then it was stirred at 150° C. for 4 hours. After completing the reaction, acetone of 50 mL was added to the dark purple reaction solution and cooled at 0° C. for 24 hours. The black-purple solid was filtered under reduced pressure, and for removal of lithium chloride and by-products, it was washed with acetone until the color of the filtrate became transparent. The remaining dark purple solid was dried in a vacuum oven to obtain a final compound ruthenium complex. After that, it was left still for 4~5 hours. The produced solid was filtered under reduced pressure and washed with cold acetone. Finally, $Ru(DMSO)_4Cl_2$ of a yellow solid was obtained. (0.25 g, 55%) HRMS: m/z 461.9710([$M^+$] required 461.9690)

The entire preparation method of the compound of Chemical formula 23 is as the following Reaction formula 21.

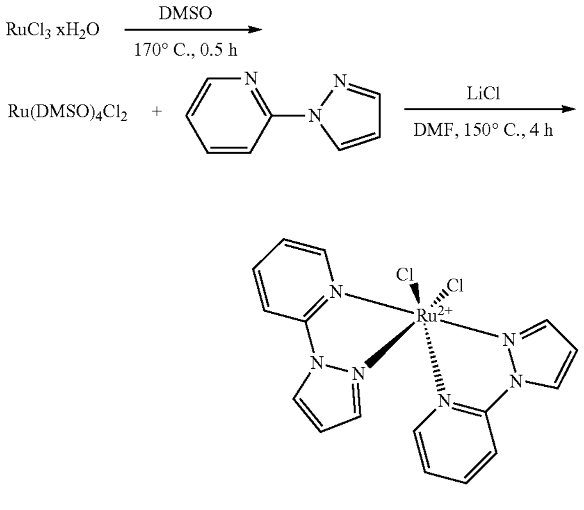

Example 1.22. Synthesis of Transition Metal Complex of Chemical Formula 24

1) Synthesis of $Ru(4\text{-}Me\text{-}pz4\text{-}Me\text{-}py)_2Cl_2$ [Chemical formula 24]

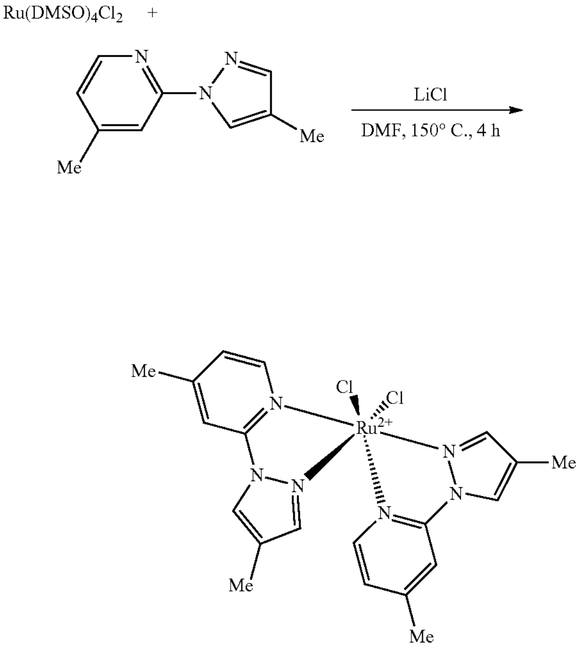

$Ru(DMSO)_4Cl_2$ 0.4 g (0.86 mmol), 4-methyl-2-(4-methyl-1H-pyrazol-1-yl)pyridine 0.3 g (1.7 mmol) prepared in the above experimental example, lithium chloride 1.8 g (43.0 mmol) and anhydrous dimethylformaide (15 mL) were added in a 50 mL shrink flask and degassing was performed for 10 minutes in an argon gas atmosphere. For light blocking, this reaction container was wrapped with aluminum foil and then it was stirred at 150° C. for 4 hours. After completing the reaction, acetone of 50 mL was added to the dark purple reaction solution and cooled at 0° C. for 24 hours. The black-purple solid was filtered under reduced pressure, and for removal of lithium chloride and by-products, it was washed with acetone until the color of the filtrate became transparent. The remaining dark purple solid was dried in a vacuum oven to obtain a final compound ruthenium complex. (0.1 g, 23%) HRMS: m/z 518.0321 ([$M^+$] required 518.0316)

The entire preparation method of the compound of Chemical formula 24 is as the following Reaction formula 22.

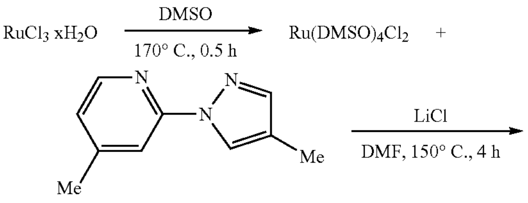

-continued

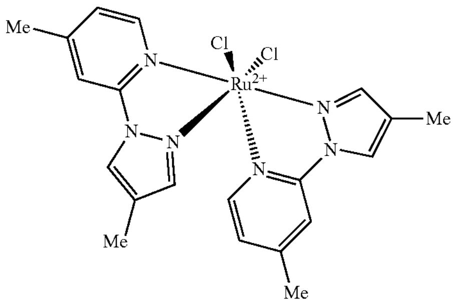

Example 1.23. Synthesis of Transition Metal Complex of Chemical Formula 25

1) Synthesis of $Fe(pzpy)_2Cl_2$ [Chemical formula 25]

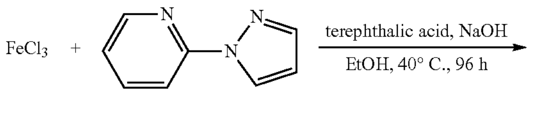

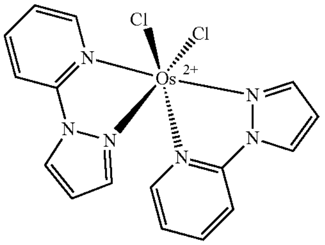

$FeCl_3$ 1.6 g (10.0 mmol), 2-(1H-pyrazol-1-yl)pyridine 1.5 g (10.0 mmol) prepared in the experimental example, terephthalic acid 3.3 g (20.0 mmol), sodium hydroxide 0.8 g (20 mmol) and anhydrous ethanol (30 mL) were added in a 100 mL shrink flask, and degassing was performed in an argon gas atmosphere for 10 minutes. This reaction solution was stirred at 50° C. for 96 hours. After completing the reaction, the temperature was lowered to a room temperature, and the produced black-red solid was filtered under reduced pressure and washed with acetone. The black-red solid was dried in a vacuum oven to obtain a final compound iron complex. (1.0 g, 24%) HRMS: m/z 415.9971 ([M+] required 415.9995)

Example 2: Synthesis of Oxidation-Reduction Polymer Comprising the Transition Metal Complex According to the Present Invention

Example 2.1. Synthesis of Oxidation-Reduction Polymer of Chemical Formula 28

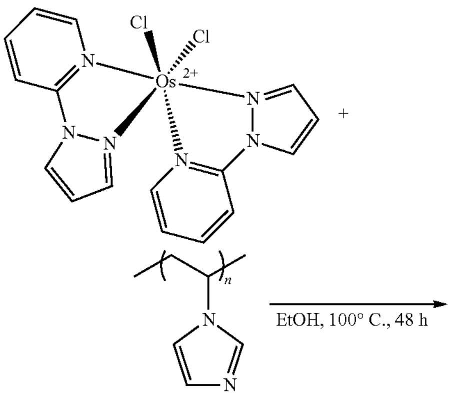

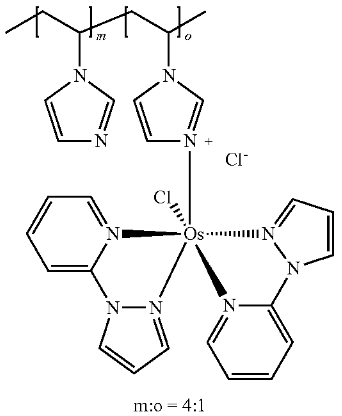

m:o = 4:1

A reflux condenser, a gas inlet and a thermometer were equipped to a 100 mL three-neck round bottom flask, and $Os(pzpy)_2Cl_2$ [Chemical formula 3] 0.12 g (0.22 mmol) prepared in Example 1.1. was added and completely dissolved in ethanol 10 mL in an argon gas atmosphere. Polyvinyl imidazole (Mn=10,000 g/mol) 0.1 g completely dissolved in ethanol 20 mL was added to this reaction mixture and heated to 100° C. and stirred for 2 days. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—$Os(pzpy)_2Cl$) of Chemical formula 25 of 0.2 g. (0.20 g, 91%)

Example 2.2. Synthesis of Oxidation-Reduction Polymer of Chemical Formula 29

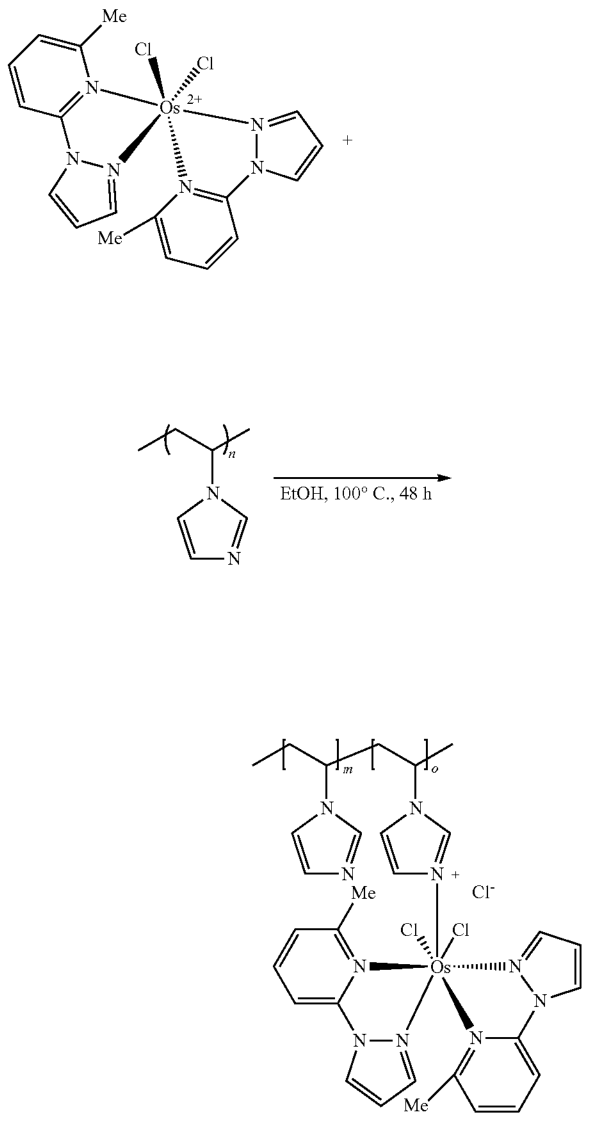

m:o = 4:1

A reflux condenser, a gas inlet and a thermometer were equipped to a 100 mL three-neck round bottom flask, and $Os(pz\text{-}2\text{-}Me\text{-}py)_2Cl_2$ [Chemical formula 4] 0.13 g (0.22 mmol) prepared in Example 1.2. was added and completely dissolved in ethanol 10 mL in an argon gas atmosphere. Polyvinyl imidazole (Mn=10,000 g/mol) 0.1 g completely dissolved in ethanol 20 mL was added to this reaction mixture and heated to 100° C. and stirred for 2 days. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—$Os(pz\text{-}2\text{-}Mepy)_2Cl$) of Chemical formula 26 of 0.2 g. (0.20 g, 87%)

Example 2.3. Synthesis of Oxidation-Reduction Polymer of Chemical Formula 30

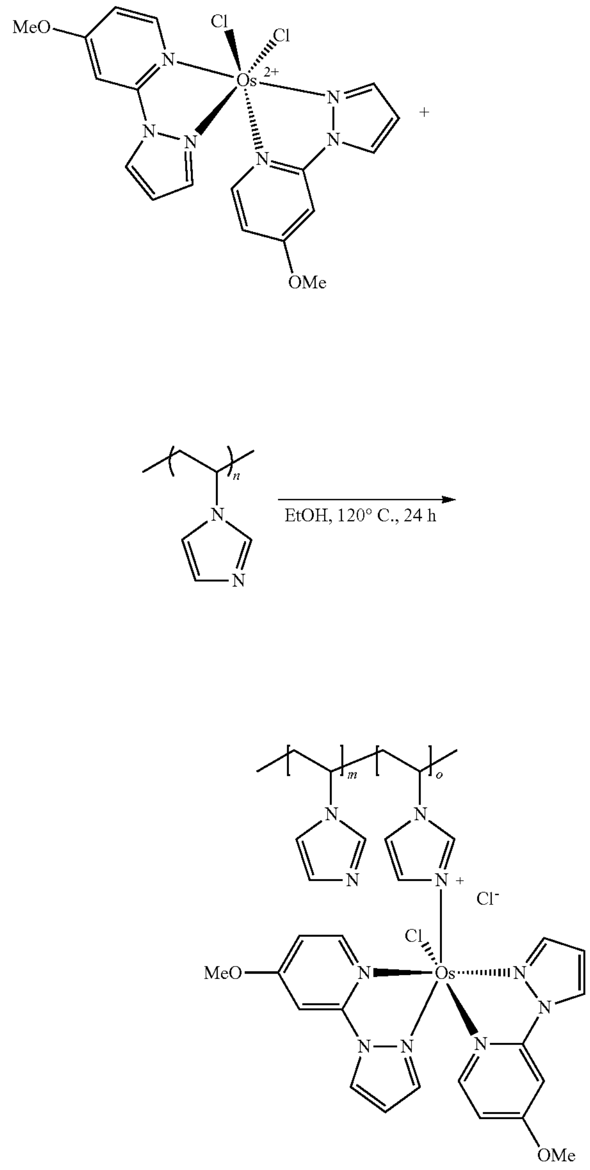

m:o = 4:1

$Os(pz\text{-}4\text{-}MeO\text{-}py)_2Cl_2$ [Chemical formula 5] 0.13 g (0.22 mmol) prepared in Example 1.3. was added in a 100 mL shrink flask and completely dissolved in ethanol 10 mL in an argon gas atmosphere. Polyvinyl imidazole (Mn=10,000 g/mol) 0.1 g completely dissolved in ethanol 20 mL was added to this reaction mixture and heated to 120° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—$Os(pz\text{-}4\text{-}MeO\text{-}py)_2Cl$) of Chemical formula 27 of 0.2 g. (0.21 g, 89%)

Example 2.4. Synthesis of Oxidation-Reduction Polymer of Chemical Formula 31

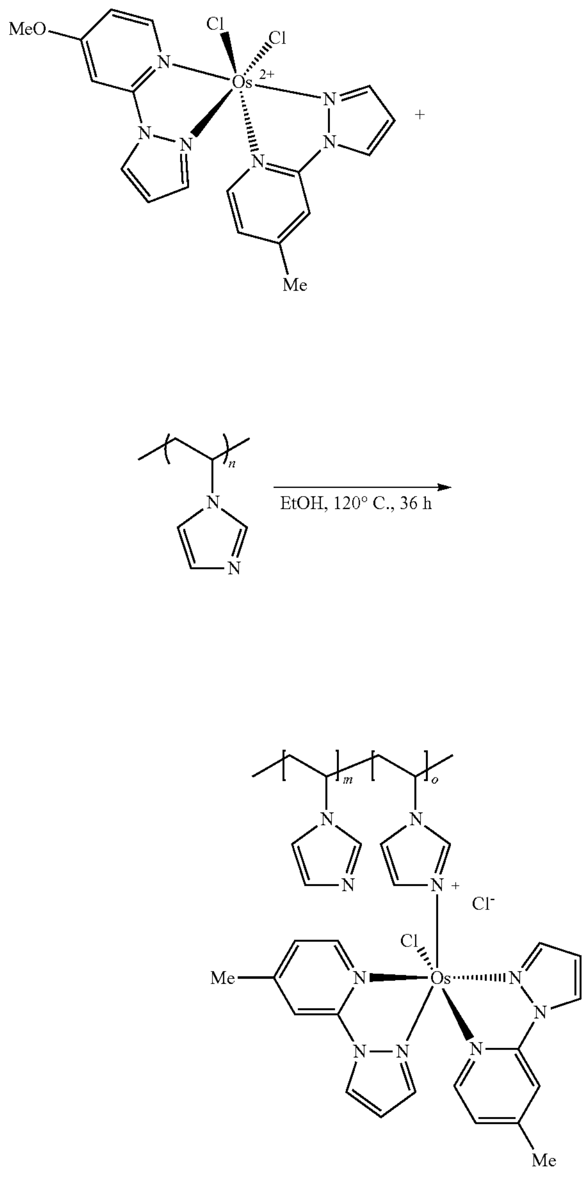

m:o = 3:1

Os(pz-4-Me-py)$_2$Cl$_2$ [Chemical formula 6] 0.31 g (0.53 mmol) prepared in Example 1.4. was added in a 100 mL shrink flask and completely dissolved in ethanol 10 mL in an argon gas atmosphere. Polyvinyl imidazole (Mn=10,000 g/mol) 0.2 g completely dissolved in ethanol 30 mL was added to this reaction mixture and heated to 120° C. and stirred for 36 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—Os(pz-4-Me-py)$_2$ Cl) of Chemical formula 28 of 0.4 g. (0.4 g, 78%)

Example 2.5 Synthesis of Oxidation-Reduction Polymer of Chemical Formula 32

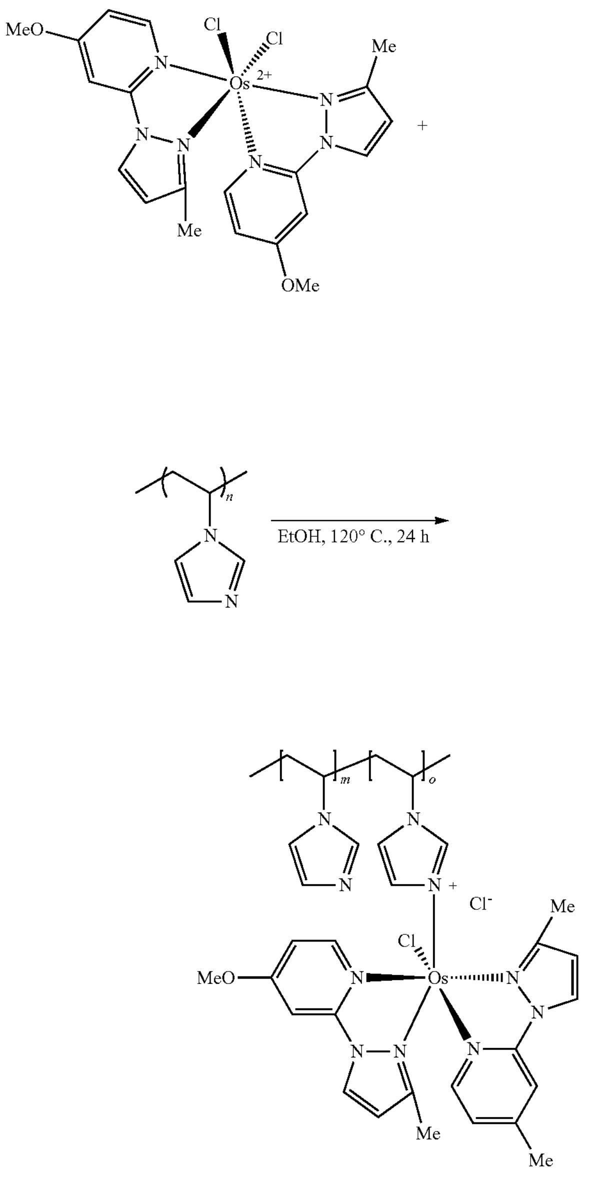

m:o = 4:1

Os(3-Me-pz-4-Me-py)$_2$Cl$_2$ [Chemical formula 7] 0.27 g (0.44 mmol) prepared in Example 1.5. was added in a 100 mL shrink flask and completely dissolved in ethanol 20 mL in an argon gas atmosphere. Polyvinyl imidazole (Mn=10, 000 g/mol) 0.2 g completely dissolved in ethanol 30 mL was added to this reaction mixture and heated to 120° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—Os(3-Me-pz-4-Me-py)$_2$Cl) of Chemical formula 29 of 0.4 g. (0.41 g, 87%)

Example 2.6. Synthesis of Oxidation-Reduction Polymer of Chemical Formula 33

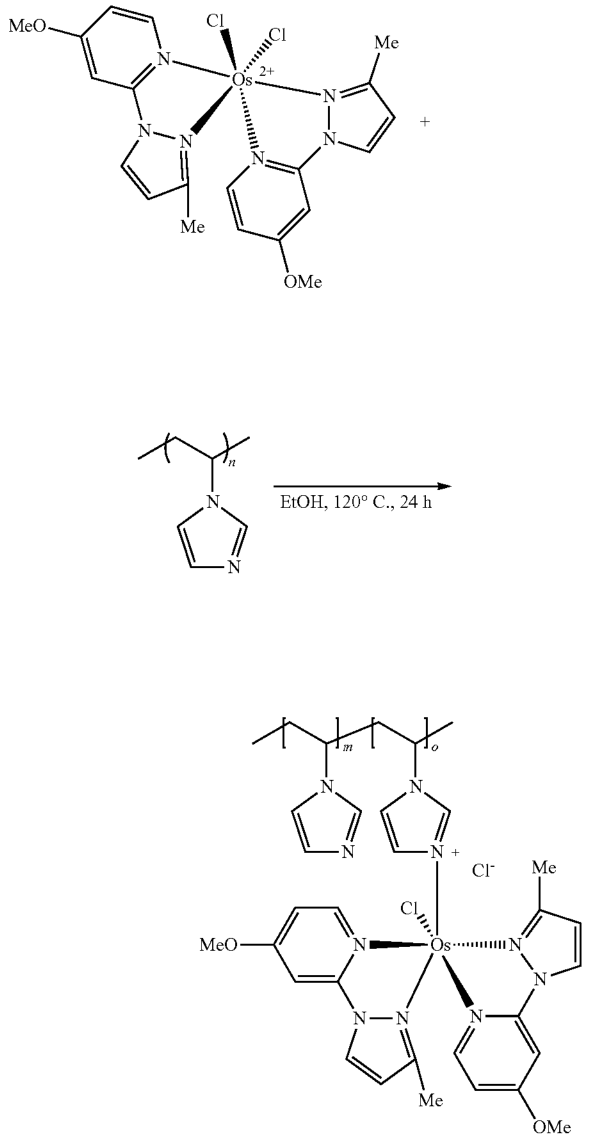

m:o = 4:1

Os(3-Me-pz-4-MeO-py)$_2$Cl$_2$ [Chemical formula 8] 0.14 g (0.22 mmol) prepared in Example 1.6. was added in a 100 mL shrink flask and completely dissolved in ethanol 10 mL in an argon gas atmosphere. Polyvinyl imidazole (Mn=10,000 g/mol) 0.1 g completely dissolved in ethanol 20 mL was added to this reaction mixture and heated to 120° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—Os(3-Me-pz-4-MeO-py)$_2$Cl) of Chemical formula 30 of 0.22 g. (0.22 g, 92%)

Example 2.7. Synthesis of Oxidation-Reduction Polymer of Chemical Formula 34

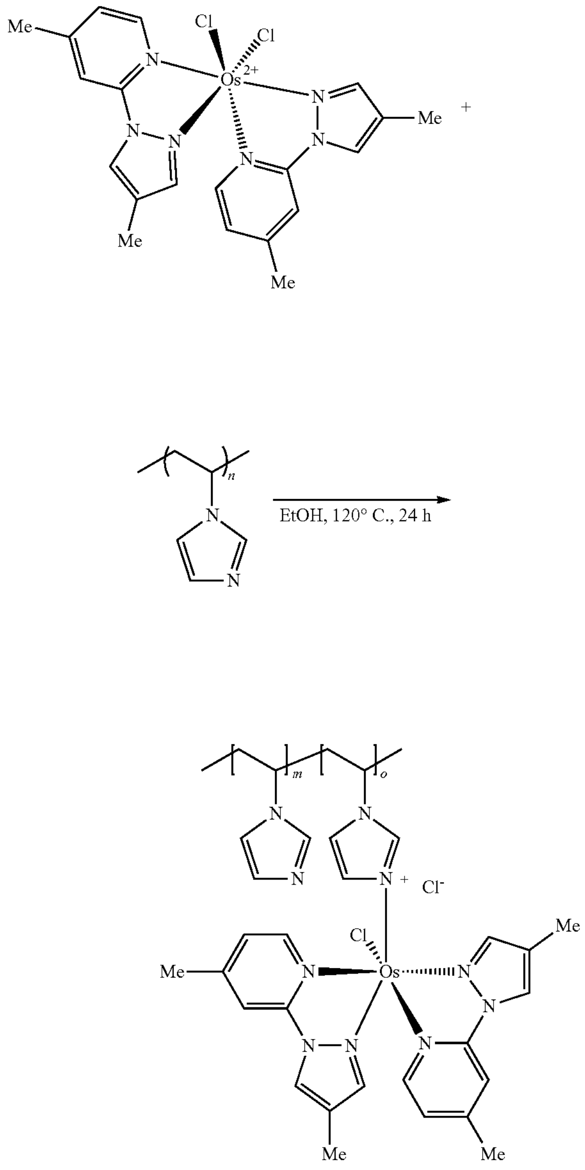

m:o = 4:1

Os(4-Me-pz-4-Me-py)$_2$Cl$_2$ [Chemical formula 9] 0.8 g (1.32 mmol) prepared in Example 1.7. was added in a 250 mL shrink flask and completely dissolved in ethanol 50 mL in an argon gas atmosphere. Polyvinyl imidazole (Mn=10,000 g/mol) 0.5 g completely dissolved in ethanol 50 mL was added to this reaction mixture and heated to 120° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—Os(4-Me-pz-4-Me-py)$_2$Cl) of Chemical formula 31 of 1.21 g. (1.21 g, 93%)

Example 2.8. Synthesis of Oxidation-Reduction Polymer of Chemical Formula 35

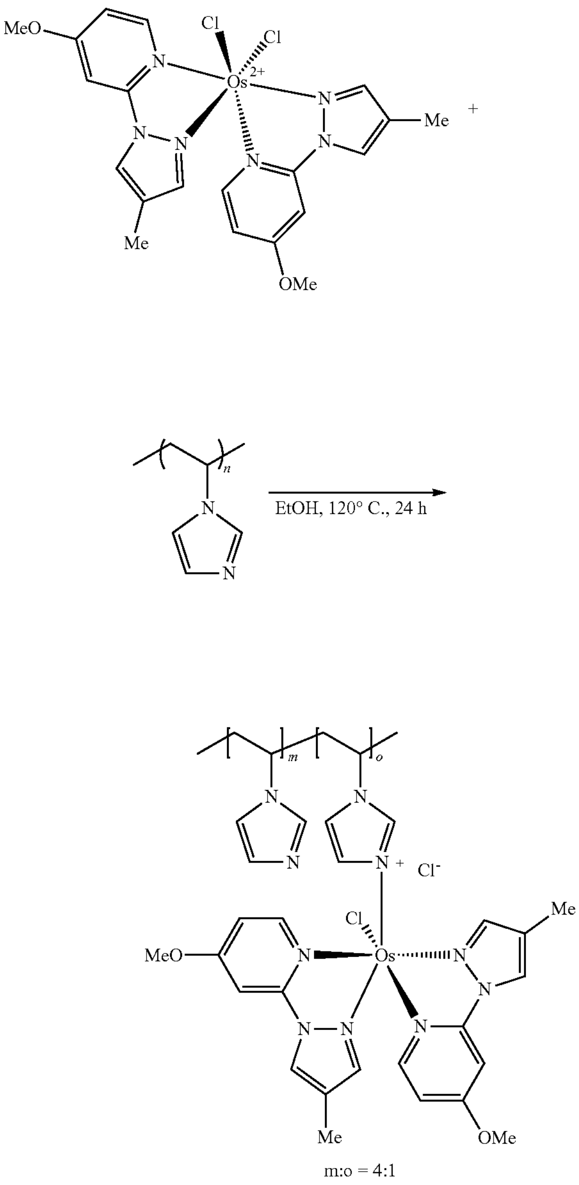

$Os(4\text{-}Me\text{-}pz\text{-}4\text{-}MeO\text{-}py)_2Cl_2$ [Chemical formula 10] 0.14 g (0.22 mmol) prepared in Example 1.8. was added in a 100 mL shrink flask and completely dissolved in ethanol 10 mL in an argon gas atmosphere. Polyvinyl imidazole (Mn=10, 000 g/mol) 0.1 g completely dissolved in ethanol 20 mL was added to this reaction mixture and heated to 120° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer ($PVI—Os(4\text{-}Me\text{-}pz\text{-}4\text{-}MeO\text{-}py)_2Cl$) of Chemical formula 32 of 0.20 g. (0.20 g, 83%)

Example 2.9. Synthesis of Oxidation-Reduction Polymer of Chemical Formula 36

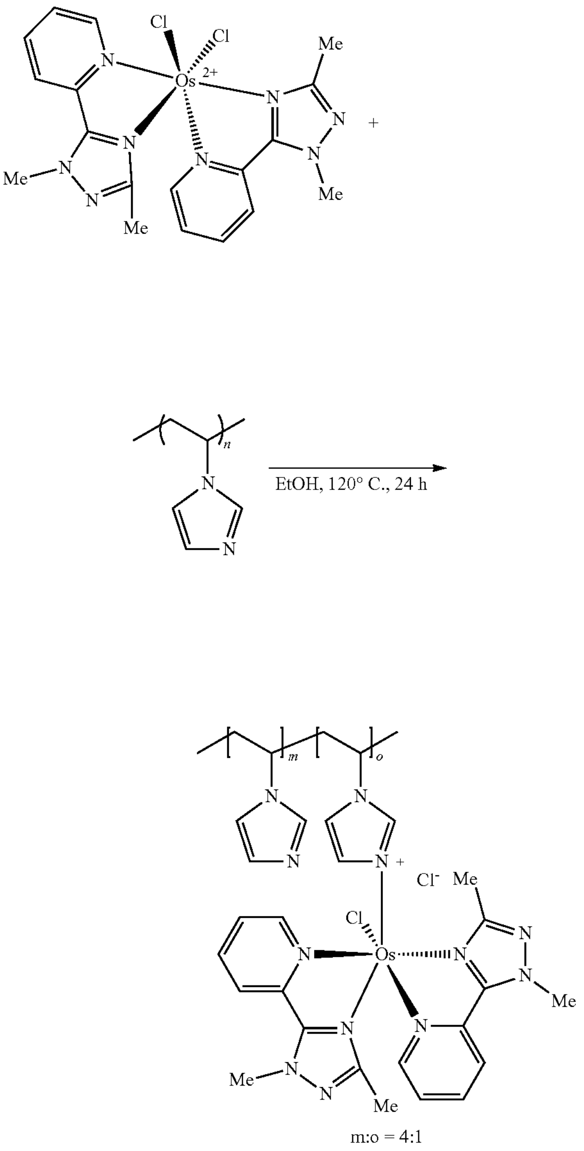

A reflux condenser, a gas inlet and a thermometer were equipped to a 100 mL three-neck round bottom flask, and $Os(Dmtz\text{-}py)_2Cl_2$ [Chemical formula 11] 0.13 g (0.22 mmol) prepared in Example 1.9. was added and completely dissolved in ethanol 10 mL in an argon gas atmosphere. Polyvinyl imidazole (Mn=10,000 g/mol) 0.1 g completely dissolved in ethanol 20 mL was added to this reaction mixture and heated to 100° C. and stirred for 2 days. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a brown oxidation-reduction polymer ($PVI—Os(Dmtz\text{-}py)_2Cl$) of Chemical formula 33 of 0.15 g. (0.15 g, 65%)

Example 2.10. Synthesis of Oxidation-Reduction Polymer of Chemical Formula

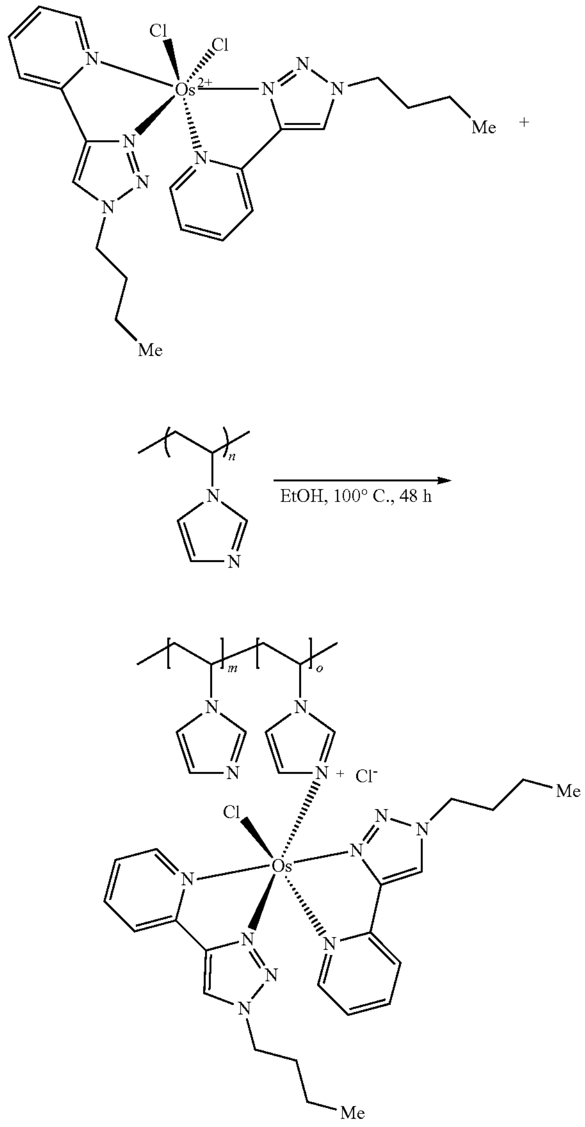

m:o = 4:1

A reflux condenser, a gas inlet and a thermometer were equipped to a 100 mL three-neck round bottom flask, and Os(3-Bu-tz-py)$_2$Cl$_2$ [Chemical formula 13] 0.12 g (0.18 mmol) prepared in Example 1.11. was added and completely dissolved in ethanol 10 mL in an argon gas atmosphere. Polyvinyl imidazole (Mn=10,000 g/mol) 85 mg completely dissolved in ethanol 20 mL was added to this reaction mixture and heated to 100° C. and stirred for 2 days. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a red PVI—Os polymer (PVI—Os (3-Bu-tz-py)$_2$Cl) of Chemical formula 34 of 0.2 g. (0.2 g. 95%)

Example 2.11. Synthesis of Oxidation-Reduction Polymer of Chemical Formula 38

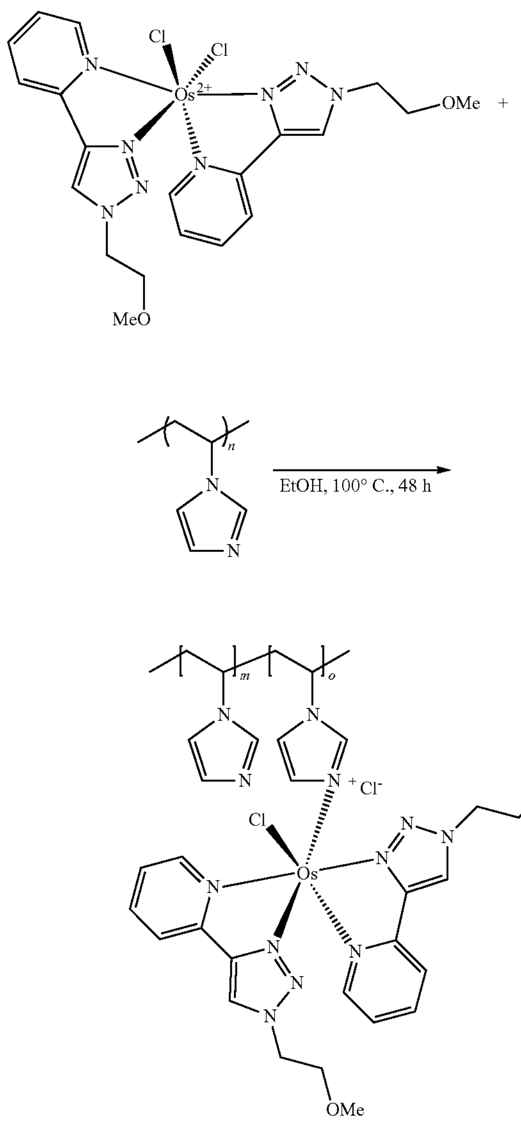

m:o = 4:1

A reflux condenser, a gas inlet and a thermometer were equipped to a 100 mL three-neck round bottom flask, and Os(3-motz-py)$_2$Cl$_2$ [Chemical formula 15] 0.15 g (0.22 mmol) prepared in Example 1.13. was added and completely dissolved in ethanol 10 mL in an argon gas atmosphere. Polyvinyl imidazole (Mn=10,000 g/mol) 0.1 g completely dissolved in ethanol 20 mL was added to this reaction mixture and heated to 100° C. and stirred for 2 days. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a brown oxidation-reduction polymer (PVI—Os(3-motz-py)$_2$Cl) of Chemical formula 35 of 0.12 g. (0.12 g, 48%)

Example 2.12. Synthesis of Oxidation-Reduction Polymer of Chemical Formula 39

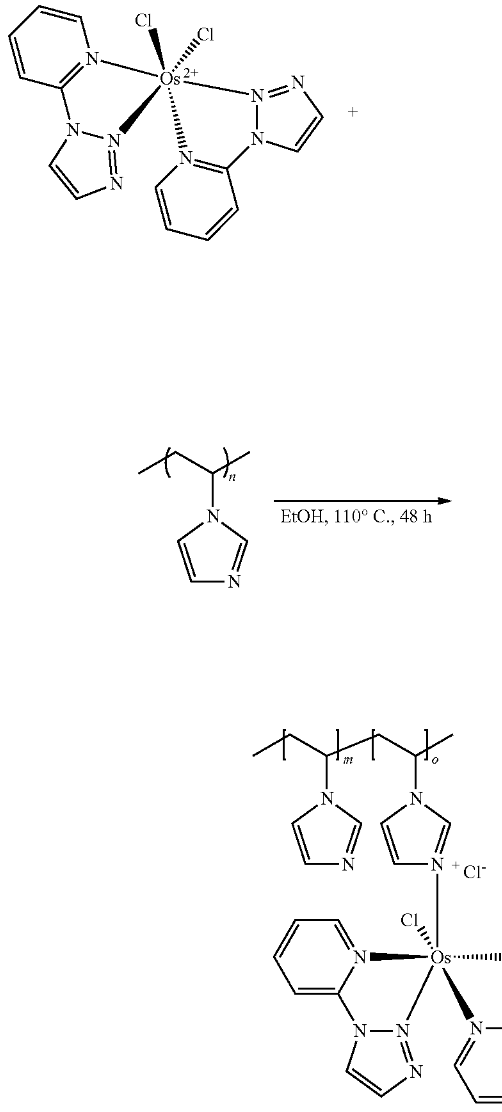

m:o = 4:1

A reflux condenser, a gas inlet and a thermometer were equipped to a 100 mL three-neck round bottom flask, and $Os(1,2,3\text{-tz-py})_2Cl_2$ [Chemical formula 18] 0.12 g (0.22 mmol) prepared in Example 1.16. was added and completely dissolved in ethanol 10 mL in an argon gas atmosphere. Polyvinyl imidazole (Mn=10,000 g/mol) 0.1 g completely dissolved in ethanol 20 mL was added to this reaction mixture and heated to 110° C. and stirred for 2 days. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a red oxidation-reduction polymer (PVI—$Os(1,2,3\text{-tz-py})_2Cl$) of Chemical formula 36 of 0.22 g. (0.21 g, 96%)

Example 2.13. Synthesis of Oxidation-Reduction Polymer of Chemical Formula 40

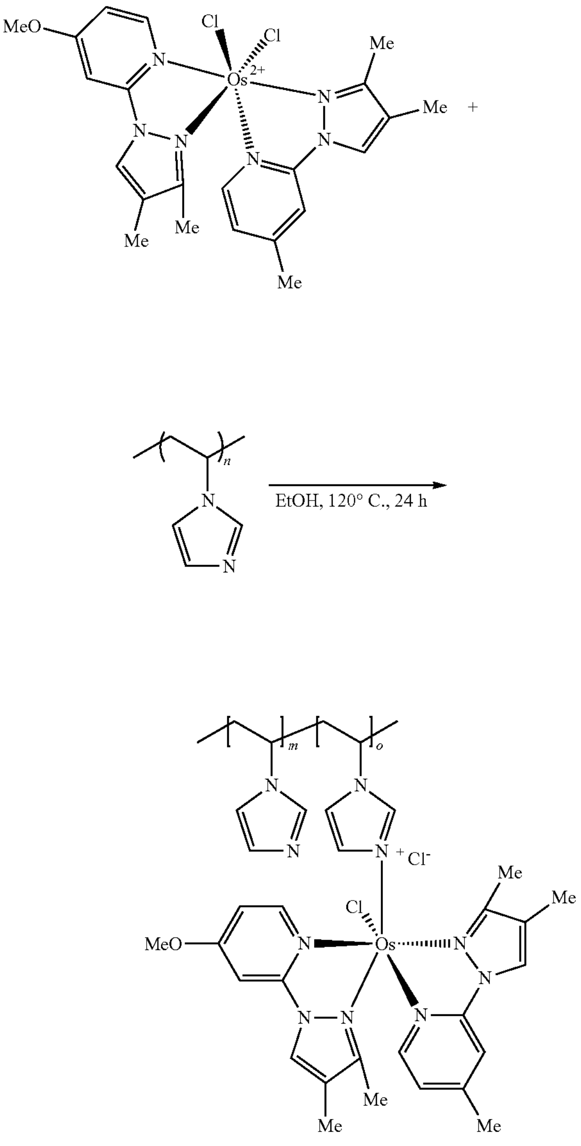

m:o = 3:1

$Os(3,4\text{-DiMe-pz-4-Me-py})_2Cl_2$ [Chemical formula 20] 0.17 g (0.27 mmol) prepared in Example 1.18. was added in a 100 mL shrink flask and completely dissolved in ethanol 15 mL in an argon gas atmosphere. Polyvinyl imidazole (Mn=10,000 g/mol) 0.1 g completely dissolved in ethanol 20 mL was added to this reaction mixture and heated to 120° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—$Os(3,4\text{-DiMe-pz-4-Me-py})_2Cl$) of Chemical formula 37 of 0.22 g. (0.22 g, 81%)

Example 2.14. Synthesis of Oxidation-Reduction Polymer of Chemical Formula 41

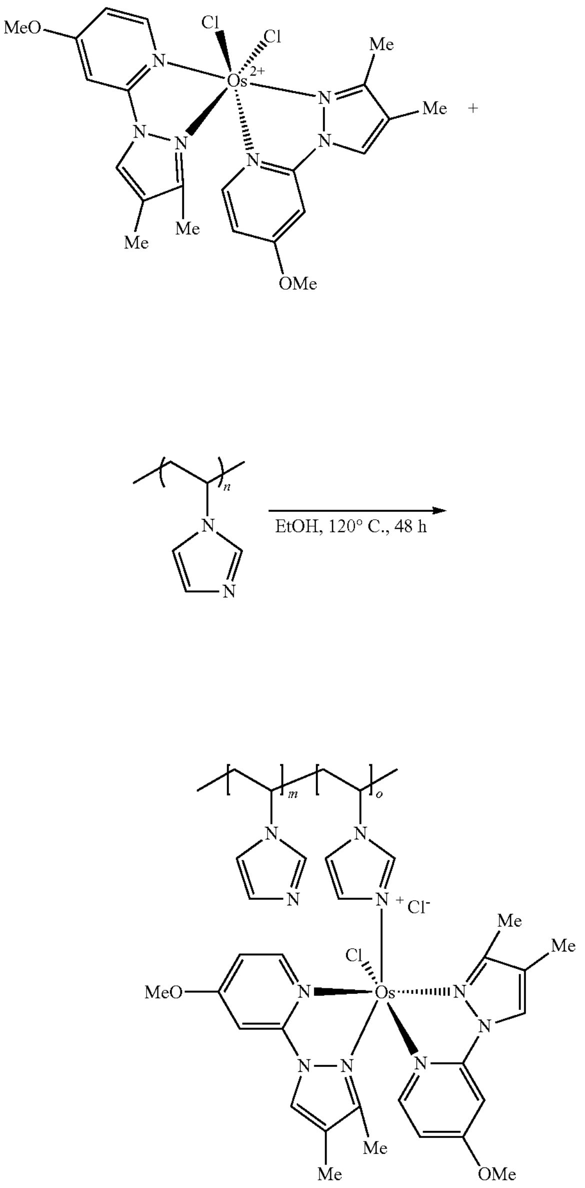

m:o = 4:1

Os(3,4-Dime-pz-4-MeO-py)$_2$Cl$_2$ [Chemical formula 21] 0.29 g (0.43 mmol) prepared in Example 1.19. was added in a 100 mL shrink flask and completely dissolved in ethanol 20 mL in an argon gas atmosphere. Polyvinyl imidazole (Mn=10,000 g/mol) 0.2 g completely dissolved in ethanol 30 mL was added to this reaction mixture and heated to 120° C. and stirred for 48 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a brown oxidation-reduction polymer (PVI—Os(3,4-Dime-pz-4-MeO-py)$_2$Cl) of Chemical formula 38 of 0.40 g. (0.40 g, 81%)

Example 2.15. Synthesis of Oxidation-Reduction Polymer of Chemical Formula 42

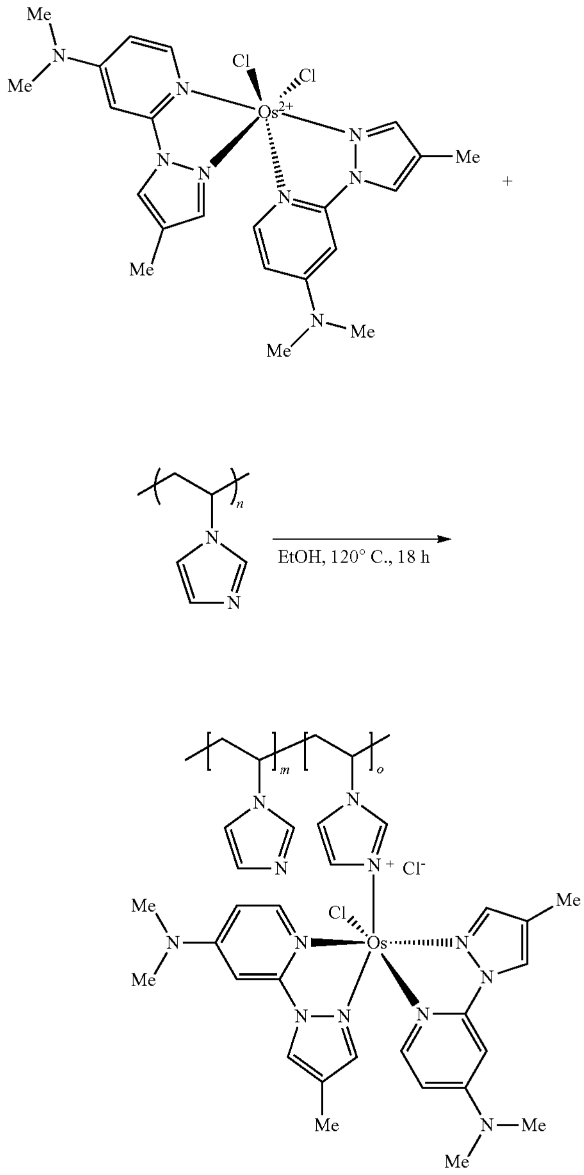

m:o = 3:1

Os(4-Me-pz-4-DiAM-py)$_2$Cl$_2$ [Chemical formula 22] 0.18 g (0.27 mmol) prepared in Example 1.20. was added in a 100 mL shrink flask and completely dissolved in ethanol 20 mL in an argon gas atmosphere. Polyvinyl imidazole (Mn=10,000 g/mol) 0.1 g completely dissolved in ethanol 20 mL was added to this reaction mixture and heated to 120° C. and stirred for 18 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a brown oxidation-reduction polymer (PVI—Os(4-Me-pz-4-DiAM-py)$_2$Cl) of Chemical formula 39 of 0.24 g. (0.24 g, 86%)

Example 2.16. Synthesis of Oxidation-Reduction Polymer of Chemical Formula

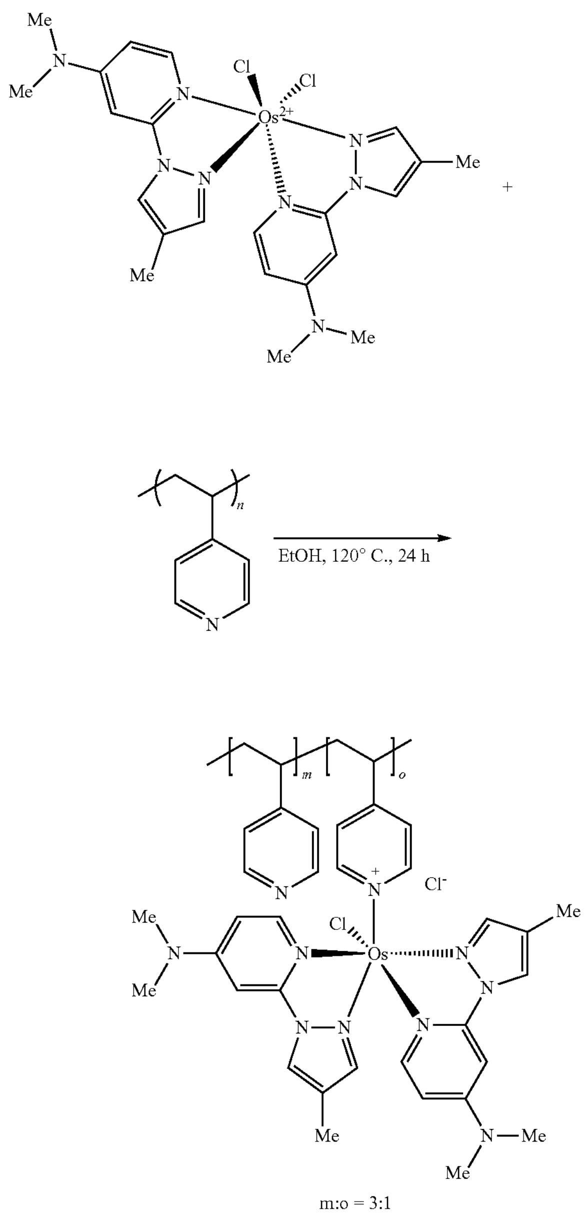

$Os(4\text{-}Me\text{-}pz\text{-}4\text{-}DiAM\text{-}py)_2Cl_2$ [Chemical formula 22] 0.5 g (0.76 mmol) prepared in Example 1.20. was added in a 250 mL shrink flask and completely dissolved in ethanol 60 mL in an argon gas atmosphere. Polyvinyl pyridine (Mn=160, 000 g/mol) 0.32 g completely dissolved in ethanol 30 mL was added to this reaction mixture and heated to 120° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a brown oxidation-reduction polymer (PVP—$Os(4\text{-}Me\text{-}pz\text{-}4\text{-}DiAM\text{-}py)_2Cl$) of Chemical formula 40 of 0.70 g. (0.70 g, 85%)

Example 2.17. Synthesis of Oxidation-Reduction Polymer of Chemical Formula 44

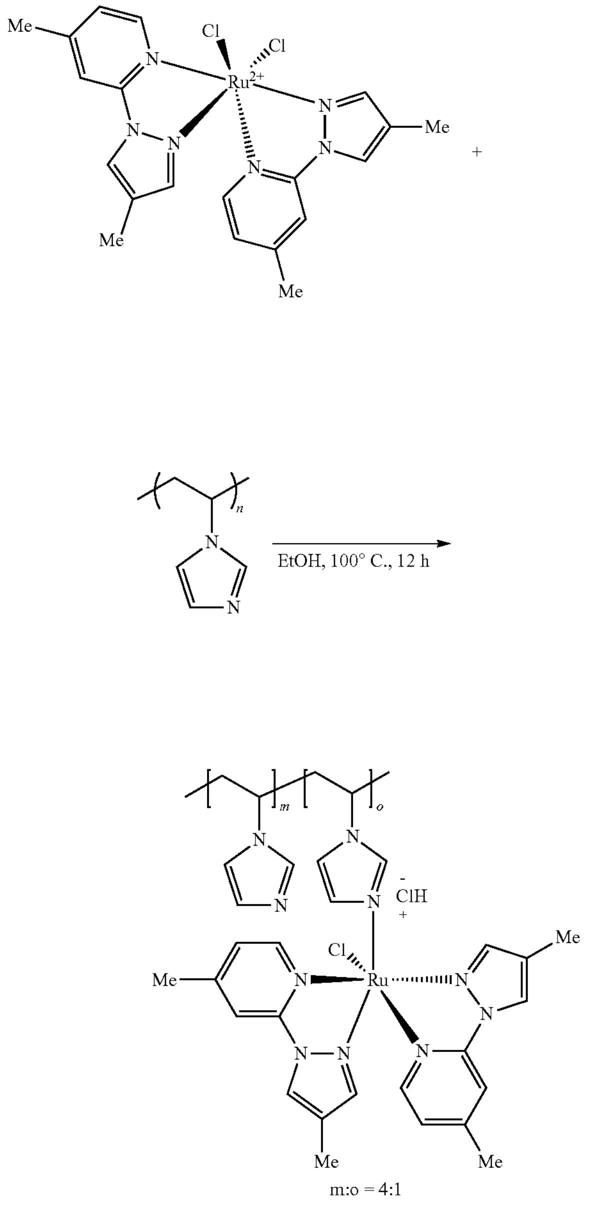

$Ru(4\text{-}Me\text{-}pz4\text{-}Me\text{-}py)_2Cl_2$ [Chemical formula 24] 0.14 g (0.27 mmol) prepared in Example 1.22. was added in a 100 mL shrink flask and completely dissolved in ethanol 30 mL in an argon gas atmosphere. Polyvinyl imidazole (Mn=10, 000 g/mol) 0.1 g completely dissolved in ethanol 20 mL was added to this reaction mixture and heated to 100° C. and stirred for 12 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a dark green oxidation-reduction polymer (PVI—$Ru(4\text{-}Me\text{-}pz4\text{-}Me\text{-}py)_2Cl$) of Chemical formula 44 of 0.24 g. (0.2 g, 83%)

Example 2.18. Synthesis of Oxidation-Reduction Polymer of Chemical Formula 45

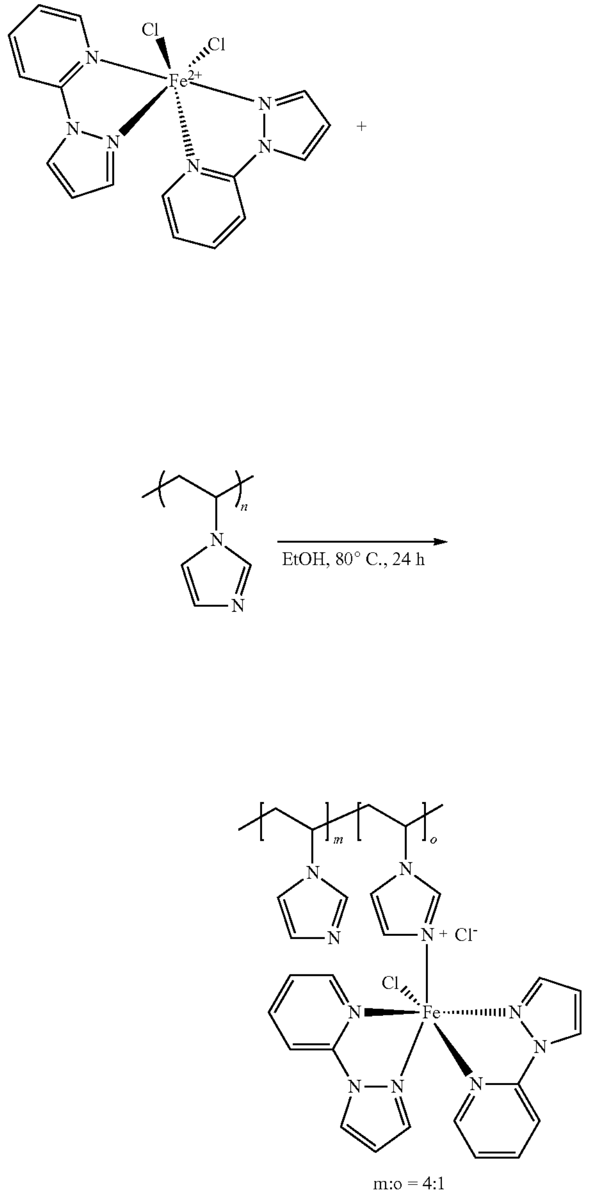

$Fe(pzpy)_2Cl_2$ [Chemical formula 25] 0.11 g (0.27 mmol) prepared in Example 1.23. was added in a 100 mL shrink flask and completely dissolved in ethanol 25 mL in an argon gas atmosphere. Polyvinyl imidazole (Mn=10,000 g/mol) 0.1 g completely dissolved in ethanol 20 mL was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times, and then dried in a vacuum oven of 40° C. for 24 hours to finally obtain a red-brown oxidation-reduction polymer (PVI—$Fe(pzpy)_2Cl$) of Chemical formula 45 of 0.1 g. (0.1 g, 47%)

Example 3. Synthesis of Oxidation-Reduction Polymer Comprising the Transition Metal Complex According to the Present Invention and a Crosslinkable Functional Group

Example 3.1. Synthesis of Oxidation-Reduction Polymer of Chemical Formula 48

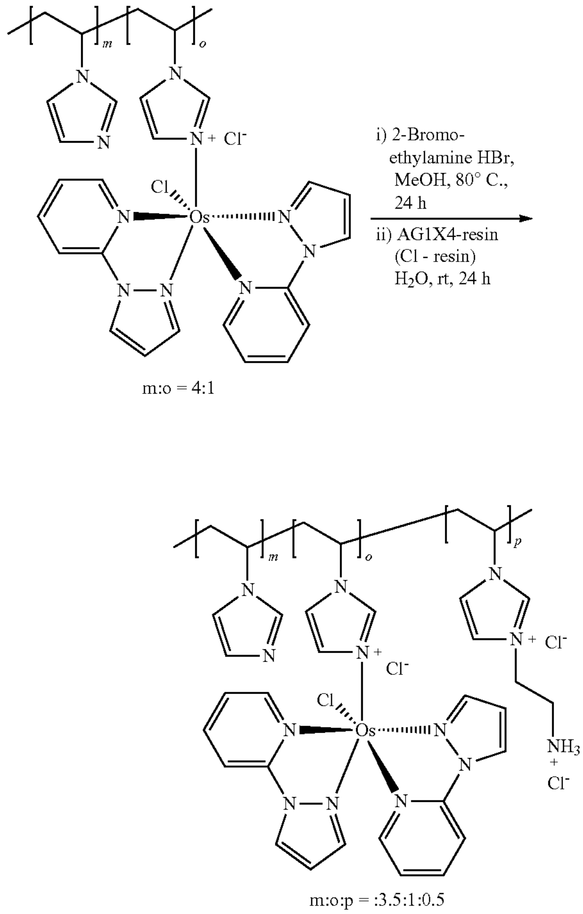

A reflux condenser, a gas inlet and a thermometer were equipped to a 100 mL three-neck round bottom flask, and the [Chemical formula 28] polymer prepared in Example 2.1. of 0.2 g was added and completely dissolved in methanol in an argon gas atmosphere. 2-bromoethylamine 20 mg (0.1 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1x4) 20 mL was added and stirred for 24 hours. This reaction mixture was filtered under reduced pressure to remove the resin and the filtered aqueous solution was lyophilized to remove water, thereby finally obtaining a green [Chemical formula 48] polymer of 0.2 g. (0.2 g. 90%)

Example 3.2. Synthesis of Oxidation-Reduction Polymer of Chemical Formula 49

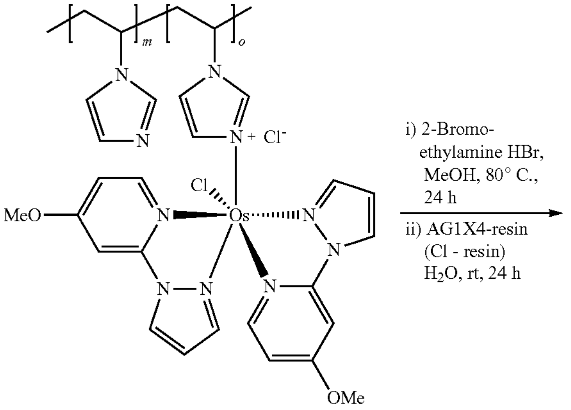

m:o = 4:1

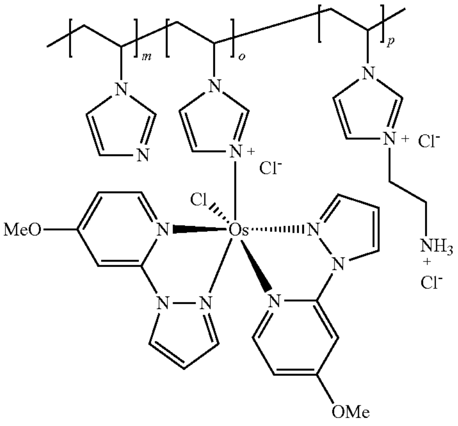

m:o:p = :3.5:1:0.5

A reflux condenser, a gas inlet and a thermometer were equipped to a 100 mL three-neck round bottom flask, and the [Chemical formula 30] polymer prepared in Example 2.3. of 0.2 g was added and completely dissolved in methanol in an argon gas atmosphere. 2-bromoethylamine 20 mg (0.1 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1×4) 20 mL was added and stirred for 24 hours. This reaction mixture was filtered under reduced pressure to remove the resin and the filtered aqueous solution was lyophilized to remove water, thereby finally obtaining a green [Chemical formula 49] polymer of 0.2 g. (0.2 g. 90%)

Example 3.3. Synthesis of Oxidation-Reduction Polymer of Chemical Formula 50

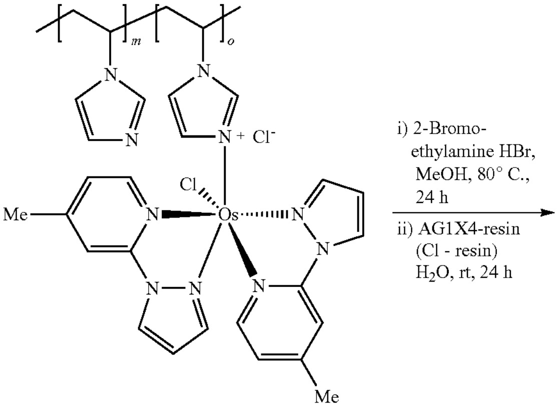

m:o = 3:1

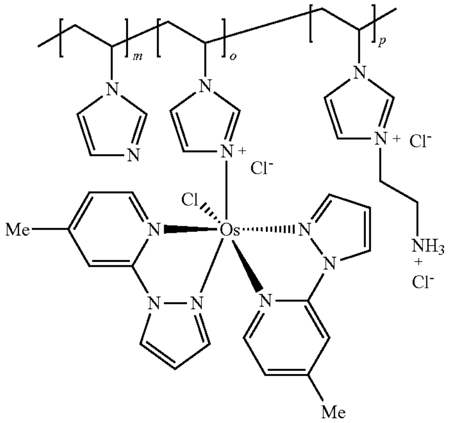

m:o:p = :2.5:1:0.5

A reflux condenser, a gas inlet and a thermometer were equipped to a 100 mL three-neck round bottom flask, and the [Chemical formula 31] polymer prepared in Example 2.4. of 0.4 g was added and completely dissolved in methanol in an argon gas atmosphere. 2-bromoethylamine 50 mg (0.25 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1×4) 20 mL was added and stirred for 24 hours. This reaction mixture was filtered under reduced pressure to remove the resin and the filtered aqueous solution was lyophilized to remove water, thereby finally obtaining a green [Chemical formula 50] polymer of 0.41 g. (0.41 g. 91%)

Example 3.4. Synthesis of Oxidation-Reduction Polymer of Chemical Formula 51

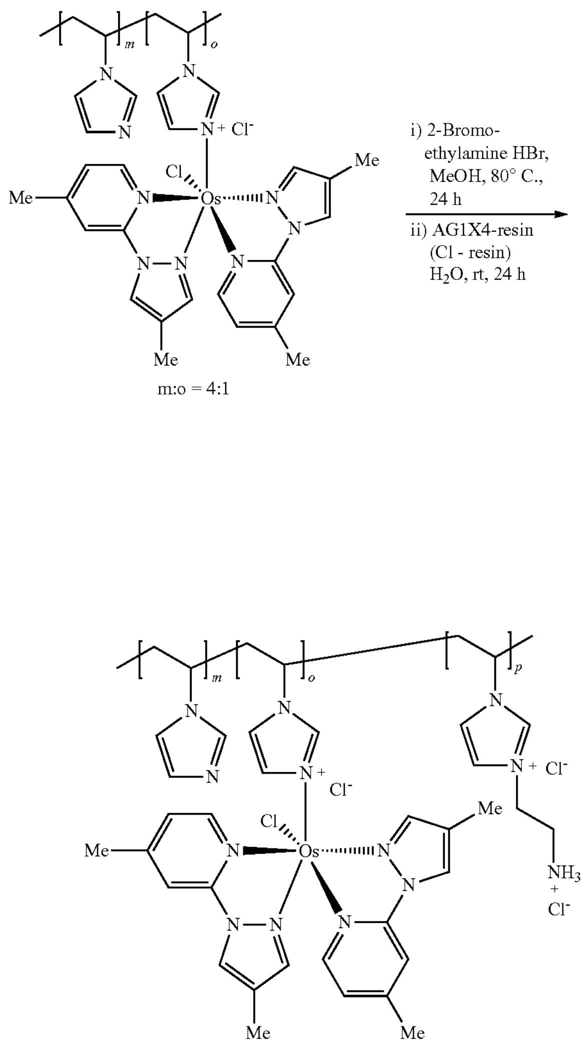

m:o = 4:1 m:o:p = :3.5:1:0.5

A reflux condenser, a gas inlet and a thermometer were equipped to a 100 mL three-neck round bottom flask, and the [Chemical formula 34] polymer prepared in Example 2.7. of 0.4 g was added and completely dissolved in methanol in an argon gas atmosphere. 2-bromoethylamine 50 mg (0.25 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1×4) 20 mL was added and stirred for 24 hours. This reaction mixture was filtered under reduced pressure to remove the resin and the filtered aqueous solution was lyophilized to remove water, thereby finally obtaining a green [Chemical formula 51] polymer of 0.4 g. (0.4 g. 90%)

Example 3.5. Synthesis of Oxidation-Reduction Polymer of Chemical Formula 52

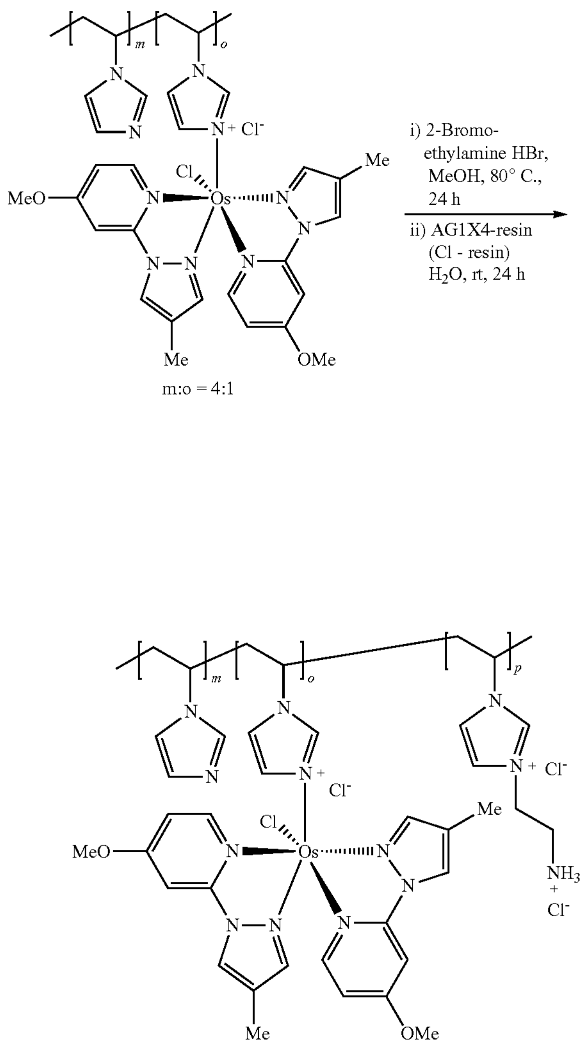

m:o = 4:1 m:o:p = :3.5:1:0.5

A reflux condenser, a gas inlet and a thermometer were equipped to a 100 mL three-neck round bottom flask, and the [Chemical formula 35] polymer prepared in Example 2.8. of 0.2 g was added and completely dissolved in methanol in an argon gas atmosphere. 2-bromoethylamine 20 mg (0.1 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1×4) 20 mL was added and stirred for 24 hours. This reaction mixture was filtered under reduced pressure to remove the resin and the filtered aqueous solution was lyophilized to remove water, thereby finally obtaining a green [Chemical formula 52] polymer of 0.2 g. (0.2 g. 90%)

Example 3.6. Synthesis of Oxidation-Reduction Polymer of Chemical Formula 53

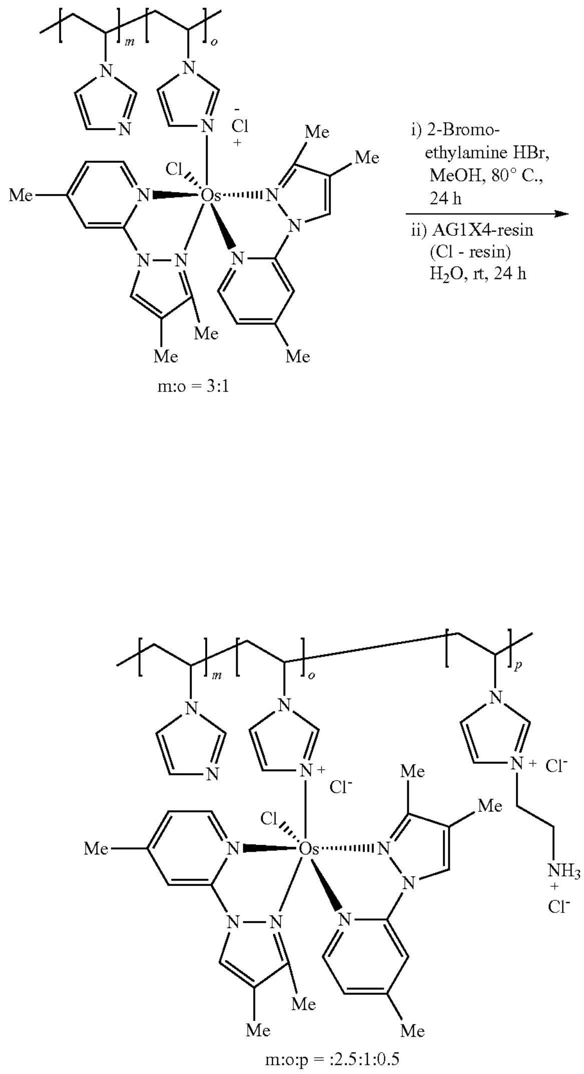

A reflux condenser, a gas inlet and a thermometer were equipped to a 100 mL three-neck round bottom flask, and the [Chemical formula 40] polymer prepared in Example 2.13. of 0.2 g was added and completely dissolved in methanol in an argon gas atmosphere. 2-bromoethylamine 20 mg (0.1 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1x4) 20 mL was added and stirred for 24 hours. This reaction mixture was filtered under reduced pressure to remove the resin and the filtered aqueous solution was lyophilized to remove water, thereby finally obtaining a green [Chemical formula 53] polymer of 0.2 g. (0.2 g. 90%)

Example 3.7. Synthesis of Oxidation-Reduction Polymer of Chemical Formula 54

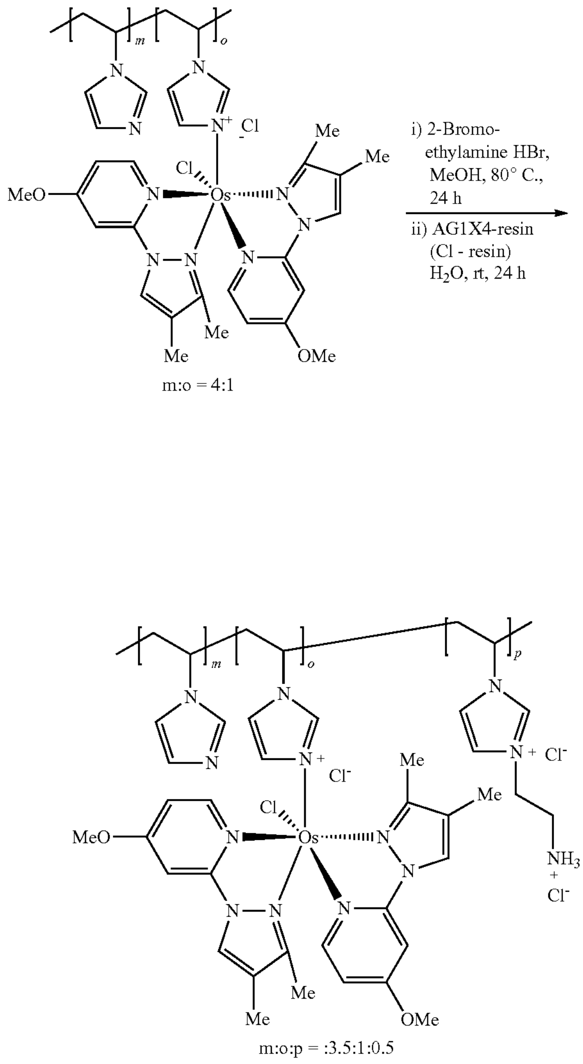

A reflux condenser, a gas inlet and a thermometer were equipped to a 100 mL three-neck round bottom flask, and the [Chemical formula 41] polymer prepared in Example 2.14. of 0.2 g was added and completely dissolved in methanol in an argon gas atmosphere. 2-bromoethylamine 20 mg (0.1 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1x4) 20 mL was added and stirred for 24 hours. This reaction mixture was filtered under reduced pressure to remove the resin and the filtered aqueous solution was lyophilized to remove water, thereby finally obtaining a green [Chemical formula 54] polymer of 0.2 g. (0.2 g. 90%)

Example 3.8. Synthesis of Oxidation-Reduction Polymer of Chemical Formula 57

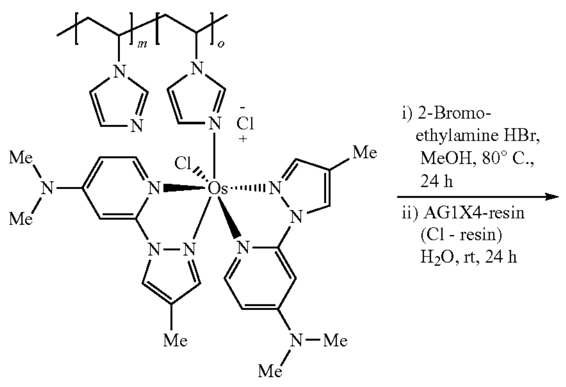

m:o = 3:1

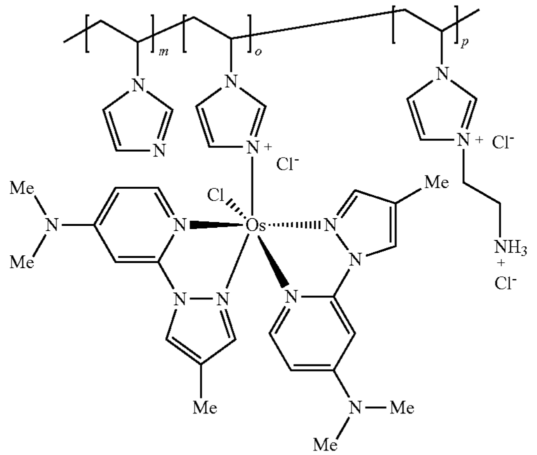

m:o:p = :2.5:1:0.5

A reflux condenser, a gas inlet and a thermometer were equipped to a 100 mL three-neck round bottom flask, and the [Chemical formula 42] polymer prepared in Example 2.15. of 0.2 g was added and completely dissolved in methanol in an argon gas atmosphere. 2-bromoethylamine 20 mg (0.1 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1×4) 20 mL was added and stirred for 24 hours. This reaction mixture was filtered under reduced pressure to remove the resin and the filtered aqueous solution was lyophilized to remove water, thereby finally obtaining a red [Chemical formula 57] polymer of 0.2 g. (0.2 g. 90%)

Example 3.9. Synthesis of Oxidation-Reduction Polymer of Chemical Formula 58

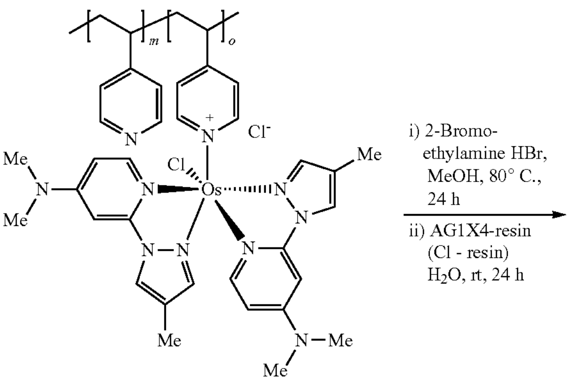

m:o = 3:1

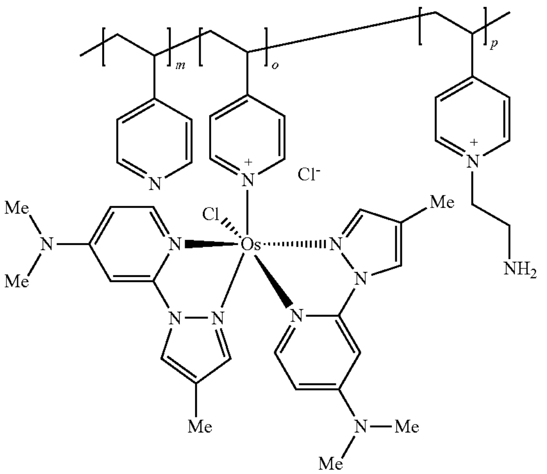

m:o:p = :2.5:1:0.5

A reflux condenser, a gas inlet and a thermometer were equipped to a 100 mL three-neck round bottom flask, and the [Chemical formula 43] polymer prepared in Example 2.16. of 0.4 g was added and completely dissolved in methanol in an argon gas atmosphere. 2-bromoethylamine 30 mg (0.15 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1×4) 20 mL was added and stirred for 24 hours. This reaction mixture was filtered under reduced pressure to remove the resin and the filtered aqueous solution was lyophilized to remove water, thereby finally obtaining a red [Chemical formula 58] polymer of 0.41 g. (0.41 g. 95%)

Example 3.10. Synthesis of Oxidation-Reduction Polymer of Chemical Formula 59

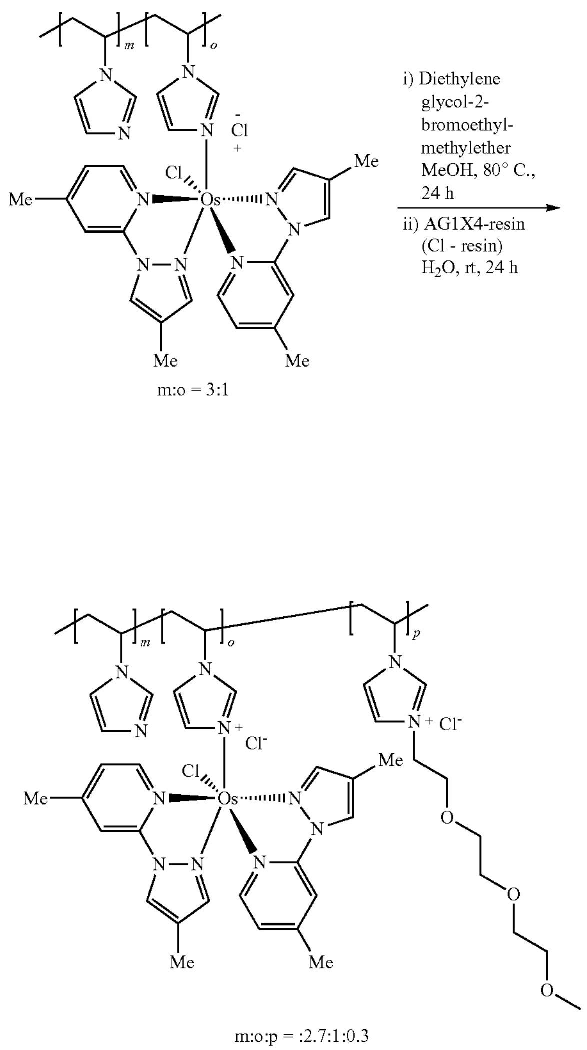

A reflux condenser, a gas inlet and a thermometer were equipped to a 100 mL three-neck round bottom flask, and the [Chemical formula 34] polymer prepared in Example 2.7. of 0.4 g was added and completely dissolved in methanol in an argon gas atmosphere. Diethylene glycol-2-bromoethylmethylether 24 mg (0.1 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1x4) 20 mL was added and stirred for 24 hours. This reaction mixture was filtered under reduced pressure to remove the resin and the filtered aqueous solution was lyophilized to remove water, thereby finally obtaining a green [Chemical formula 59] polymer of 0.4 g. (0.4 g. 94%)

Example 3.11. Synthesis of Oxidation-Reduction Polymer of Chemical Formula 60

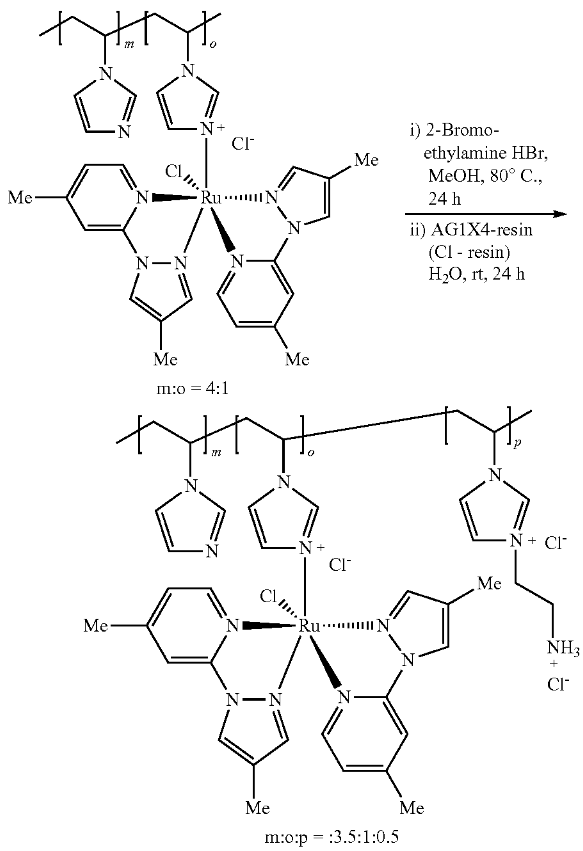

A reflux condenser, a gas inlet and a thermometer were equipped to a 100 mL three-neck round bottom flask, and the [Chemical formula 44] polymer prepared in Example 2.17. of 0.4 g was added and completely dissolved in methanol in an argon gas atmosphere. 2-bromoethylamine 30 mg (0.15 mmol) was added to this reaction mixture and heated to 80° C. and stirred for 24 hours. After completing the reaction, the reaction mixture was cooled to a room temperature and dropped in diethyl ether to obtain polymer precipitates. The produced solids were filtered under reduced pressure and washed with diethyl ether several times. In order to exchange a Br ion comprised in the reactant to a Cl ion, the solids filtered in a 200 mL beaker and water 50 mL were added and dissolved all, and then an ion exchange resin (AG1x4) 20 mL was added and stirred for 24 hours. This reaction mixture was filtered under reduced pressure to remove the resin and the filtered aqueous solution was lyophilized to remove water, thereby finally obtaining a red [Chemical formula 60] polymer of 0.35 g. (0.35 g. 81%)

Experimental Example 1: Confirmation of Electrochemical Characteristics of the Transition Metal Complexes and Oxidation-Reduction Polymers According to the Present Invention Using Cyclic Voltammetry In order to confirm the performance as an electron transfer mediator of the transition metal complex having a bidentate ligand comprising pyrazole, triazole, tetrazole, oxadiazole or thiadiazole or the like and oxidation-reduction polymer comprising the same according to the present invention, electrochemical characteristics was measured using cyclic voltammetry according to the following experimental method.

Experimental Method 1. 20 mg of each compound (transition metal complex) of Chemical formulas 3, 4, 9, 11, 14, 15, 16, 17, 18, 20, 22, 23, 24, and 25 according to the present invention was dissolved in 0.1 M tetrabutylammonium perchlorate dimethyl sulfoxide solution of 2 mL.

20 mg of each compound of Chemical formulas 28, 34, 40, and 42 (oxidation-reduction polymer) and compound of Chemical formulas 48, 51, 57, and 59 (oxidation-reduction polymer comprising a crosslinkable functional group) according to the present invention was dissolved in deionized water and 0.1 M sodium chloride solution of 5 mL. As a comparison group, 20 mg of the compound of the following Chemical formula 61 was dissolved in deionized water and 0.1 M sodium chloride solution of 5 mL.

[Chemical formula 61]

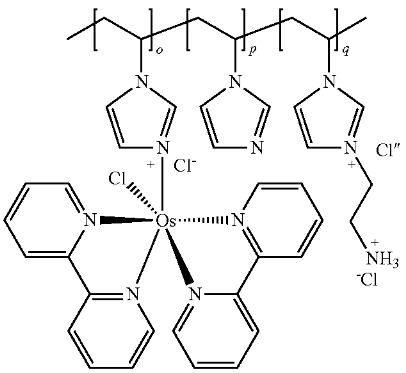

2. In order to remove oxygen in the solution, degassing was performed with argon for 5~10 minutes.
3. A working electrode, a reference electrode, and a counter electrode were connected to the solution in which oxygen was degassed, and a change in electrical signals according to a change in voltage was measured in an argon gas atmosphere.
4. This experimental result was shown in Table 1 to Table 3, and FIG. 1*a* to FIG. 10*o*, FIG. 2 and FIG. 3 below.

The experimental results of each compound was shown corresponding to the drawings below:

Chemical formula 3 (FIG. 1*a*), Chemical formula 4 (FIG. 1*b*), Chemical formula 9 (FIG. 1*c*), Chemical formula 11 (FIG. 1*d*), Chemical formula 14 (FIG. 1*e*), Chemical formula 15 (FIG. 1*f*), Chemical formula 16 (FIG. 1*g*), Chemical formula 17 (FIG. 1*h*), Chemical formula 18 (FIG. 1*i*), Chemical formula 20 (FIG. 1*j*), Chemical formula 22 (FIG. 1*k*), Chemical formula 23 (FIG. 1*l*), Chemical formula 24 (FIG. 1*m*), Chemical formula 25 (FIG. 1*n*), Chemical formula 3, 4, 11, 14, 15, 16 (FIG. 10*o*), Chemical formula 3 (comparison group), 28, 34, 40, 42 (FIG. 2), Chemical formula 28 (comparison group), 48, 51, 57, 59, 61 (comparison group) (FIG. 3).

Experimental Materials/Conditions

Working electrode: Free carbon electrode (dia: 3.0 mm)

Reference electrode: Ag/AgCl electrode

Counter electrode: Platinum rod

Test Parameters

Equipment: EmStat(PalmSens Co.)

Technique: cyclic voltammetry

Potential range: −1.0~1.0V

Scan rate: 10 mV/s

TABLE 1

| Transition metal complex | $E_{pc}$ (V) | $E_{pa}$ (V) |
|---|---|---|
| [Chemical formula3] | 0.03 | −0.12 |
| [Chemical formula4] | 0.05 | −0.12 |
| [Chemical formula 9] | −0.08 | −0.18 |
| [Chemical formula 11] | −0.16 | −0.27 |
| [Chemical formula 14] | −0.18 | −0.26 |
| [Chemical formula 15] | 0.04 | −0.16 |
| [Chemical formula 16] | 0.26 | 0.10 |
| [Chemical formula 17] | −0.42 | −0.56 |
| [Chemical formula 18] | −0.40 | −0.49 |
| [Chemical formula 20] | −0.1 | −0.24 |
| [Chemical formula 22] | −0.32 | −0.47 |
| [Chemical formula 23] | 0.50 | 0.60 |
| [Chemical formula 24] | 0.49 | 0.36 |
| [Chemical formula 25] | 0.71 | 0.63 |

TABLE 2

| Oxidation-reduction complex | $E_{pc}$ (V) | $E_{pa}$ (V) |
|---|---|---|
| [Chemical formula3] | 0.03 | −0.12 |
| [Chemical formula 28] | 0.33 | 0.17 |
| [Chemical formula 34] | 0.24 | 0.14 |
| [Chemical formula 40] | 0.26 | 0.12 |
| [Chemical formula 42] | 0.12 | −0.03 |

TABLE 3

| Oxidation-reduction complex comprising a crosslinkable functional group | $E_{pc}$ (V) | $E_{pa}$ (V) |
|---|---|---|
| [Chemical formula 48] | 0.33 | 0.17 |
| [Chemical formula 51] | 0.26 | 0.14 |
| [Chemical formula 57] | 0.15 | 0.05 |
| [Chemical formula 59] | 0.26 | 0.13 |
| [Chemical formula 61] | 0.39 | 0.29 |

As shown in Table 1 and FIG. 1*a* to FIG. 1*o* above, it was confirmed that the transition metal complex according to the present invention had various potential values depending on the ligand type.

As shown in Table 2 and FIG. 2 above, it was confirmed that the intrinsic potential value of the complex was changed when the transition metal complex according to the present invention was synthesized to an oxidation-reduction polymer.

In addition, as shown in Table 3 and FIG. 3 above, it was confirmed that it did not affect the potential value of the oxidation-reduction polymer, when a crosslinkable functional group was introduced to the oxidation-reduction polymer according to the present invention. Furthermore, it was confirmed that the compounds of Chemical formulas 48, 51, 57, and 59 showed lower potential values compared to the compound of Chemical formula 61, which is a conventionally known control group, so they could act as an oxidation-reduction mediator with high efficiency.

Experimental Example 2: Preparation of Electrochemical Sensor for Continuous Blood Glucose Measurement Comprising the Oxidation-Reduction Polymer According to the Present Invention In order to produce an electrochemical sensor (electrochemical biosensor) comprising an electron transfer mediator of the oxidation-reduction polymer according to the present invention, a sensor was produced by the following method.

Experimental Method

1. The compounds of Chemical formulas 48, 51, 53, and 59 according to the present invention and the compound of Number 61 as a comparison group were dissolved in an aqueous solution with oxidoreductase (glucose dehydrogenase), a carbon nanotube (CNT), a non-ionic surfactant (Triton-X) and a crosslinking material (polyethylene glycol diglycidylether), respectively, and each solution was prepared using stirring and ultrasonic dispersion methods.
2. In order to manufacture a continuous blood glucose electrochemical sensor, each solution prepared was aliquoted on an electrode printed with carbon paste and coated, and then cured through a crosslinking reaction at a room temperature for 24 hours. After curing, the manufactured sensor was washed using distilled water.
3. As a method for comparing the electron transfer performance manufactured above with the electrode comprising Chemical formula 61, cyclic voltammetry was used.
4. This experimental result was shown in Table 4 and FIG. 4 below, respectively.

Experimental Materials/Conditions

Working electrode: Electrode manufactured above
Reference electrode: Ag/AgCl electrode
Counter electrode: Platinum wire
Electrolyte: Physiological saline solution containing phosphate buffer (Phosphate buffer with NaCl solution)
Test parameters
Equipment: EmStat(PalmSens Co.)
Technique: cyclic voltammetry
Potential range: −0.3~0.4V
Scan rate: 10 mV/s

TABLE 4

| Electrochemical sensor for continuous blood glucose measurement comprising oxidation-reduction polymer | $E^0$ (mV) | $E_c - E_a$ (mV) | $I_{pa}$ (μA) |
|---|---|---|---|
| [Chemical formula 48] | 133.3 | 110.7 | 40.1 |
| [Chemical formula 51] | 99.2 | 97.7 | 91.1 |
| [Chemical formula 53] | 100.7 | 83.3 | 71.0 |
| [Chemical formula 59] | 106.7 | 49 | 15.0 |
| [Chemical formula 61] | 216.2 | 147.6 | 129.6 |

As shown in Table 4 and FIG. 4 above, the potential (E°) of the electrode to which the oxidation-reduction polymer according to the present invention was applied had a lower potential than the comparison group electrode. This is the result similar to Experimental example 1, and in addition, through this experiment, it was confirmed that the working voltage of the electrochemical sensor for continuous blood glucose measurement could be stably used even at a lower voltage than the comparison group.

Experimental Example 3: Comparison of Sensitivity to Change in Glucose Concentration of Electrochemical Sensor for Continuous Blood Glucose Measurement 1. The electrodes manufactured in Experimental example 2 above using the compounds of Chemical formulas 51, 53 according to the present invention, and as a comparison group, No. 61 compound were compared by performing chronoamperometry in a 0~100 mM glucose solution.
2. The voltage applied when chronoamperometry was performed was 0.15 V for the electrode using the compound of 51, 53, and 0.25 V for the electrode using the compound of the comparison group No. 61.
3. The glucose concentration was 0.01, 0.05, 0.1, 0.5, 1, 5, 10, 50, or 100 mM, and a high concentration glucose solution was injected into physiological saline solution containing phosphate buffer at intervals of 200 seconds to reach each concentration. Each experiment was performed for 50 minutes.
4. This experimental result was shown in FIG. 5 and FIG. 6 below, respectively.

Experimental Materials/Conditions

Working electrode: Electrode manufactured above
Reference electrode: Ag/AgCl electrode
Counter electrode: Platinum wire
Electrolyte: Physiological saline solution containing phosphate buffer (Phosphate buffer with NaCl solution)
Test parameters
Equipment: EmStat(PalmSens Co.)
Technique: chronoamperometry
Potential range: 0.15 V, 0.25 V As shown in FIGS. 5 and 6, all the electrodes in which the oxidation-reduction polymer according to the present invention showed the linearity to glucose at a concentration of 10 mM or less, and showed similar sensitivity even though a lower voltage than the comparison group electrode was applied. In particular, based on that in the electrodes to which the compounds 51, 53 were applied, current at a concentration of 100 mM was larger than the comparison group, the maximum enzyme activity ($V_{max}$) seems to be about 1.2~2 times larger than the comparison group.

Experimental Example 4: Comparison of Glucose Sensitivity According to Voltage Increase of Electrochemical Sensor for Continuous Blood Glucose Measurement 1. The electrodes manufactured in Experimental example 2 above using the compounds of Chemical formulas 51, 53 according to the present invention, and as a comparison group, No. 61 compound were compared by performing multistep voltammetry (multi-potential step) in a glucose solution of 400 mM.
2. During performing the multistep voltammetry, by maintaining the voltage at a voltage from −0.2 V to 0.35 V at intervals of 0.05 V between them for 300 seconds, the current was observed.
3. This experimental result was shown in FIG. 7 below, respectively.

Experimental Materials/Conditions

Working electrode: Electrode manufactured above
Reference electrode: Ag/AgCl electrode
Counter electrode: Platinum wire
Electrolyte: Physiological saline solution containing phosphate buffer (Phosphate buffer with NaCl solution)
Test parameters
Equipment: EmStat(PalmSens Co.)
Technique: multi-potential step
Potential range: −0.2~0.35 V As shown in FIG. 7, it can be confirmed that all the electrodes in which the oxidation-reduction polymer according to the present invention is applied show sensitivity to glucose at a lower voltage than the comparison group electrode.

The invention claimed is:

1. A transition metal complex, which is a compound of the following Chemical formula 1, or a salt compound thereof:

[Chemical formula 1]

$$[M(L)_a(X_1)_b]^c d(X_2)$$

in the formula,

M is one kind transition metal selected from the group consisting of Fe, Ru, and Os, and L is a bidentate ligand comprising pyridine; and one structure selected from the group consisting of pyrazole, tetrazole, oxadiazole and thiadiazole, and the pyridine is pyridine unsubstituted, or substituted with 1 to 4 selected from the group consisting of $C_{1-4}$ alkyl group, $C_{1-4}$ alkoxy group, —(CH2)-O—$C_{1-4}$ alkyl group, —(CH2CH2)-O—$C_{1-4}$ alkyl group, and $C_{1-4}$ alkylamino group, and the one selected from the group consisting of pyrazole, tetrazole, and oxadiazole, is each independently unsubstituted, or substituted with 1 to 3 selected from the group consisting of $C_{1-4}$ alkyl group, $C_{1-4}$ alkoxy group, —(CH2)-O—$C_{1-4}$ alkyl group, —(CH2CH2)-O—$C_{1-4}$ alkyl group,

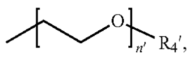

and $C_{1-4}$ alkylamino group, and

R'$_4$ is hydrogen or substituted or unsubstituted $C_{1-4}$ alkyl, and n' is an integer selected from 1 to 4, and a is 2 or 3, and in the substituted $C_{1-4}$ alkyl group, $C_{1-4}$ alkoxy group, —(CH2)-O—$C_{1-4}$ alkyl group, —(CH2CH2)-O—$C_{1-4}$ alkyl group or $C_{1-4}$ alkylamino group, a hydrogen atom is substituted with a halogen atom of F, Cl, Br or I, cyano group, hydroxy group, thiol group, nitro group, amino group, imino group, azido group, amidino group, hydrazine group, hydrazono group, oxo group, carbonyl group, carbamyl group, ester group, ether group, carboxyl group or salt thereof, sulfonic acid group or salt thereof, or phosphoric acid or salt thereof, and $X_1$ is one kind halogen atom selected from the group consisting of F, Cl, Br and I, and b is 0, 1, or 2, and c is an integer selected from 1 to 3, and $X_2$ is one kind counter ion selected from the group consisting of F, Cl, Br, I and $PF_6$, and d is 0, 1, 2, or 3.

2. The transition metal complex or salt compound thereof according to claim 1, wherein the transition metal complex is a compound of the following Chemical formula 2:

[Chemical formula 2]

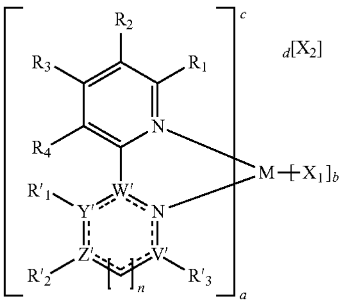

in the formula, $R_1$, $R_2$, $R_3$, and $R_4$ are each independently hydrogen, $C_{1-4}$ alkyl group, $C_{1-4}$ alkoxy group, (CH2)-O—$C_{1-4}$ alkyl group, (CH2CH2)-O—$C_{1-4}$ alkyl group, or $C_{1-4}$ alkylamino group, and n is 0, and at least one of W, Y', Z', and V' is nitrogen (N), and W' is nitrogen (N) or carbon (C), and Y', Z', and V' are each independently nitrogen (N), sulfur (S), oxygen (O), or carbon (C), and R'$_1$, R'$_2$, and R's are each independently hydrogen, $C_{1-4}$ alkyl group, $C_{1-4}$ alkoxy group, —(CH2)-O—$C_{1-4}$ alkyl group, —(CH2CH2)-O—$C_{1-4}$ alkyl group,

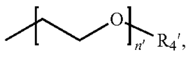

or $C_{1-4}$ alkylamino group, and or $C_{1-4}$ the $C_{1-4}$ alkyl group, $C_{1-4}$ alkoxy group, —(CH2)-O—$C_{1-4}$ alkyl group, —(CH2CH2)-O—$C_{1-4}$ alkyl group, $R_4$', n', or $C_{1-4}$ alkylamino group are the same as defined in claim 1, and M, a, $X_1$, b, c, $X_2$ and d are the same as defined in claim 1.

3. The transition metal complex or salt compound thereof according to claim 2, wherein the compound of Chemical formula 2 is a compound selected from the group consisting of compounds of the following Chemical formula 3 to 10, 12, 16, and 20-25:

[Chemical formula 3]

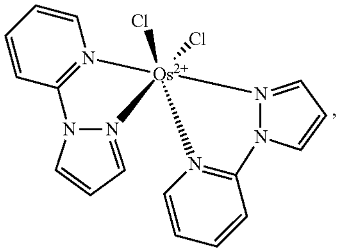

-continued
[Chemical formula 4]
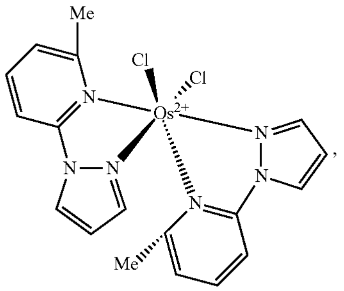
[Chemical formula 5]
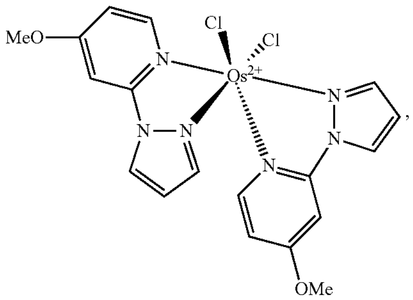
[Chemical formula 6]
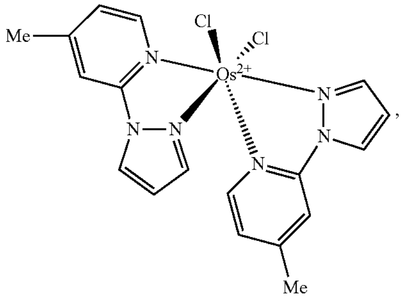
[Chemical formula 7]
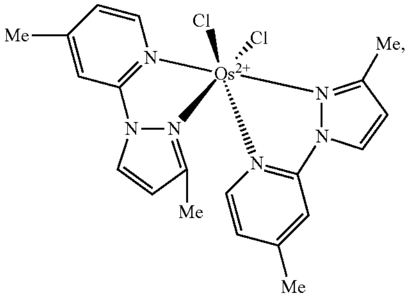
[Chemical formula 8]
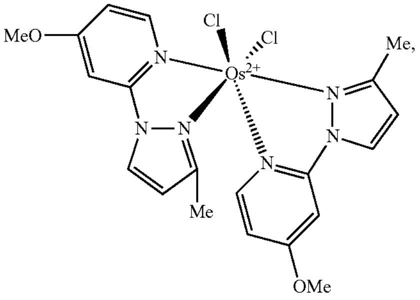
-continued
[Chemical formula 9]
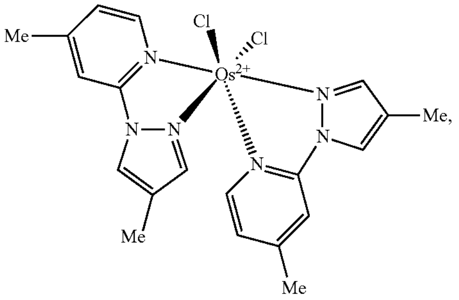
[Chemical formula 10]
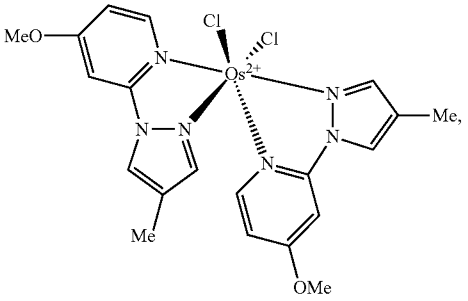
[Chemical formula 12]
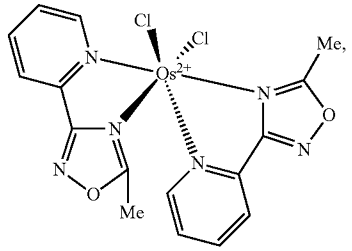
Chemical formula 16]
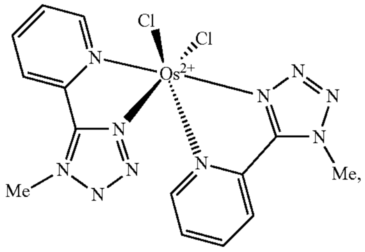
[Chemical formula 20]
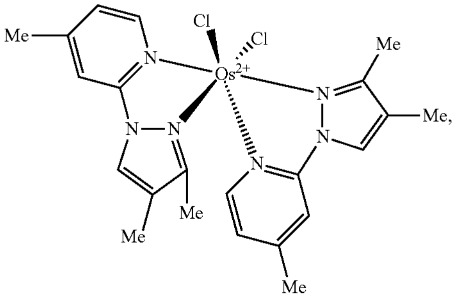

-continued

[Chemical formula 21]

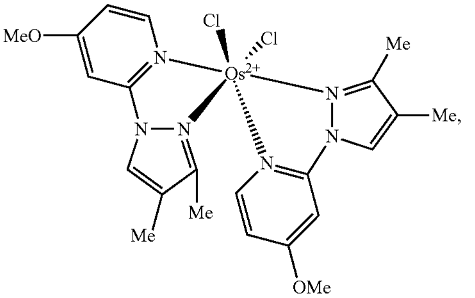

[Chemical formula 22]

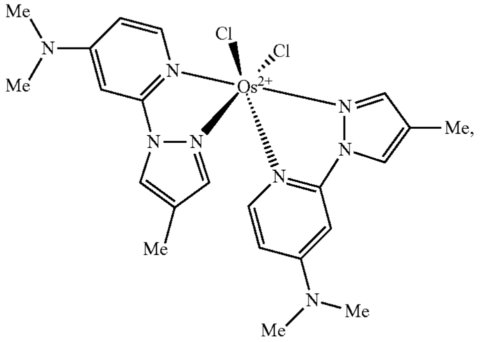

[Chemical formula 23]

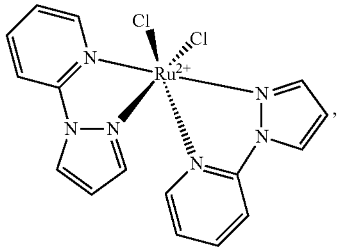

[Chemical formula 24]

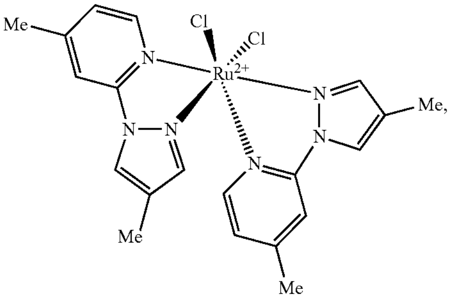

and

[Chemical formula 25]

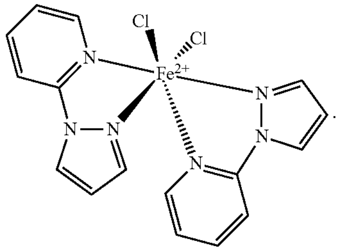

4. An oxidation-reduction polymer, represented by a compound of the following Chemical formula 26 or Chemical formula 27:

[Chemical formula 26]

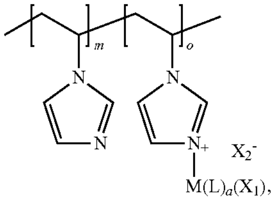

and

[Chemical formula 27]

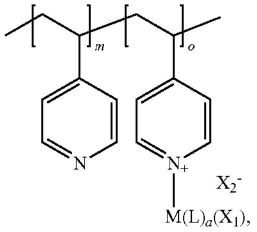

in the formula, m or o is each an integer selected from 10 to 600, and

M, L, a, $X_1$ and $X_2$ are each the same as defined in claim 1.

5. The oxidation-reduction polymer according to claim 4, wherein the compound of Chemical formula 26 or Chemical formula 27 is a compound selected from the group consisting of compounds of the following Chemical formulas 28 to 35, and 40 to 45:

[Chemical formula 28]

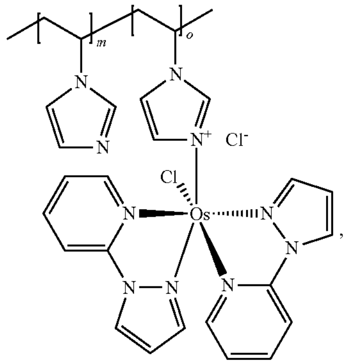

[Chemical formula 29]

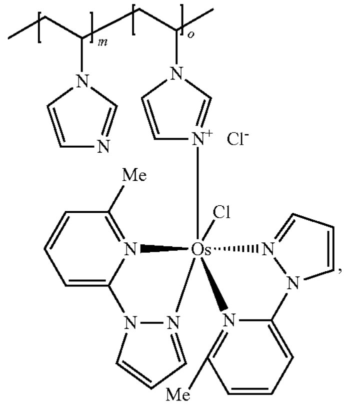

-continued
[Chemical formula 30]
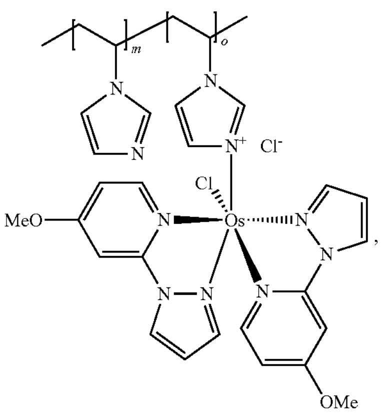
[Chemical formula 31]
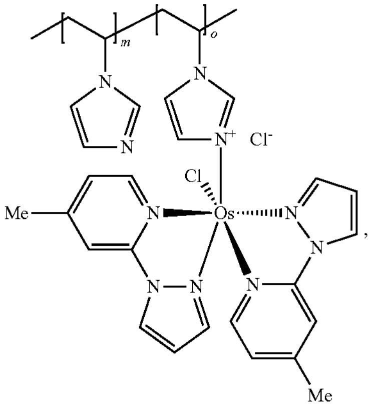
[Chemical formula 32]
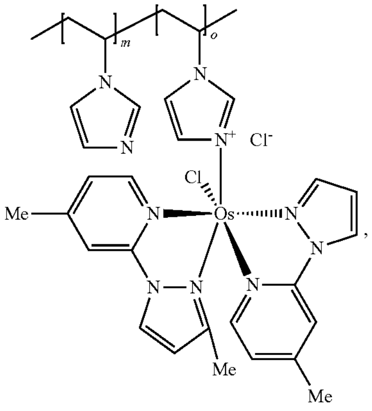
-continued
[Chemical formula 33]
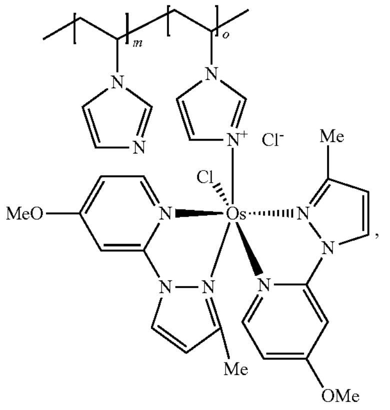
[Chemical formula 34]
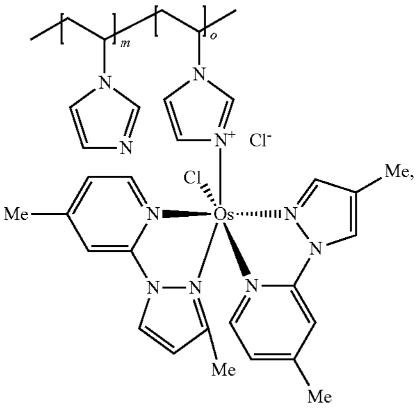
[Chemical formula 35]
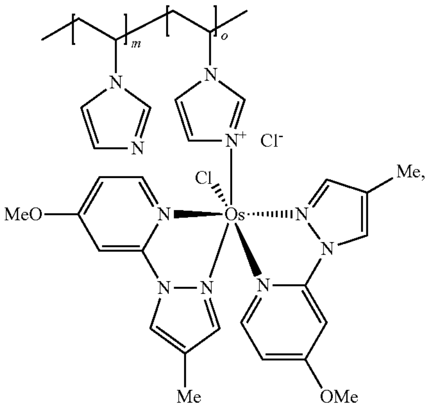
[Chemical formula 39]
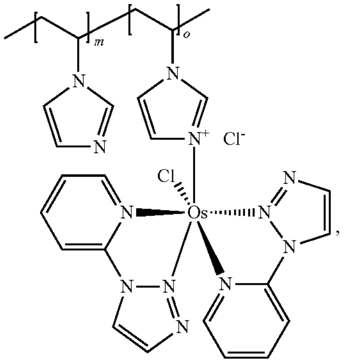

-continued

[Chemical formula 40]

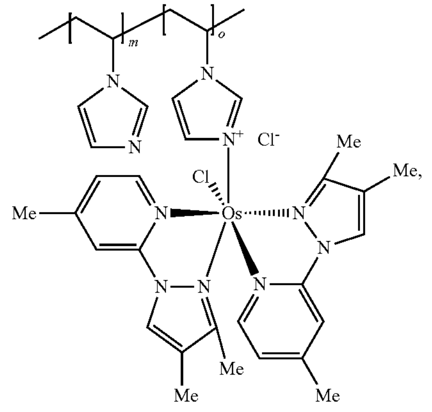

[Chemical formula 41]

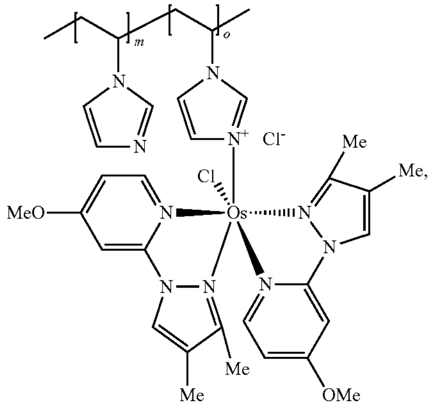

[Chemical formula 42]

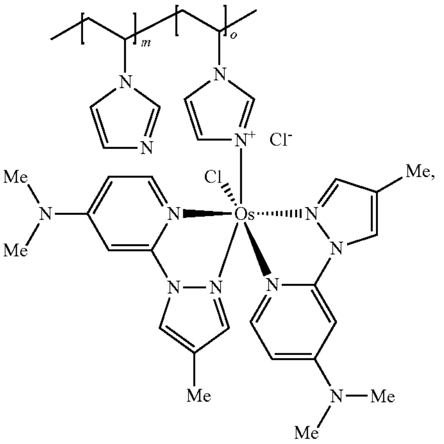

-continued

[Chemical formula 43]

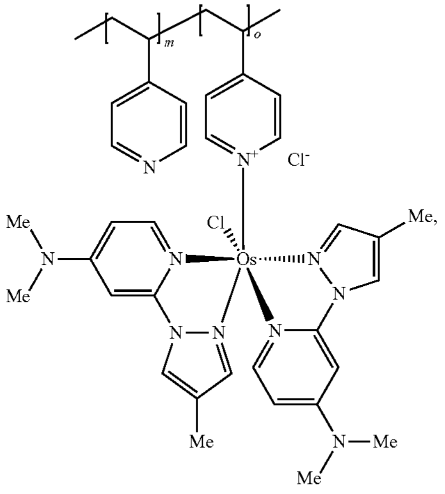

[Chemical formula 44]

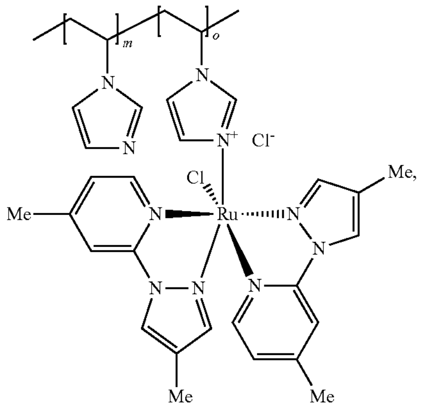

and

[Chemical formul 45]

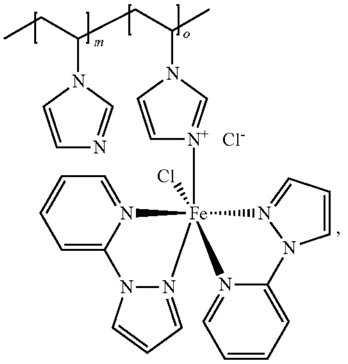

in the formula, m and o are each the same as defined in claim 4.

6. The oxidation-reduction polymer according to claim 4, which is represented by the following Chemical formula 46 or Chemical formula 47, wherein the oxidation-reduction polymer further comprises a crosslinkable functional group:

[Chemical formula 46]

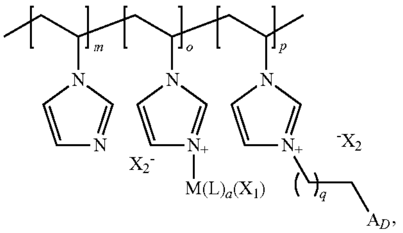

and

[Chemical formula 47]

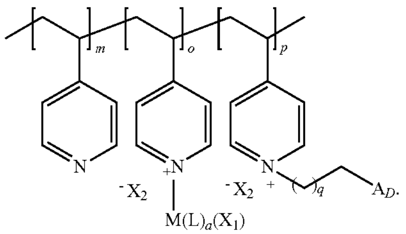

$A_D$ is one kind selected from the group consisting of primary and secondary amine groups, ammonium group, halogen group, epoxy group, azide group, acrylate group, alkenyl group, alkynyl group, thiol group, isocyanate, alcohol group, silane group, and

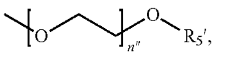

and the $R_5'$ is hydrogen or substituted or unsubstituted $C_{1-4}$ alkyl, and the n" is an integer selected from 1 to 4, and q is an integer selected from 1 to 10, and m, o, or p is each an integer selected from 10 to 600, and M, L, a, $X_1$ and $X_2$ are each the same defined in claim 1.

7. The oxidation-reduction polymer according to claim 6, wherein the compound of Chemical formula 46 or Chemical formula 47 is a compound selected from the group consisting of compounds of the following Chemical formula 48 to 54, and 57 to 60:

[Chemical formula 48]

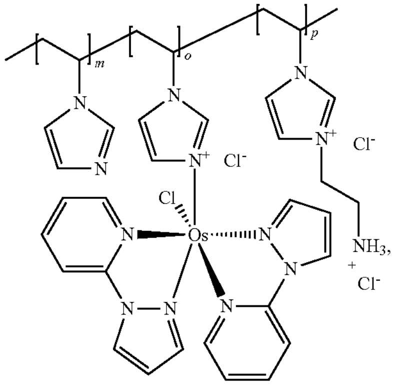

-continued

[Chemical formula 49]

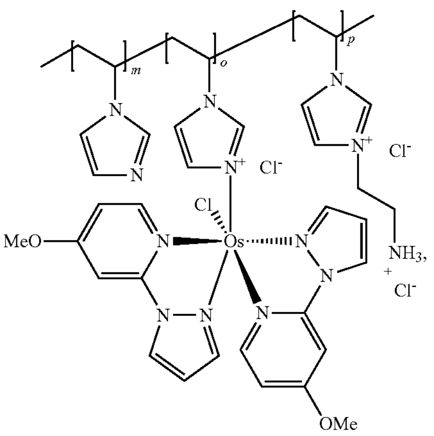

[Chemical formula 50]

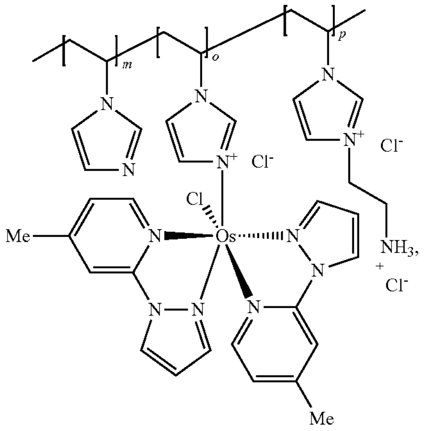

[Chemical formula 51]

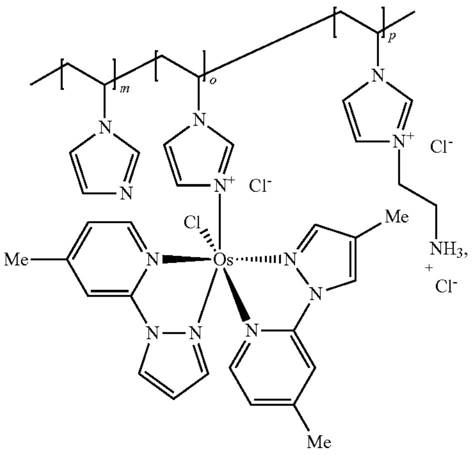

-continued
[Chemical formula 52]
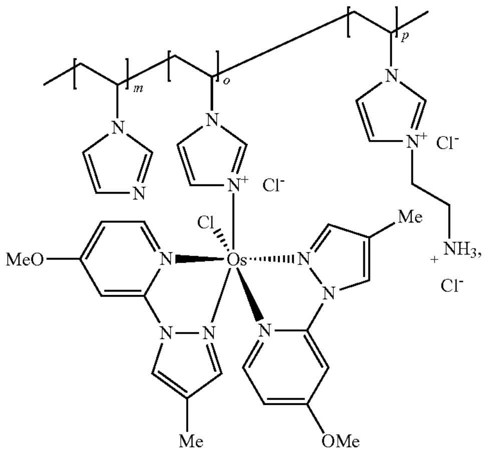
[Chemical formula 53]
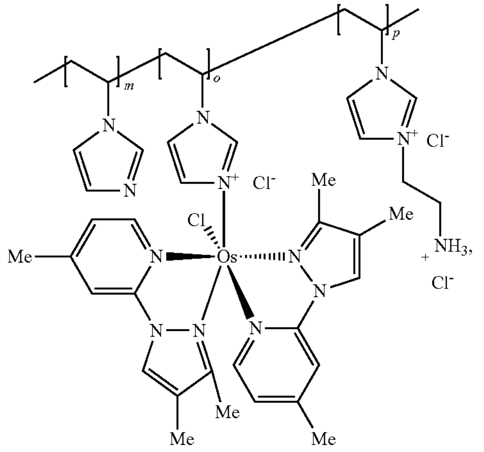
[Chemical formula 54]
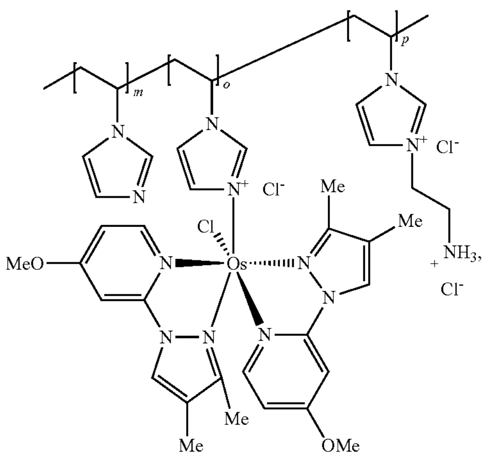
-continued
[Chemical formula 57]
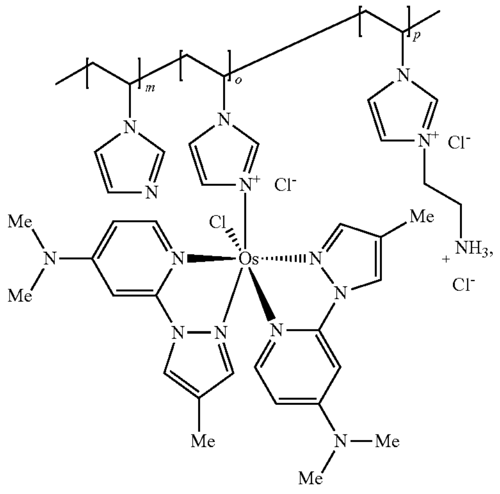
[Chemical formula 58]
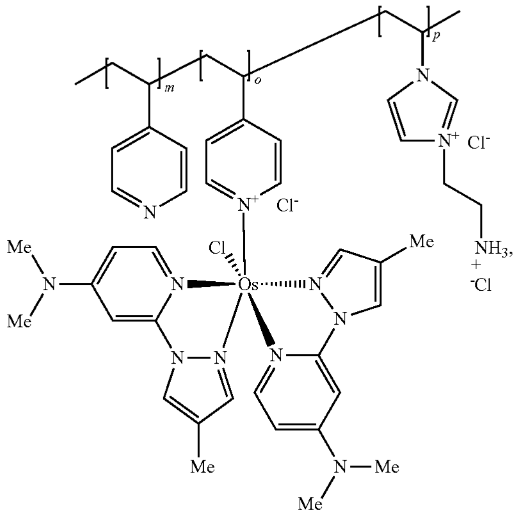
and
[Chemical formula 59]
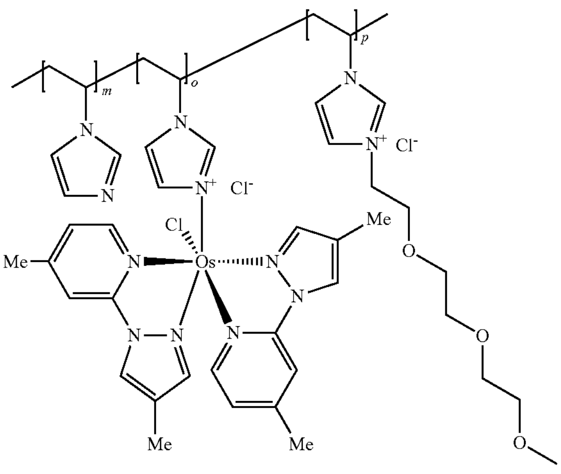
, -continued Chemical formula 60]

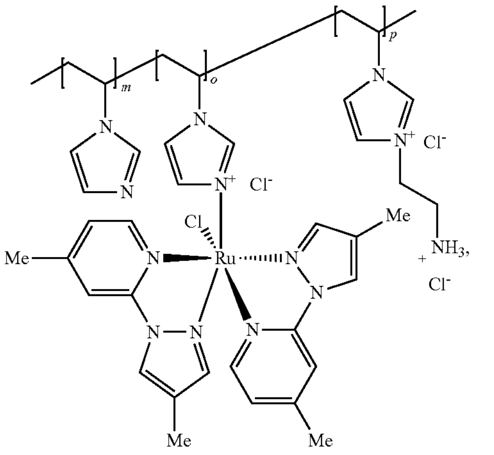

in the formula, m, o and p are the same as defined in claim 6.

8. An electrochemical biosensor comprising the transition metal complex or salt compound thereof of claim 1.

9. The electrochemical biosensor according to claim 8, wherein the electrochemical biosensor is insertable into the body.

10. A sensing membrane for an electrochemical biosensor comprising an enzyme capable of oxidizing-reducing a liquid biological sample; and the transition metal complex or salt compound thereof of claim 1.

11. The sensing membrane for an electrochemical biosensor according to claim 10, wherein the enzyme is at least one selected from the group consisting of dehydrogenase, oxidase and esterase.

12. The sensing membrane according to claim 11, wherein the enzyme is at least one selected from the group consisting of glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase and bilirubin oxidase.

13. The sensing membrane according to claim 11, additionally comprising at least one cofactor selected from the group consisting of flavin adenine dinucleotide (FAD), nicotinamide adenine dinucleotide (NAD), and pyrroloquinoline quinone (PQQ).

14. The sensing membrane according to claim 10, further comprising a carbon nanotube.

15. The sensing membrane according to claim 10, wherein the liquid biological sample is at least one selected from the group consisting of a patient's tissue fluid, blood, cell, plasma, serum, urine, cyst fluid and saliva.

* * * * *